US012646011B2

(12) United States Patent
Longo et al.

(10) Patent No.: US 12,646,011 B2
(45) Date of Patent: Jun. 2, 2026

(54) METHODS AND NUTRITIONAL FORMULATIONS TO INCREASE THE EFFICACY AND REDUCE THE SIDE EFFECTS OF CANCER TREATMENT

(71) Applicant: UNIVERSITY OF SOUTHERN CALIFORNIA, Los Angeles, CA (US)

(72) Inventors: Valter D. Longo, Playa del Rey, CA (US); Changhan Lee, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 928 days.

(21) Appl. No.: 17/204,419

(22) Filed: Mar. 17, 2021

(65) Prior Publication Data

US 2021/0209516 A1     Jul. 8, 2021

Related U.S. Application Data

(63) Continuation of application No. 12/910,508, filed on Oct. 22, 2010, now abandoned.

(60) Provisional application No. 61/254,154, filed on Oct. 22, 2009.

(51) Int. Cl.
| | |
|---|---|
| *G06Q 10/00* | (2026.01) |
| *A23L 13/60* | (2016.01) |
| *A23P 20/20* | (2016.01) |
| *A61K 31/07* | (2006.01) |
| *A61K 31/20* | (2006.01) |
| *A61K 31/202* | (2006.01) |
| *A61K 31/375* | (2006.01) |
| *A61K 31/59* | (2006.01) |

(52) U.S. Cl.
CPC ............. *G06Q 10/00* (2013.01); *A23L 13/65* (2016.08); *A23P 20/20* (2016.08); *A61K 31/07* (2013.01); *A61K 31/20* (2013.01); *A61K 31/202* (2013.01); *A61K 31/375* (2013.01); *A61K 31/59* (2013.01)

(58) Field of Classification Search
CPC ......... G06Q 10/00; A23L 13/65; A23P 20/20; A61K 31/07; A61K 31/20; A61K 31/202; A61K 31/375; A61K 31/59; A61P 3/02; A61P 35/00; A61P 43/00
See application file for complete search history.

(56) References Cited

U.S. PATENT DOCUMENTS

| | | | |
|---|---|---|---|
| 8,211,700 B2 | 7/2012 | Longo | |
| 8,728,815 B2 | 5/2014 | Longo | |
| 8,865,646 B2 | 10/2014 | Longo | |
| 2007/0275934 A1 | 11/2007 | Curd | |
| 2008/0242638 A1* | 10/2008 | Longo | A61K 38/08 514/90 |
| 2014/0328863 A1 | 11/2014 | Longo | |
| 2015/0133370 A1 | 5/2015 | Longo | |

FOREIGN PATENT DOCUMENTS

| | | | |
|---|---|---|---|
| JP | 2001288107 A | * | 10/2001 |
| WO | 01/06983 A2 | | 2/2001 |

OTHER PUBLICATIONS

Mehanna et al. (Refeeding syndrome—awareness, prevention and management. Head & Neck Oncology, 2009 (Year: 2009).*
Klurfeld et al., (Inhibition of Chemically Induced Mammary and Colon Tumor Promotion by Caloric Restriction in Rats Fed Increased Dietary Fat, Cancer Research 47, 1987 (Year: 1987).*
Mizushima et al. (Autophagy fights disease through cellular self-digestion, Nature 2008 (Year: 2008).*
Raffaghello et al. (Starvation-dependent differential stress resistance protects normal but not cancer cells against high-dose chemotherapy. PNAS 2008 (Year: 2008).*
Nakamura et al. (JP 2001288107 A) Translated (Year: 2001).*
Boivin et al. (Antiproliferative and antioxidant activities of common vegetables: A comparative study, Food Chemistry, 2009). (Year: 2009).*
Carper, "The Calorie Cancer Connection," The Washington Post, Apr. 25, 1989, 2 pgs.
Folador A., et al., "Effect of fish oil supplementation for 2 generations on changes in macrophage function Induced by Walker 256 cancer cachexia in rats," Int J Cancer, (2006) vol. 120, pp. 344-350.
Hursting, S.D. et al., "Calorie Restriction, Aging, and Cancer Prevention: Mechanisms of Action and Applicability to Humans*", Annual Review of Medicine : Selected Topics in the Clinical Sciences, v. 54, n. 1 (2003), 24 pgs.
Jiang, Y. et al., "Potential Mechanisms of Cancer Prevention by Weight Control," Biophysical reviews and Letters 3(3), (2008), pp. 421-437.
Jie, Wu, The Elderly Calcium Supplement Diet Therapy Cookbook, Edition 1, Jindun Publishing House, Jan. 31, 2009, p. 471, paragraph 6 (translation) (1 pg.).

(Continued)

*Primary Examiner* — Robert A Wax
*Assistant Examiner* — John Seungjai Kwon
(74) *Attorney, Agent, or Firm* — Brooks Kushman P.C.

(57) ABSTRACT

The present invention relates to methods of protecting patients and sensitizing cancer cells in combination with chemotherapy and/or radiation therapy. More specifically, the invention provides nutritional methods and formulations that are capable of reducing cancer growth without causing chronic weight loss in patients, protecting normal cells, tissues and organs from chemotherapy and/radiation therapy, and sensitizing cancer cells against low, normal and high-dose chemotherapy. Some of the methods also impede cancer growth even without chemotherapy.

13 Claims, 58 Drawing Sheets

(56) References Cited

OTHER PUBLICATIONS

Kritchevsky and Klurfield, "Dietary Fat versus Caloric Content in Intiation and Promotion of 7,12-Dimethylbenz(a)anthracene-induced Mammary Tumorigenesis in Rats," Cancer Research 44 (1984), pp. 3174-3177.

Longo, V.D. et al: "Calorie restriction and cancer prevention: metabolic and molecular mechanisms", ?Rends in Pharmacological Sciences., vol. 31, No. 2, Feb. 1, 2010, 20 Pages.

Mehanna et al., "Refeeding Syndrome: what it is, and how to prevent and treat it," BMJ (2008), v. 336, pp. 1495-1498.

Nebeling, L.C. et al., "Effects of a Ketogenic diet on tumor metabolism and nutritional status in pediatric oncology patients: Two case reports," J. of the American College of Nutrition, American College of Nutrition, Wilmington, NC, v. 14, n. 2, (1995), 8 pgs.

Nebeling, L.C. et al., "Implementing a Ketogenic Diet Based on Medium-Chain Triglyceride Oil in Pediatric Patients with Cancer," J. of American Dietetic Assn, the Association, Chicago, IL, v. 95, n. 6, (1995), 6 pgs.

Zhang, Meihua, New Century Youth Science Classic—Science and Technology Horizon, Inner Mongolia Children's Publishing House, Ed. 1, Dec. 31, 2000, p. 126, paragraph 3 (translation) (1 pg.).

European Search Report dtd Mar. 30, 2016 from EP Appn. No. 10 82 5771 filed Dec. 14, 2012, 9 pgs.

Exam Report dated Sep. 30, 2014 from Chinese Appn. No. 201080056074.7 filed Jun. 11, 2012, 12 pgs.

Office Action dated Nov. 3, 2014 from Australian Appn. No. 2010310515 filed Apr. 19, 2012, 7 pgs.

\* cited by examiner

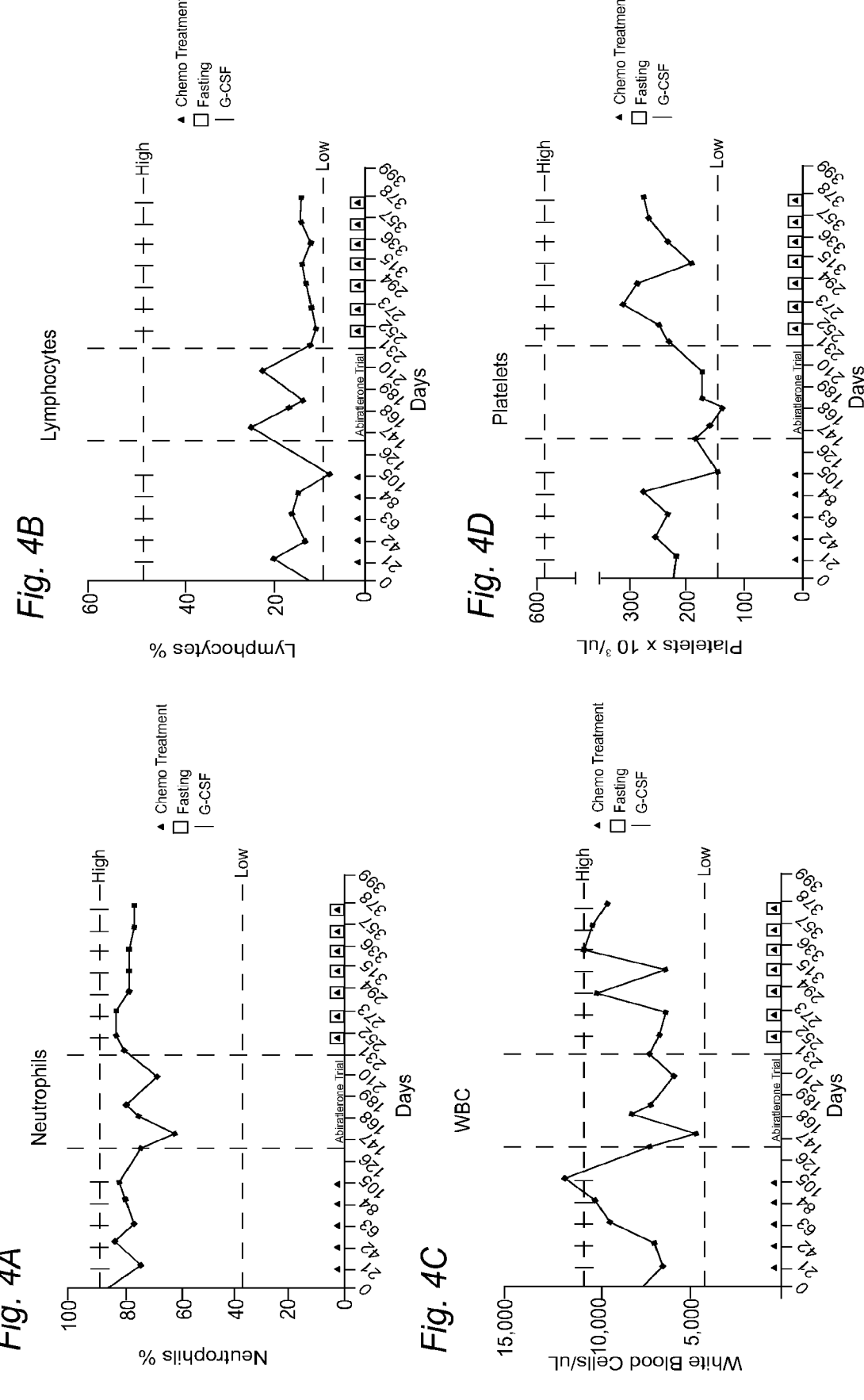

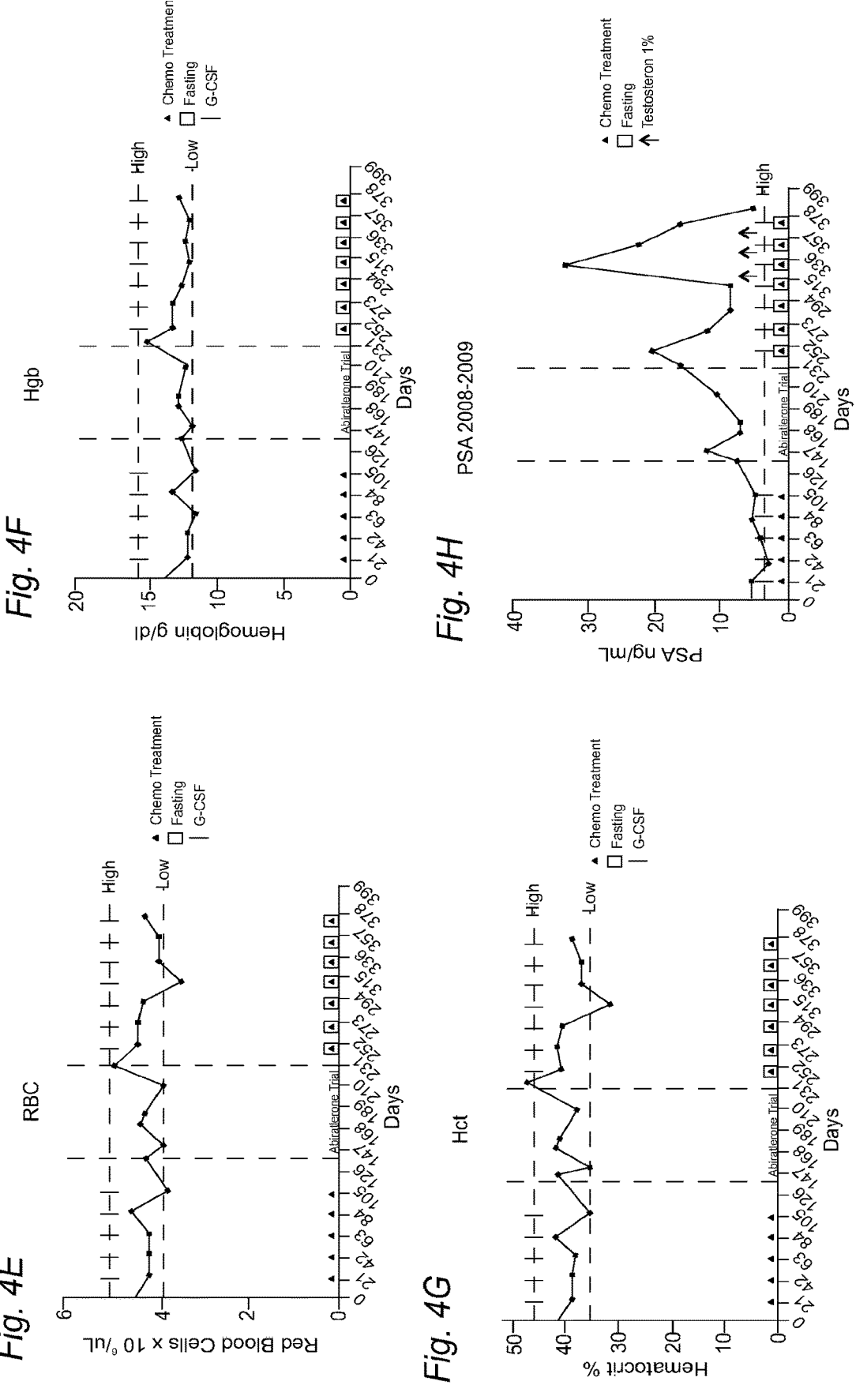

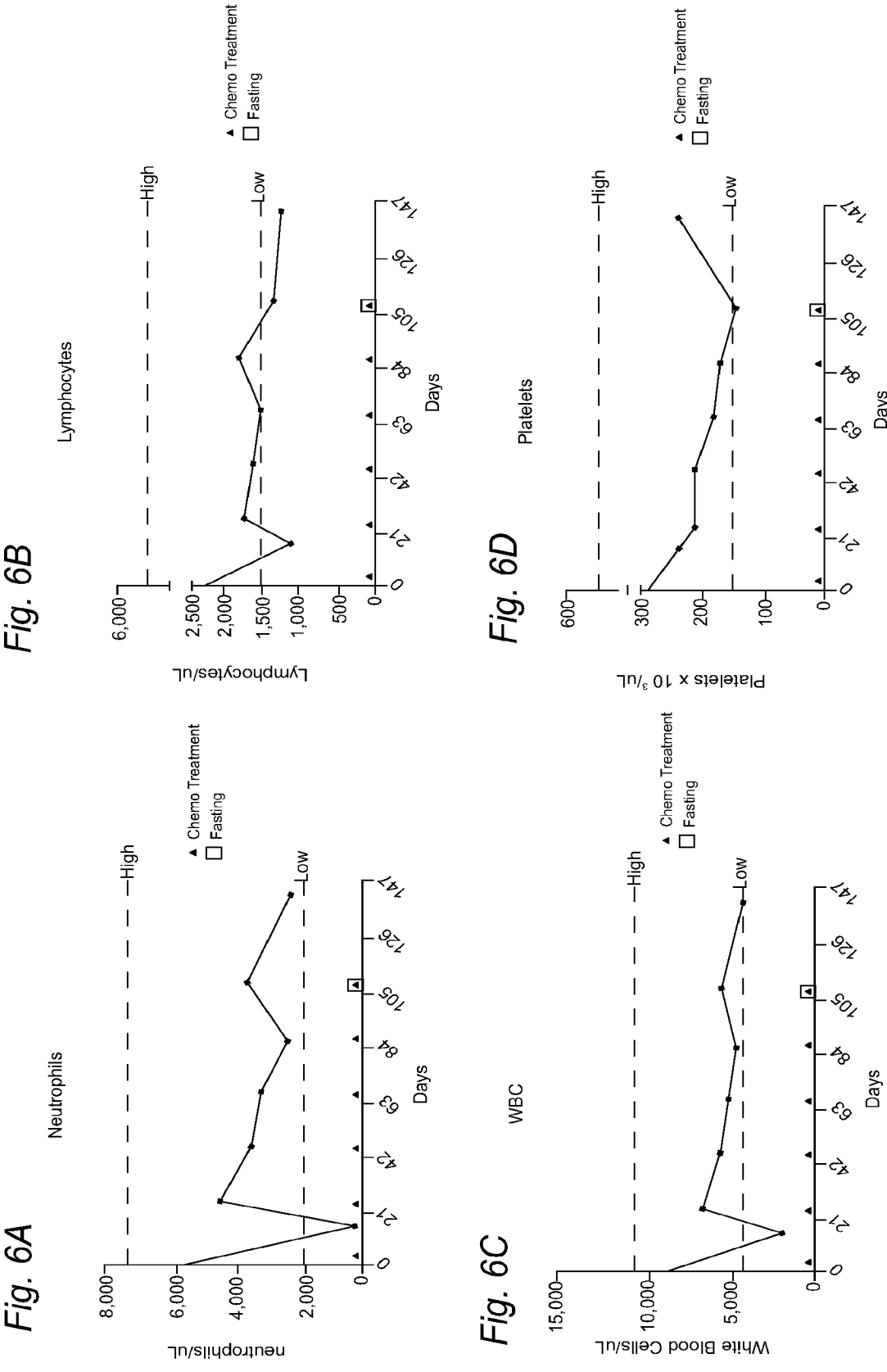

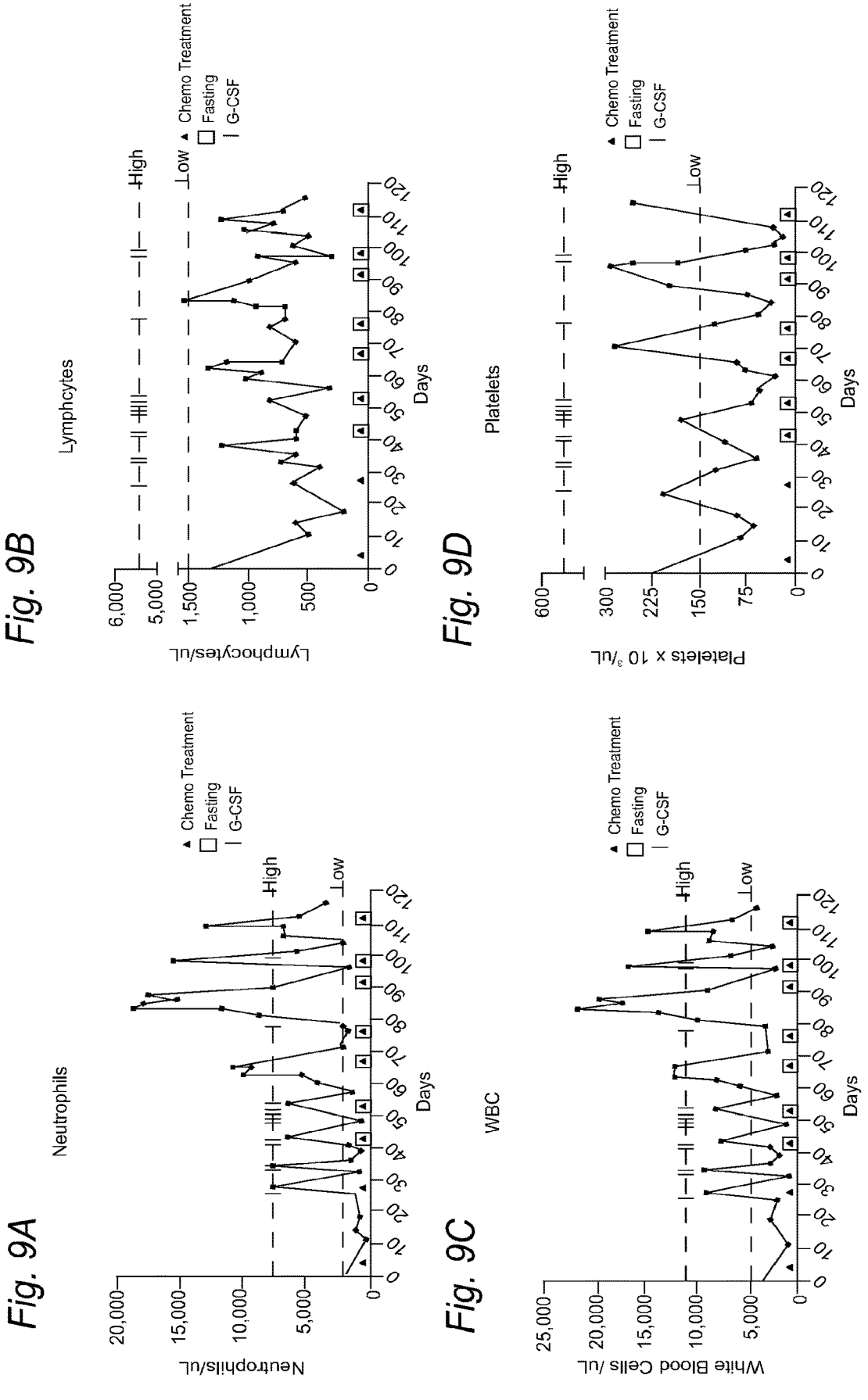

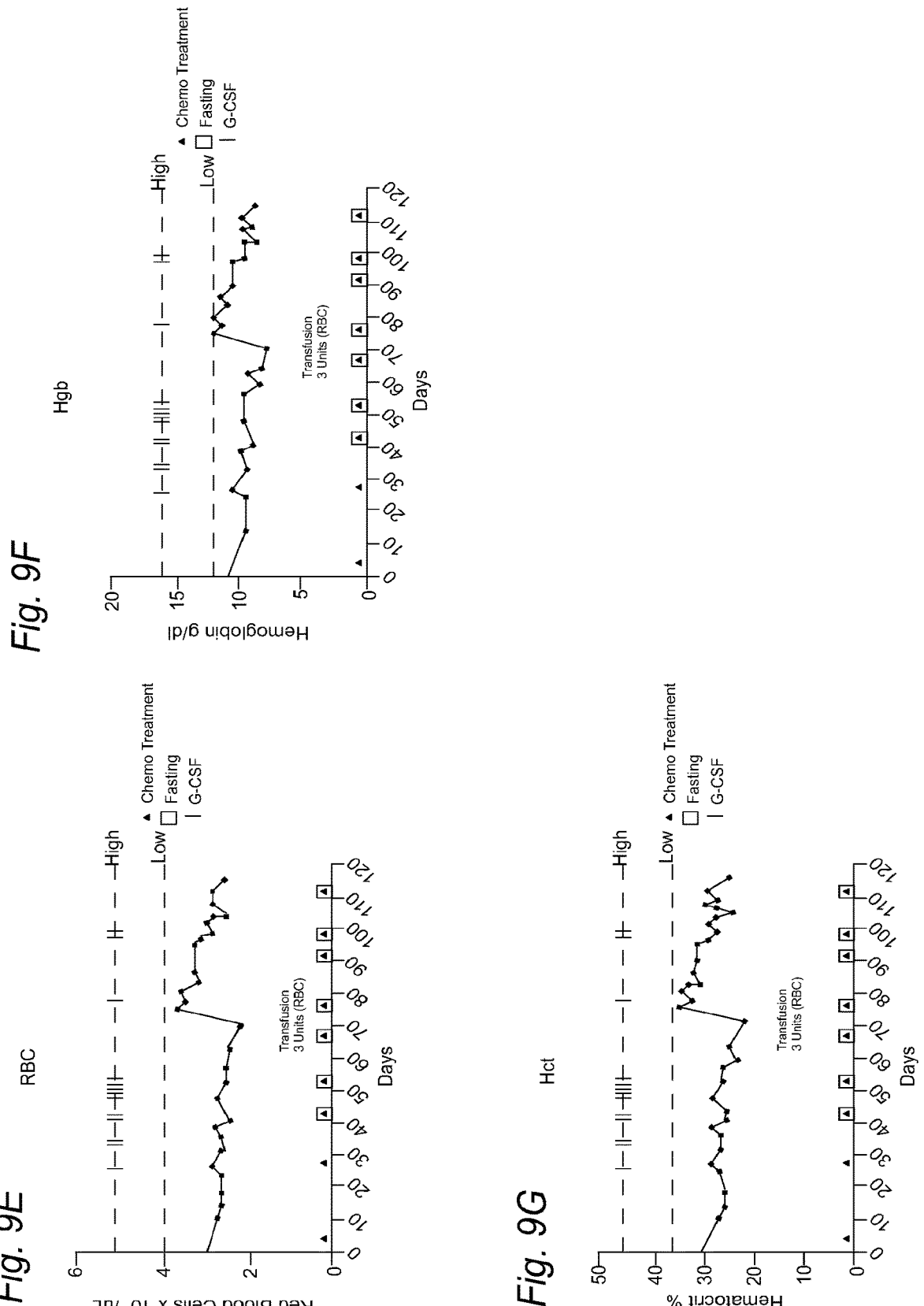

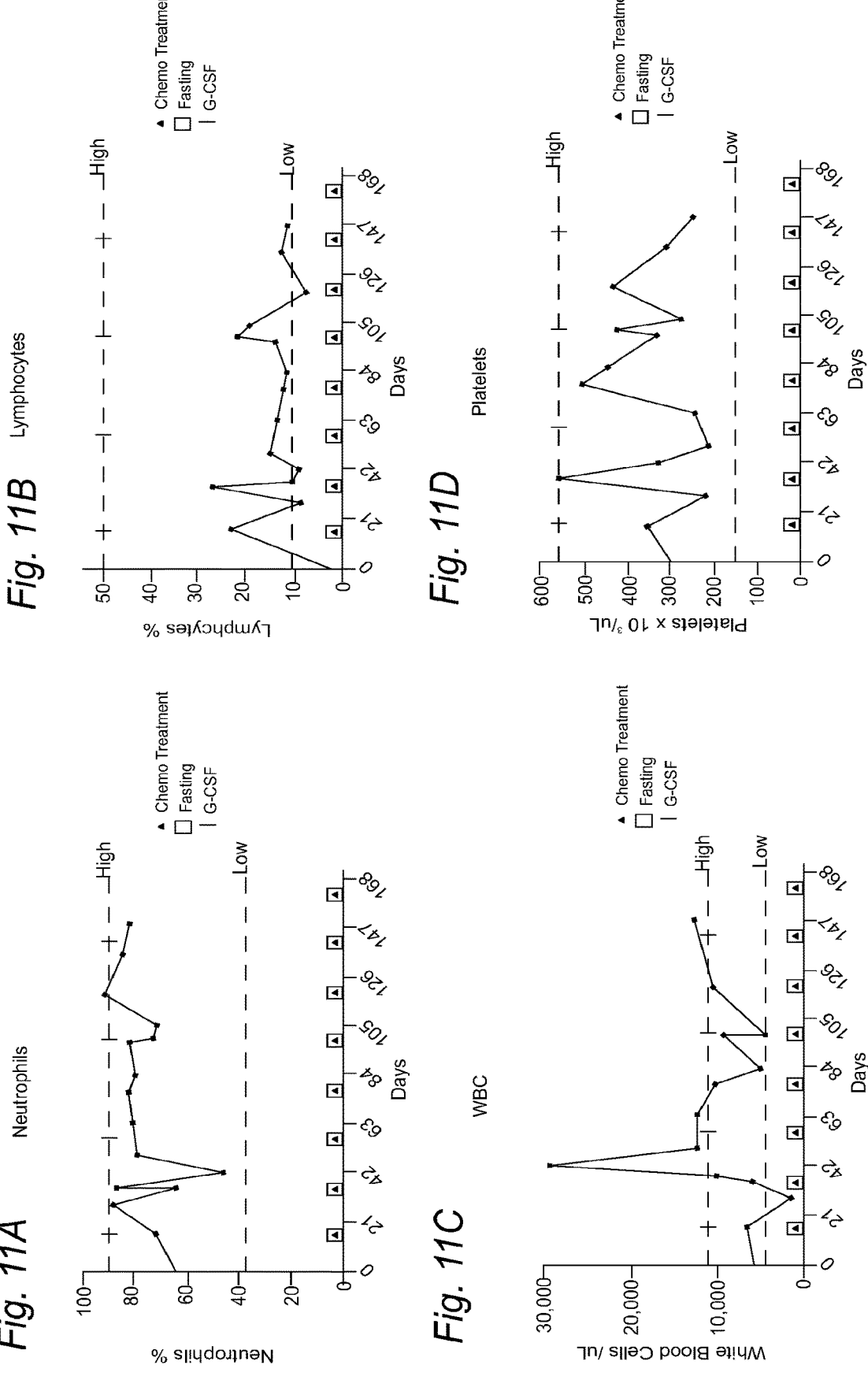

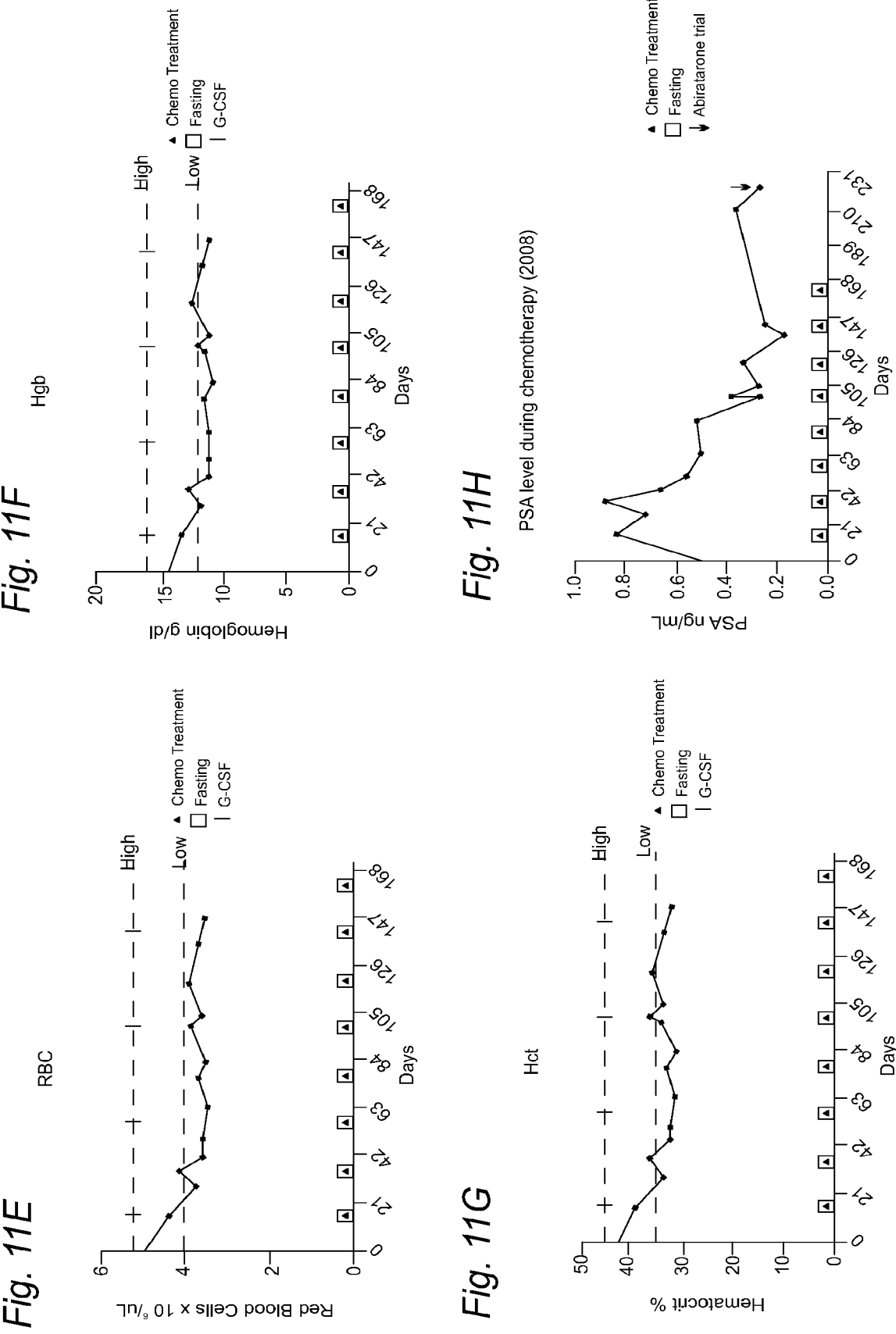

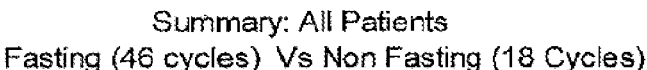
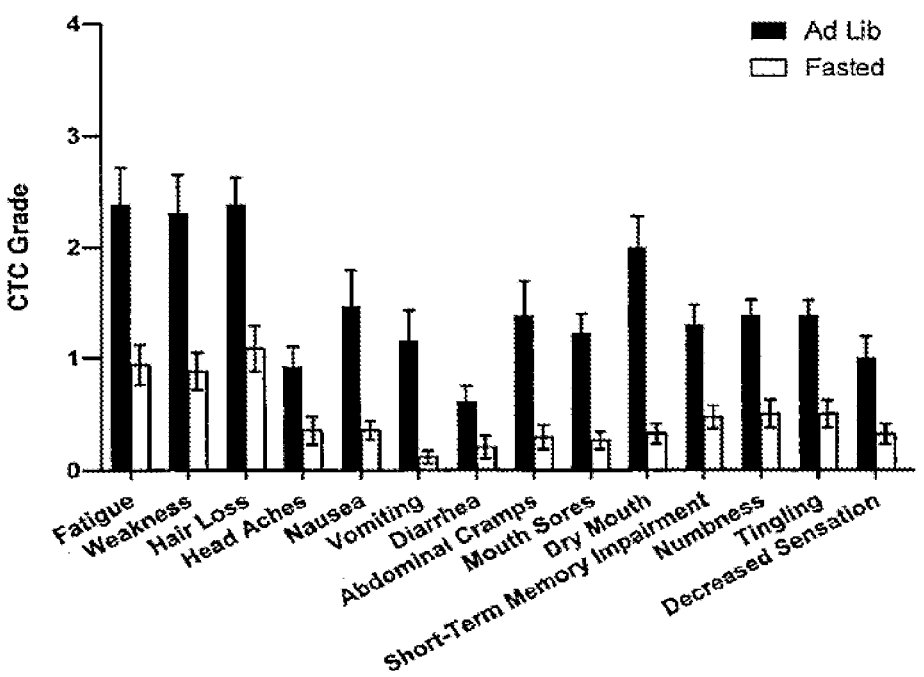
Fig. 17A
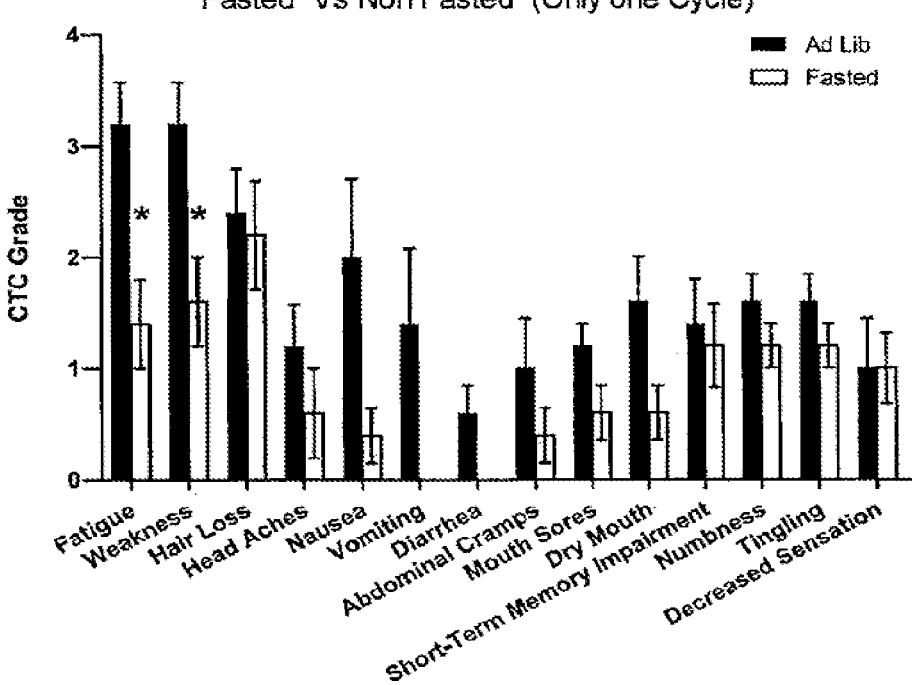
Fig. 17B

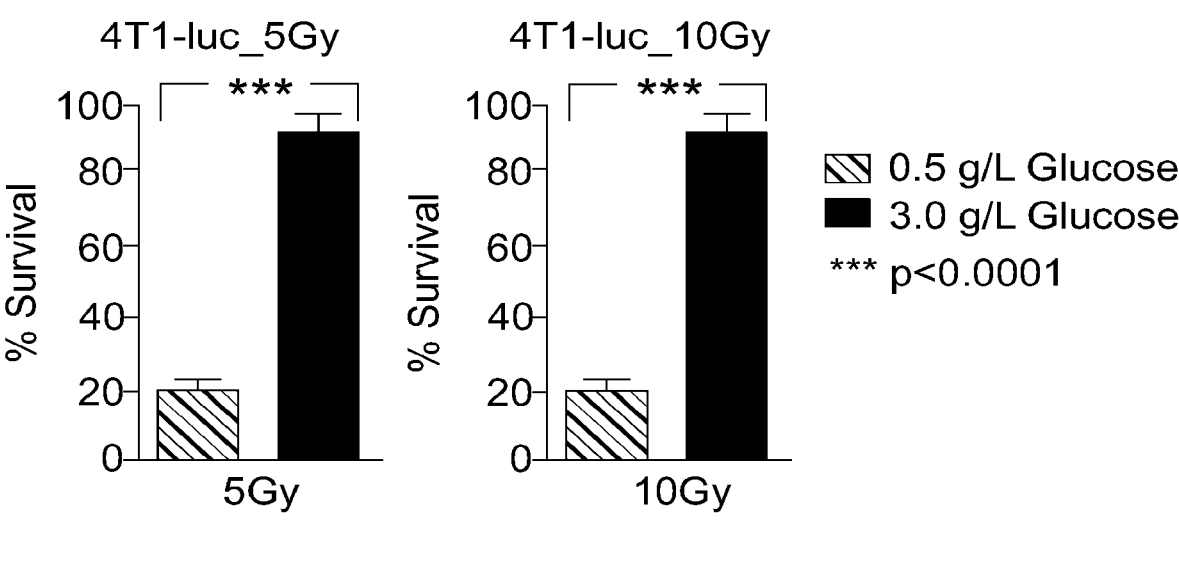
*Fig. 18A*          *Fig. 18B*
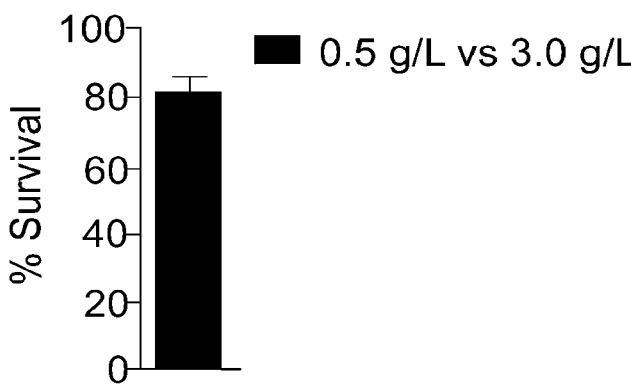
*Fig. 18C*

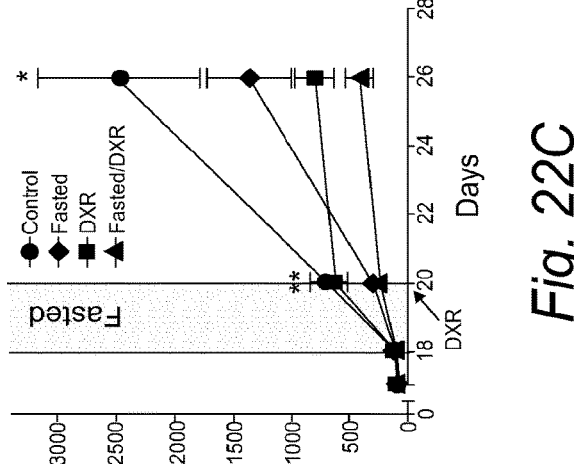
*Fig. 22A*
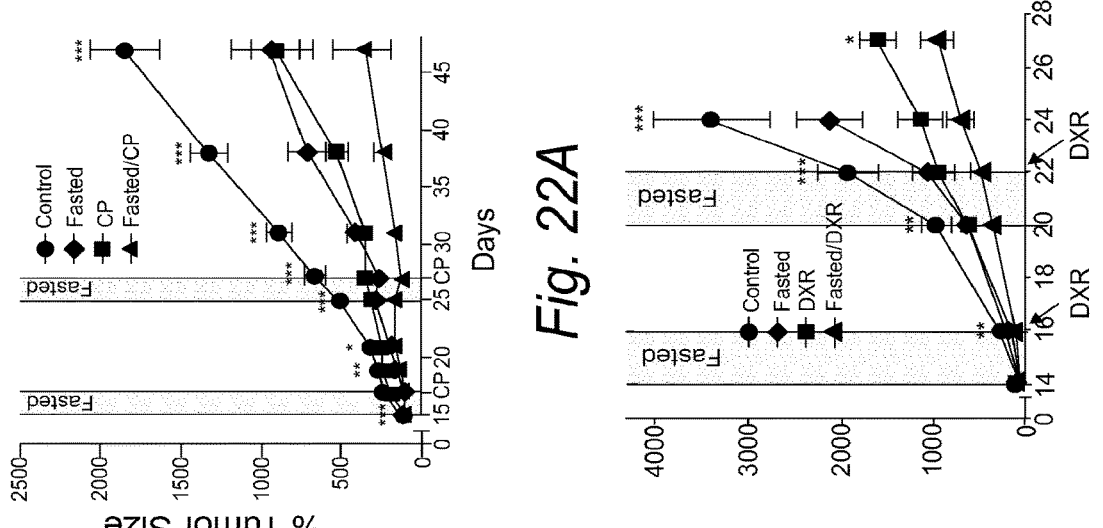
*Fig. 22B*
*Fig. 22C*

Doxorubicin (uM)

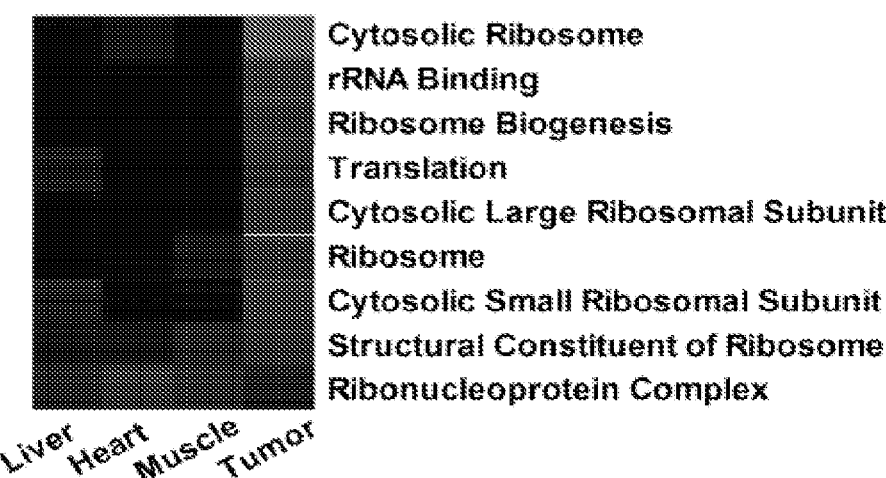
Cytosolic Ribosome
rRNA Binding
Ribosome Biogenesis
Translation
Cytosolic Large Ribosomal Subunit
Ribosome
Cytosolic Small Ribosomal Subunit
Structural Constituent of Ribosome
Ribonucleoprotein Complex
Liver  Heart  Muscle  Tumor
*Fig. 38*
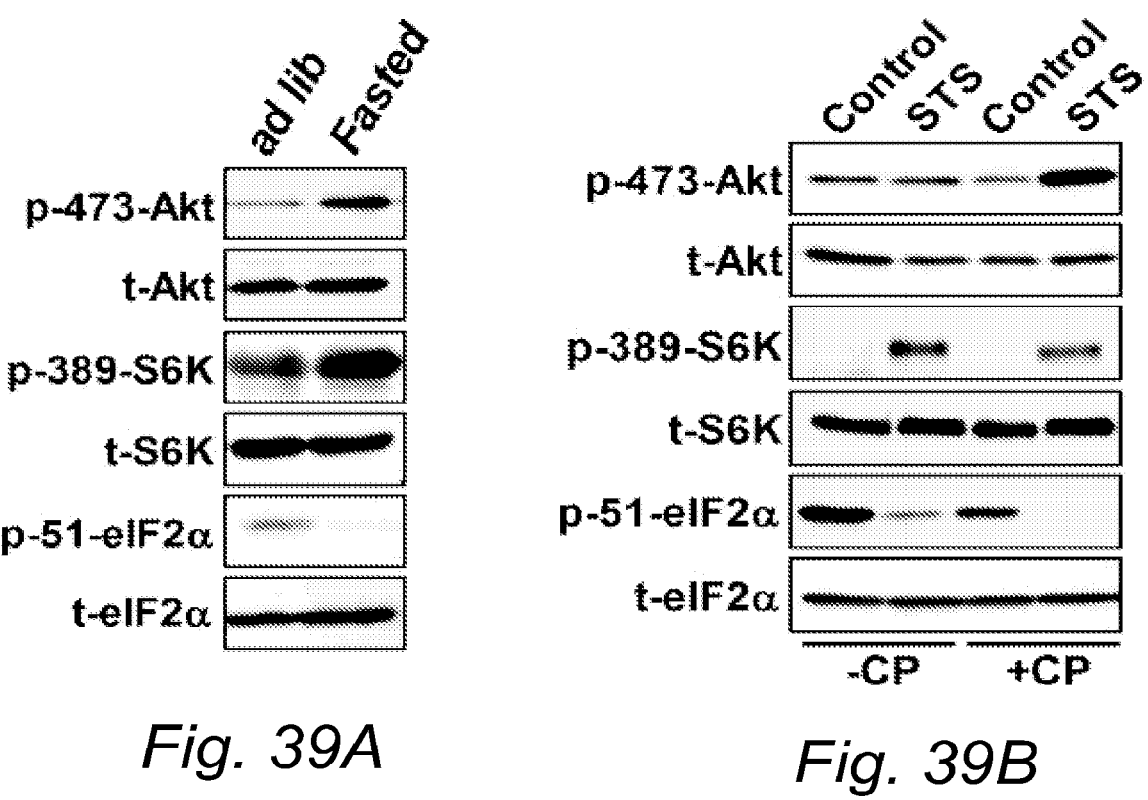
*Fig. 39A*                    *Fig. 39B*

METHODS AND NUTRITIONAL FORMULATIONS TO INCREASE THE EFFICACY AND REDUCE THE SIDE EFFECTS OF CANCER TREATMENT

CROSS-REFERENCE TO RELATED APPLICATIONS

This application is a continuation of U.S. patent application Ser. No. 12/910,508 filed Oct. 22, 2010, which claims the benefit of U.S. provisional Application No. 61/254,154 filed Oct. 22, 2009, the disclosure of which is incorporated in its entirety by reference herein.

TECHNICAL FIELD

The present invention relates in general to diet and cancer treatment. More specifically, the invention provides methods that may be used to sensitize cancer cells to chemotherapy drugs, while protecting normal cells.

BACKGROUND

Chemotherapy can extend survival in patients diagnosed with a wide range of malignancies. However, toxic side-effects to normal cells and tissues limits chemotherapy dose intensity, frequency, and efficacy. For instance, the cardio-toxicity and nephrotoxicity associated with the widely pre-scribed anti-cancer drugs, doxorubicin and cisplatin, respec-tively, limit their full therapeutic potential (Rajagopalan, S. Cancer Res. 1988; Hale, J. P. Arch. Dis. Child 1994; Dobyan, D. C., J. Pharmacol. E.T1980; Fillastre, J. P. Toxicology let 1989). Thus, reduction of undesired toxicity by selective protection of normal cells without compromis-ing the killing of malignant cells represents a promising strategy to enhance cancer treatment.

Recently, a fasting-based intervention capable of differ-entially protecting normal but not cancer cells against high-dose chemotherapy in cell culture and in neuroblastoma-bearing mice was reported (Raffaghello, L. PNAS 2008). In the neuroblastomaxenograft mouse model, mice were allowed to consume only water for 48 hours prior to etopo-side treatment. Whereas high dose etoposide led to 50% lethality in ad lib fed mice, fasting not only protected chemotoxicity associated with the drug but also delayed neuroblastoma metastases-dependent death (Raffaghello, L. PNAS 2008).

Calorie restriction is known to enhance stress resistance and extend life span in organisms ranging from yeast to mammals. Calorie restriction has also been shown to delay cancer growth, but its effect is small and it cannot be combined with chemotherapy nor can it be applied alone, since it requires a long-term weight loss which is detrimental to cancer patients and also very difficult to maintain.

Accordingly, for at least these reasons, there is a need for additional methods of treating cancer that effectively incor-porate a diet that assists the treatment and alleviates che-motherapeutic side-effects.

SUMMARY

Against this prior art background, a method for alleviating cancer growth or a symptom of cancer is provided. The method of this embodiment includes a step in which a patient with cancer is identified and then provided with a first diet for a first predetermined period of time. The first diet provides the patient with at most 50% of the patient's normal caloric intake with at least 50% of the kilocalories being derived from fat, preferably monounsaturated. The patient is then provided with a second diet for a second predetermined period of time. The second diet provides the patient with at most 500 kcal/day. The patient is then provided with a third diet that optimizes weight regain and the replenishment of essential nutrients required for optimal recovery and health of normal cells and organs. The present embodiment provides a short-term modified diet protocol that is effective in protecting normal cells and impeding and retarding cancer cell growth. The protocol and modified diet will promote these effects without causing chronic weight loss in patients, In another embodiment, a method of sensitizing cancer to chemotherapy drugs is provided. The method includes a step in which a patient with cancer is identified and then provided with a first diet for a first predetermined period of time. The first diet provides the patient with at most 50% of the patient's normal caloric intake with at least 50% of the kilocalories being derived from fat. The patient is then provided with a second diet for a second predetermined period of time. The second diet provides the patient with at most 500 kcal/day. The patient is then provided with a third diet that optimizes weight regain and the replenishment of essential nutrients required for optimal recovery and health of normal cells and organs. The present embodiment pro-vides a short-term modified diet protocol that is effective in protecting normal cells and sensitizing cancer from/to che-motherapy (Differential Stress Resistance). The protocol and modified diet will promote these effects without causing chronic weight loss in patients.

These results are intriguing in view of the generally accepted belief by oncologists that fasting is potentially harmful for cancer patients who have been weakened by prior chemotherapy cycles or are emaciated.

In still another embodiment, a method of sensitizing cancer to radiation therapy is provided. The method includes a step in which a patient with cancer is identified and then provided with a first diet for a first predetermined period of time. The first diet provides the patient with at most 50% of the patient's normal caloric intake with at least 50% of the kilocalories being derived from fat. The patient is then provided with a second diet for a second predetermined period of time. The second diet provides the patient with at most 500 kcal/day. The patient is then provided with a third diet that optimizes weight regain and the replenishment of essential nutrients required for optimal recovery and health of normal cells and organs. The present embodiment pro-vides a short-term modified diet protocol that is effective in protecting normal cells and sensitizing cancer from/to radia-tion therapy (Differential Stress Resistance). The protocol and modified diet will promote these effects without causing chronic weight loss in patients.

In another embodiment, formulations containing specific ranges of proteins, essential amino acids, carbohydrates, fats, vitamins, minerals and essential fatty acids to delay cancer growth when administered alone or protect the host against chemotherapy and/or radiation therapy and sensitize cancer cells to chemotherapy and/or radiation therapy are provided.

Figure 2:
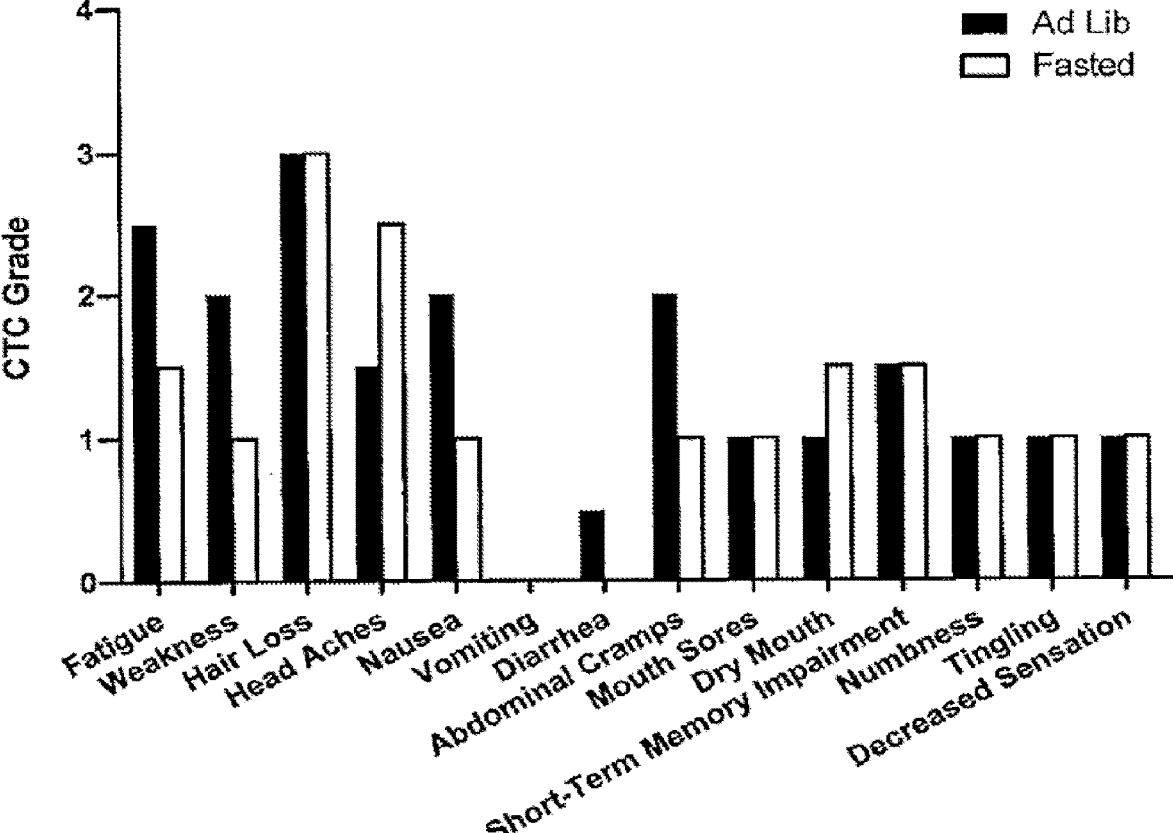
Figure 3:
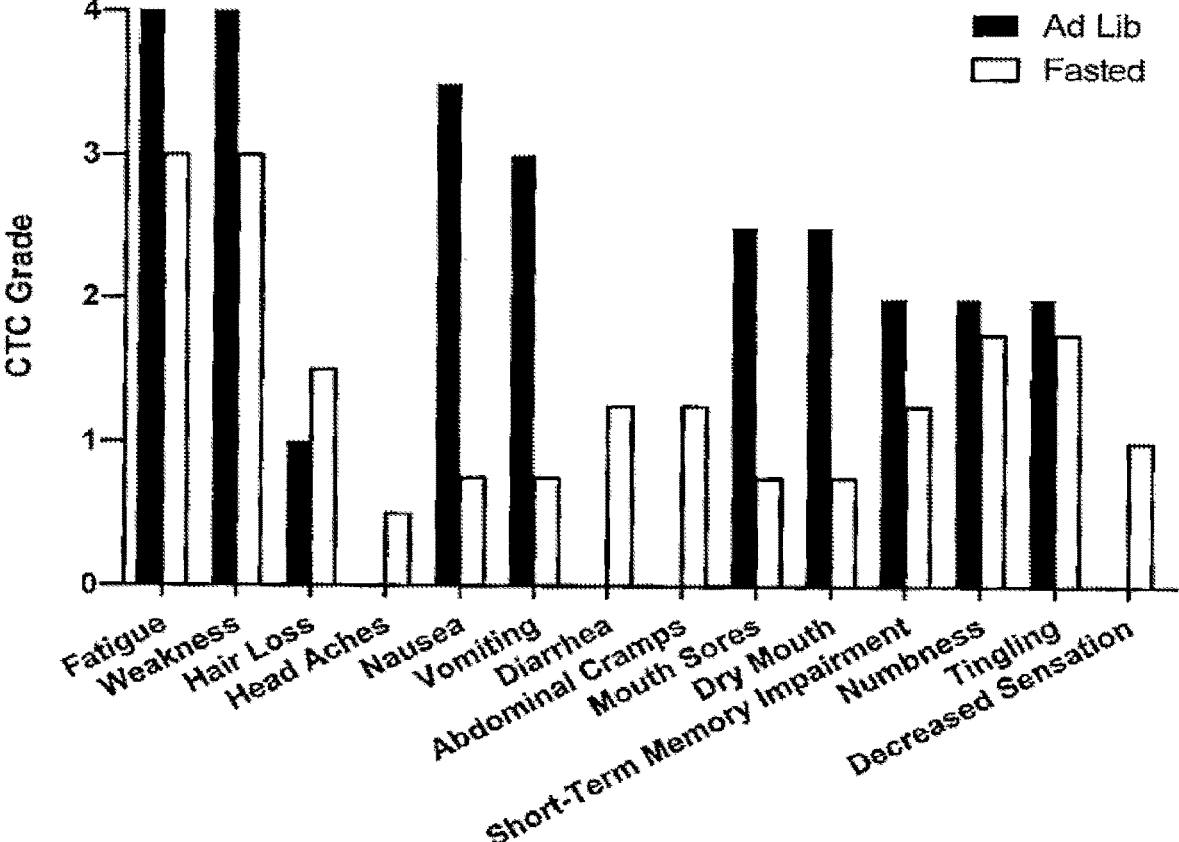
Figure 5:
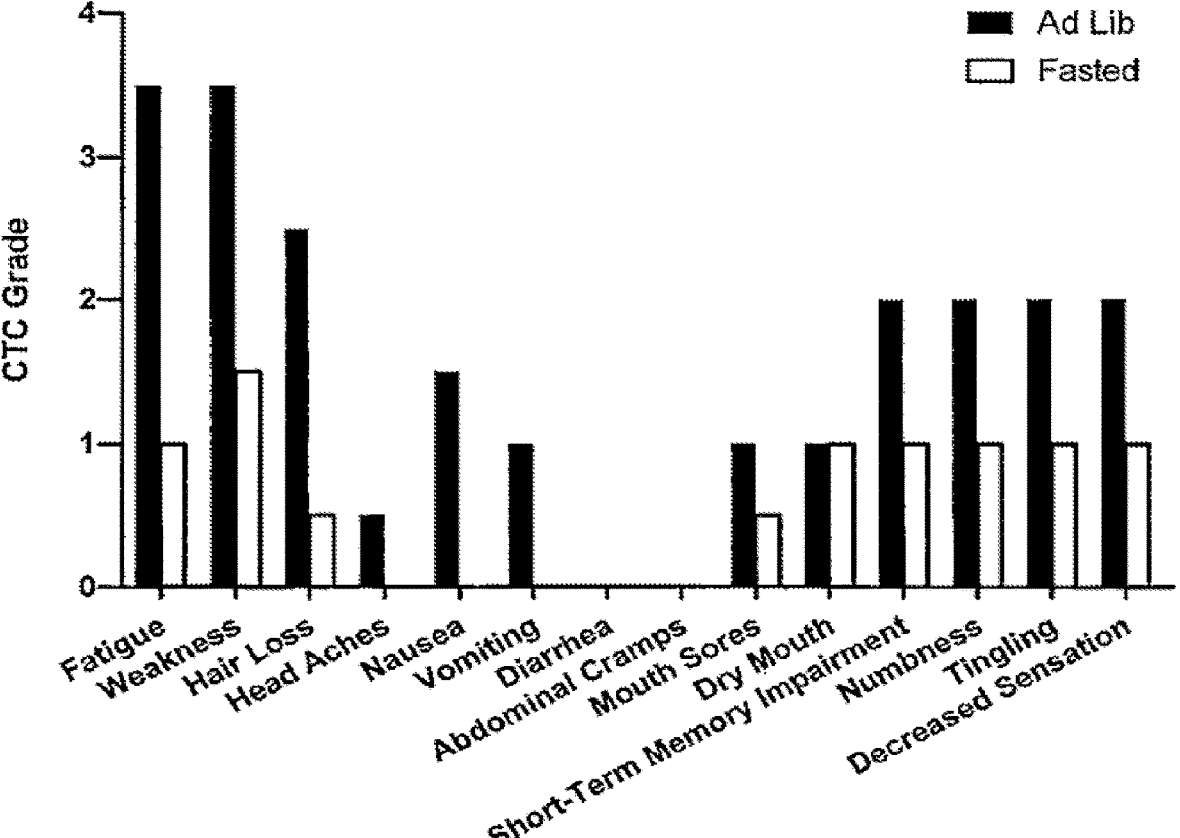
Figure 6F:
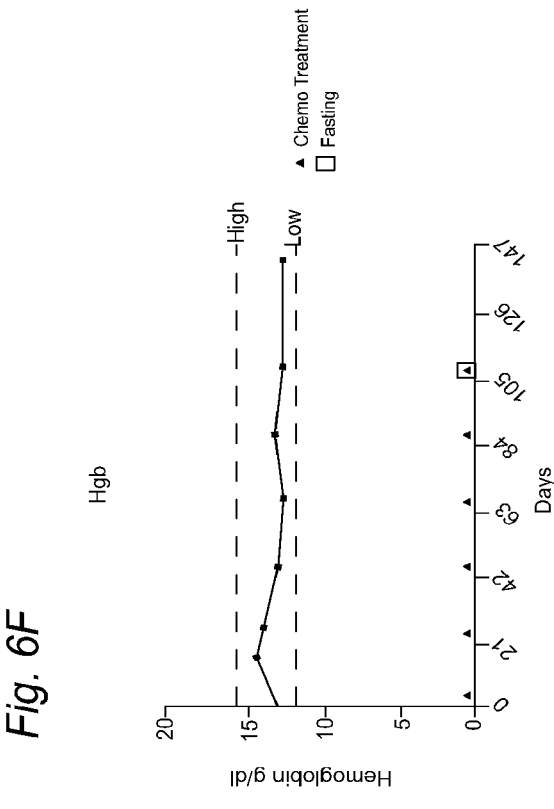
Figure 6E:
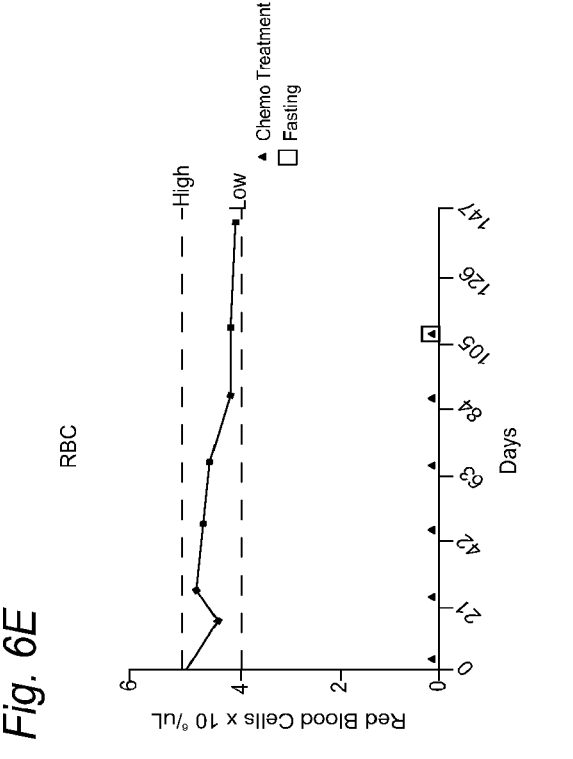
Figure 6G:
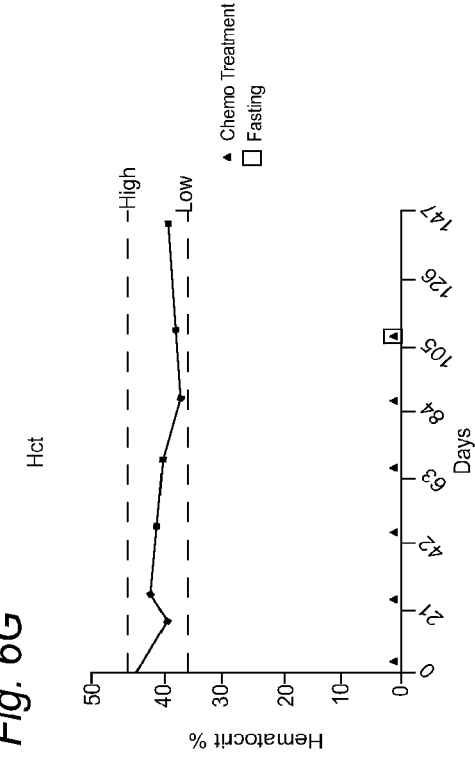
Figure 7:
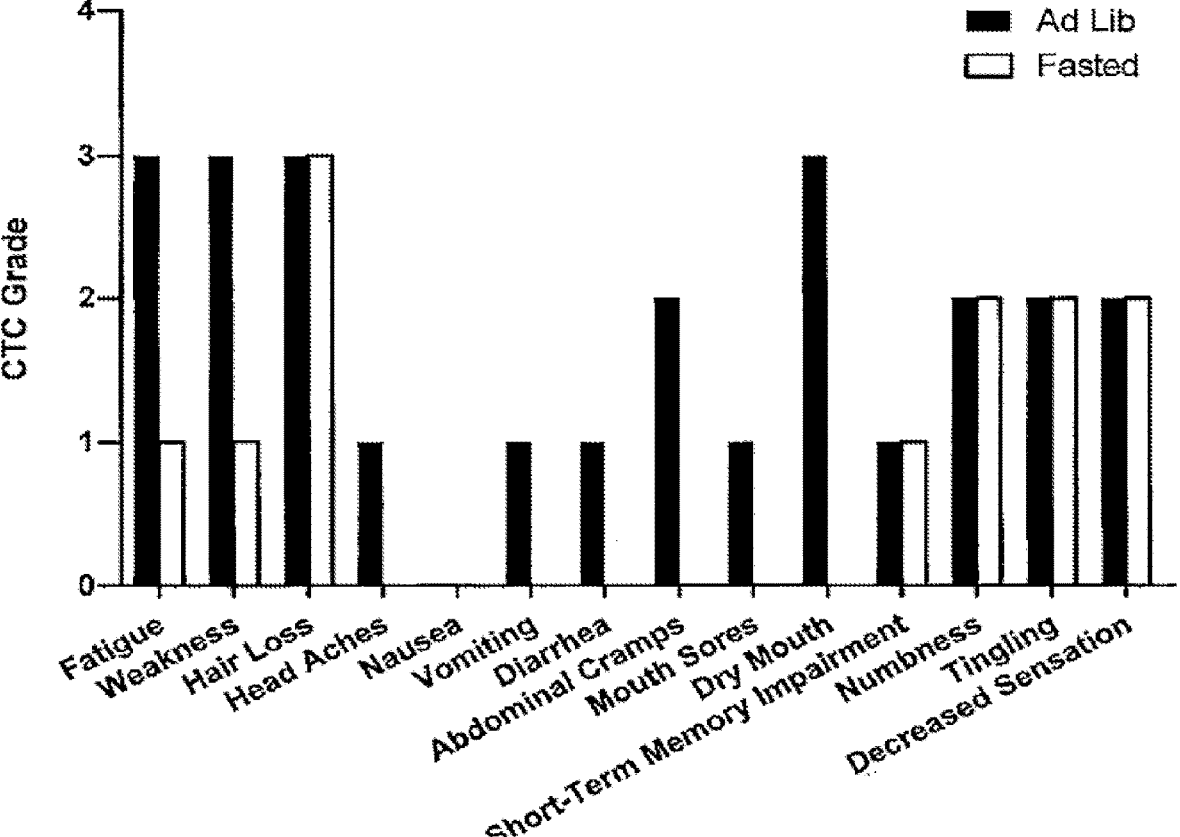
Figure 8:
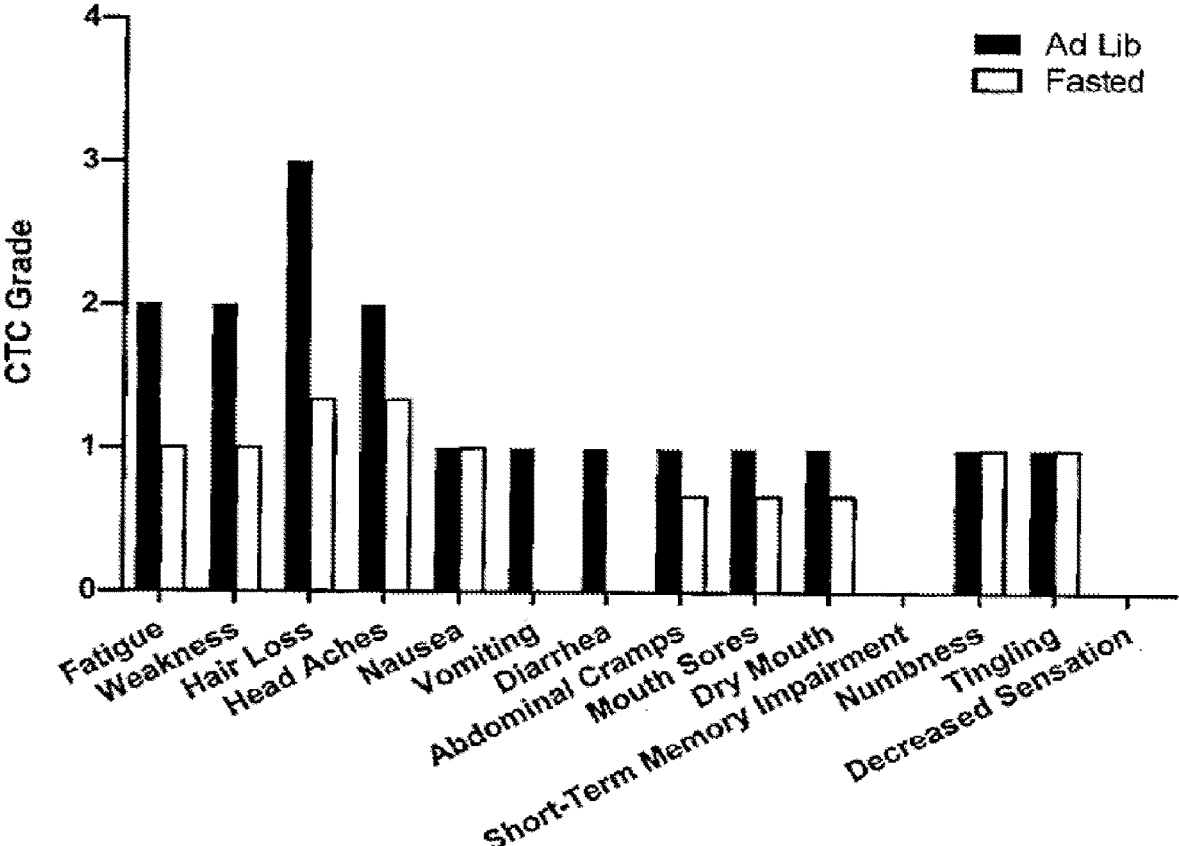
Figure 10:
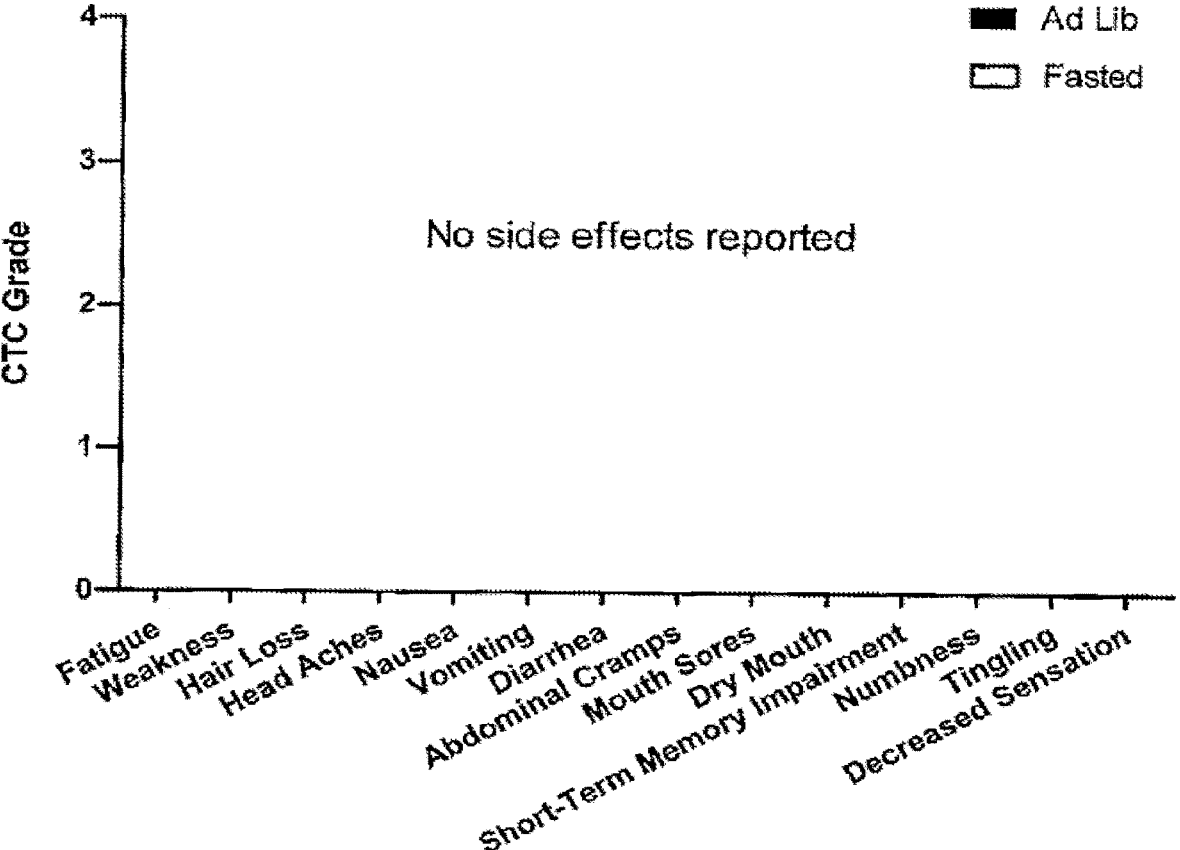
Figure 12:
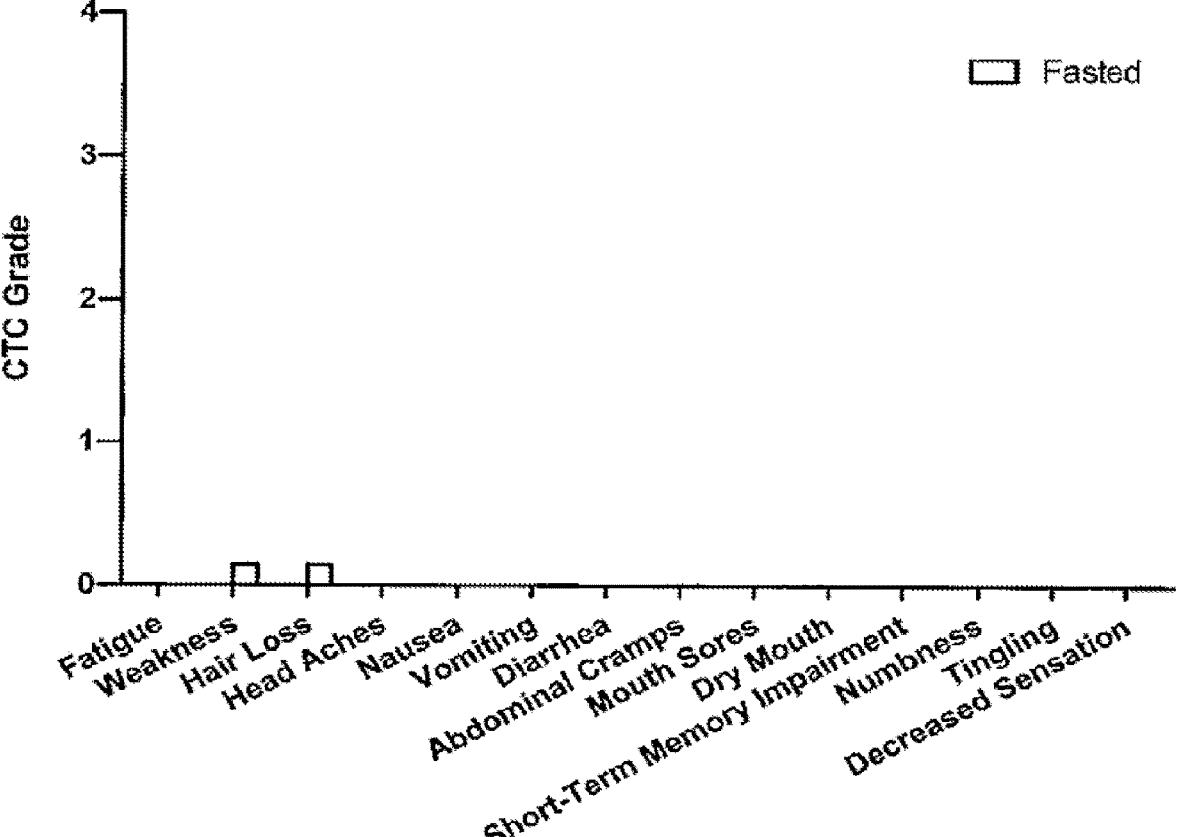
Figure 13:
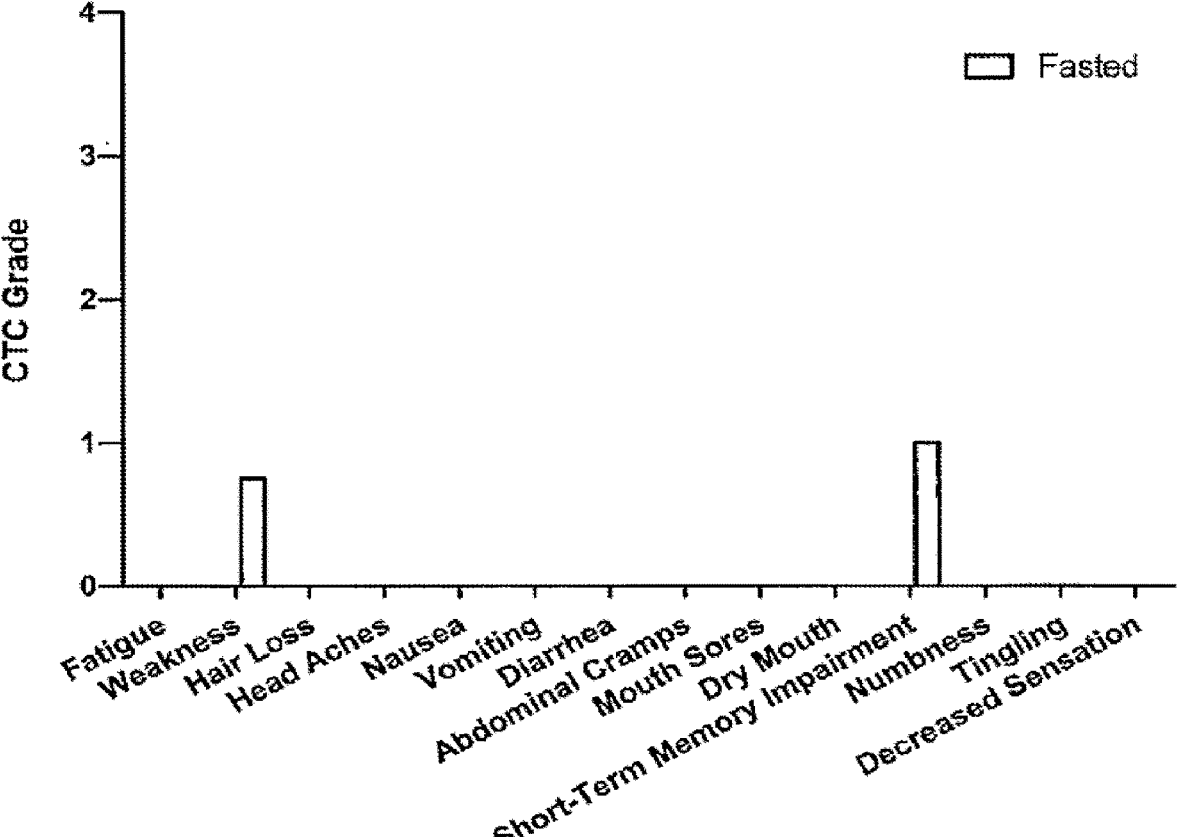
Figure 14:
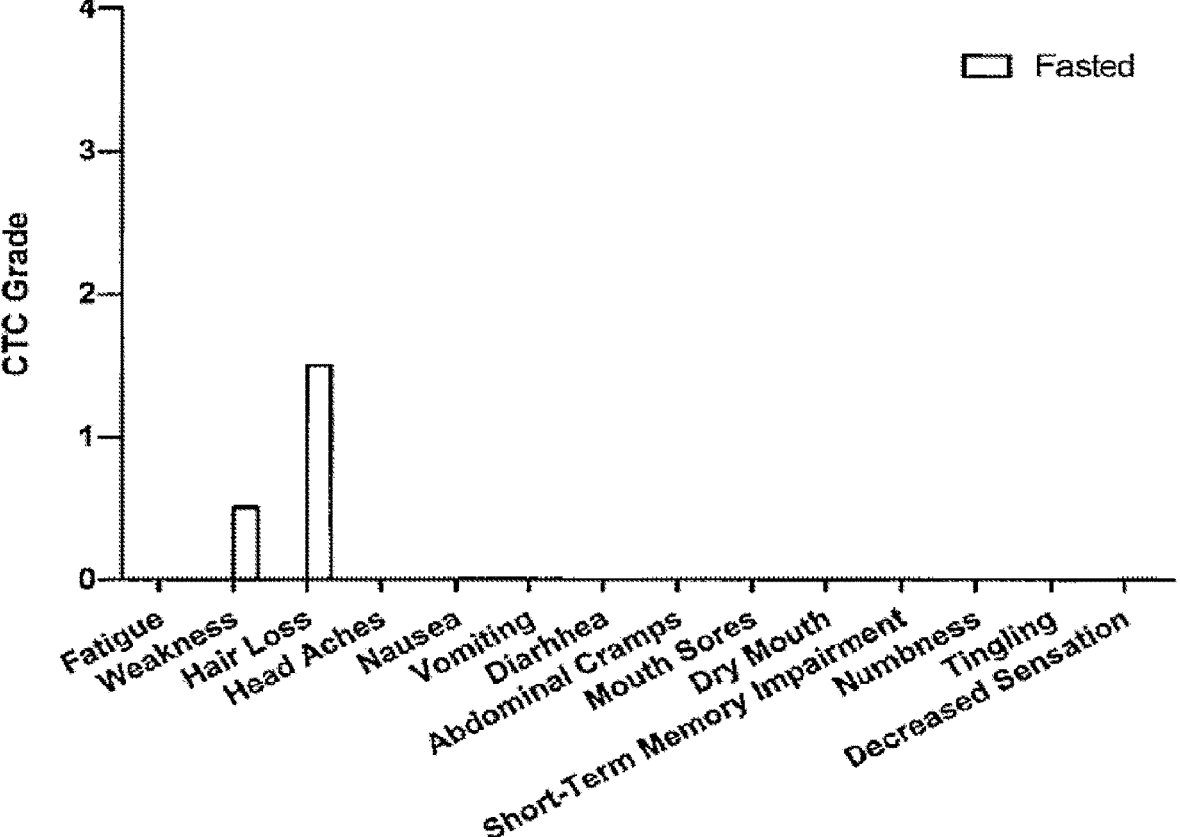
Figures 15E, 15F, 15G:
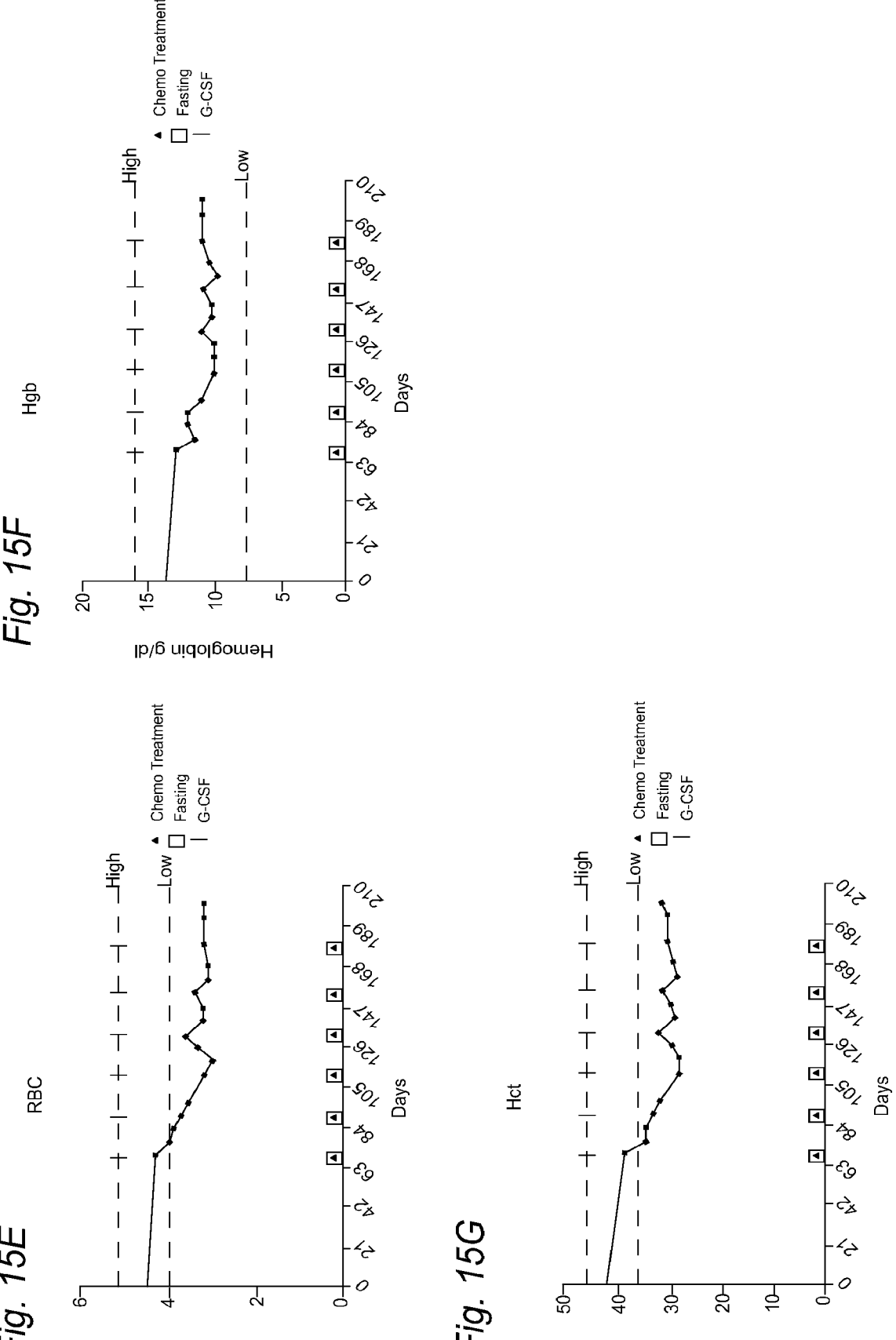
Figure 16:
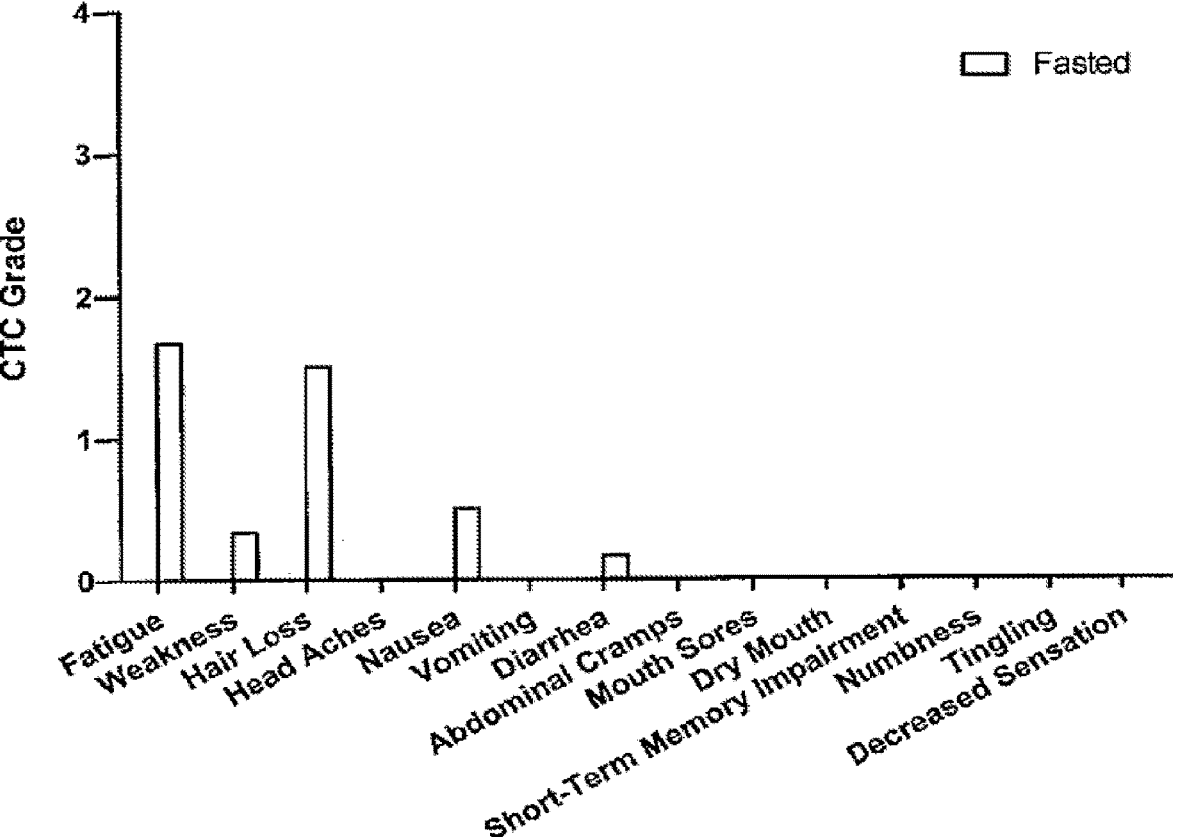
Figures 19A, 19B:
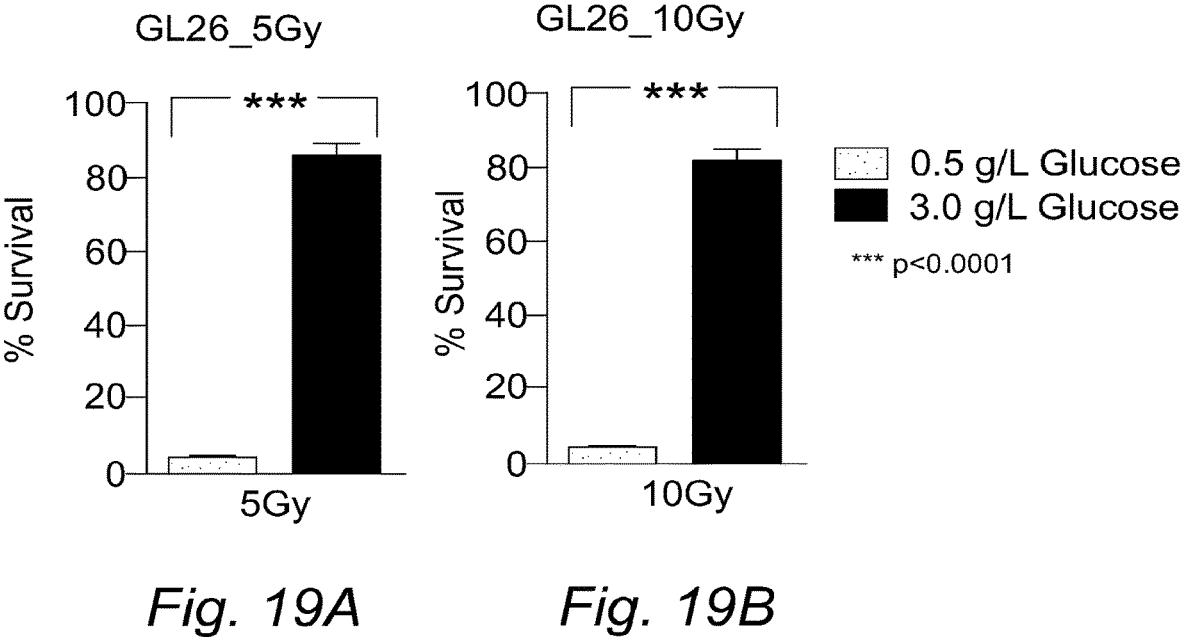
Figure 19C:
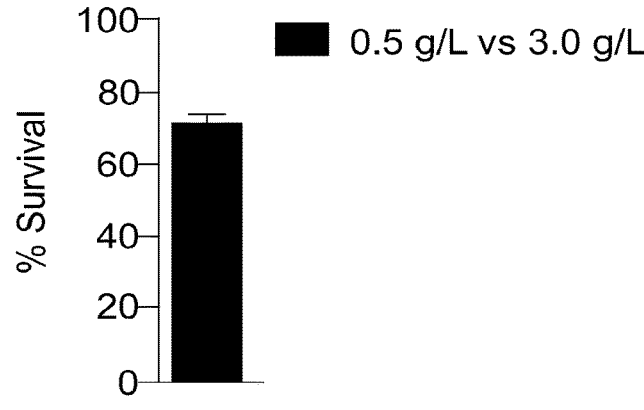
Figure 20:
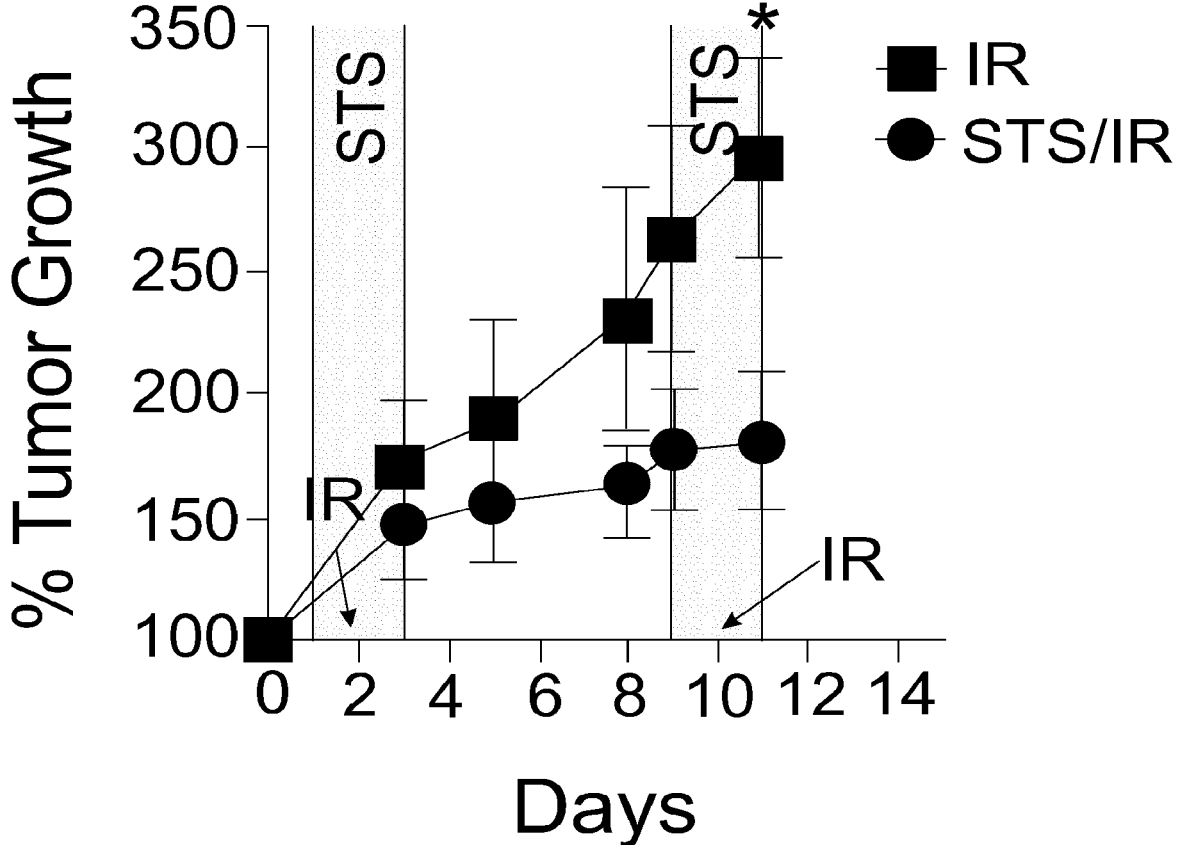
Figure 21:
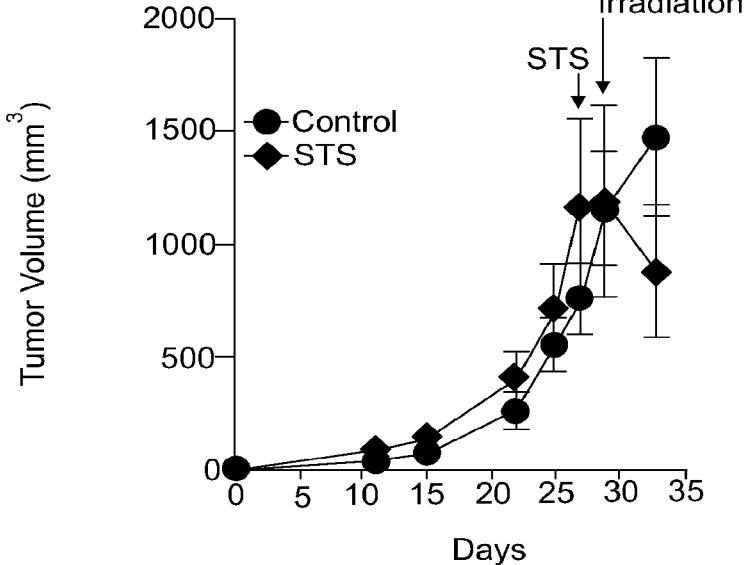
Figures 23A, 23B, 23C, 23D:
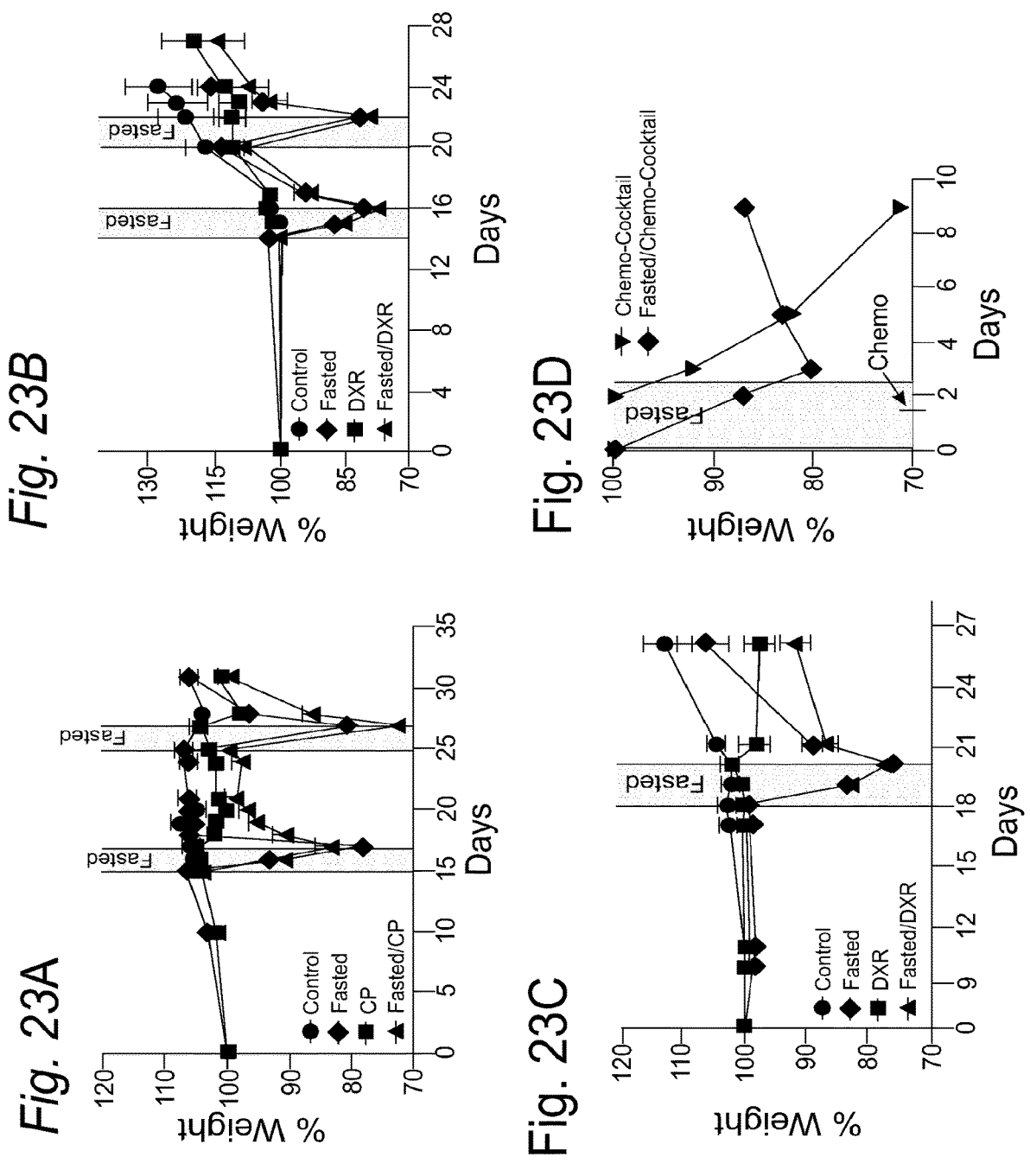
Figure 24:
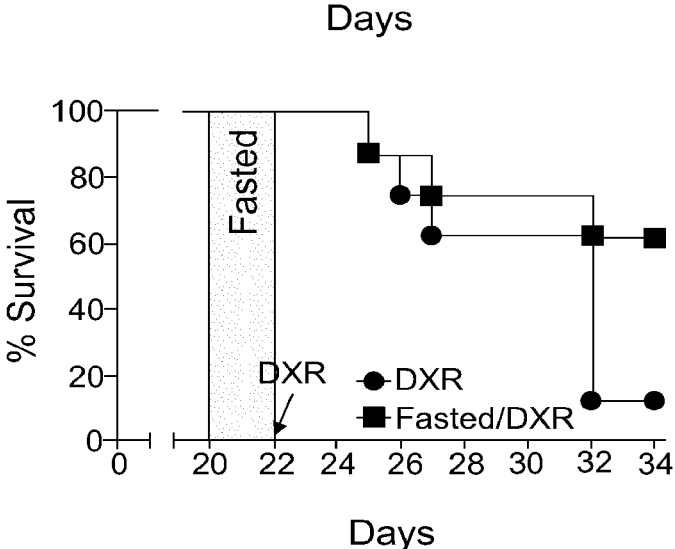
Figure 25:
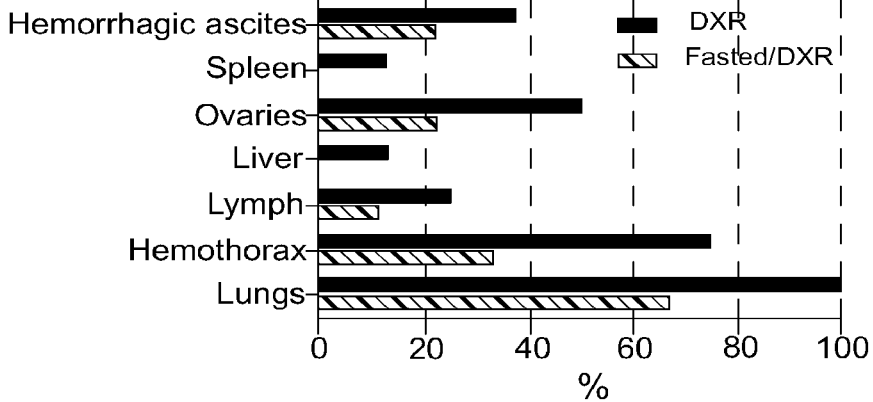
Figure 26:
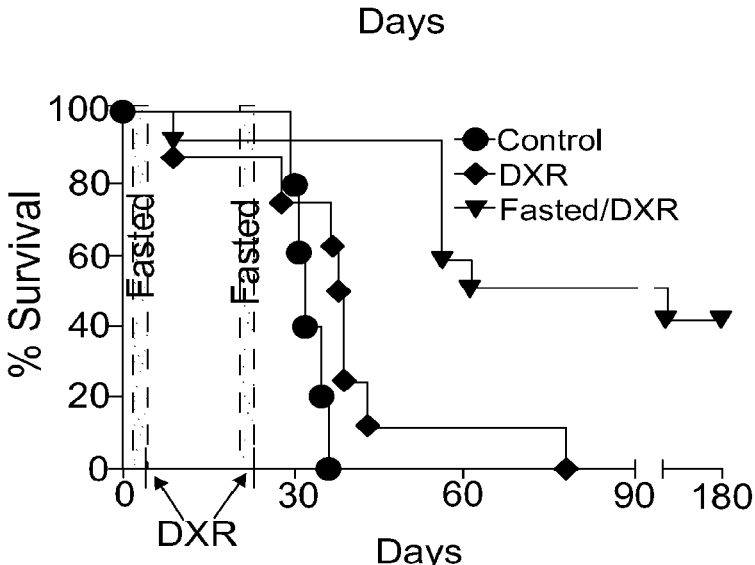
Figure 27:
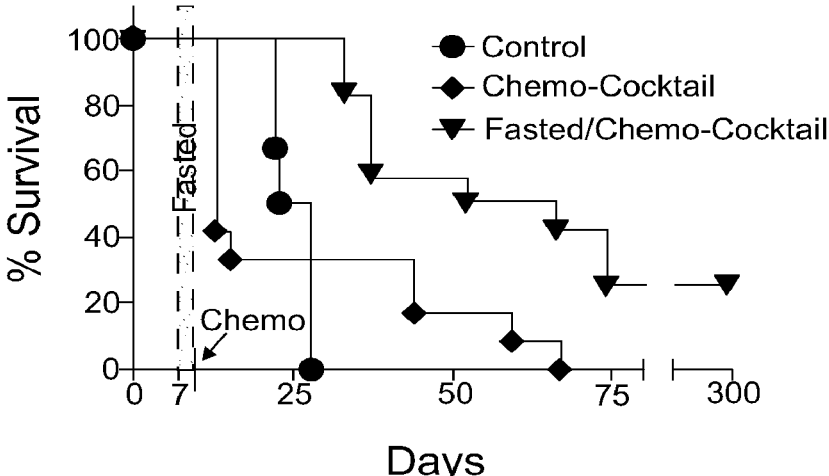
Figure 28:
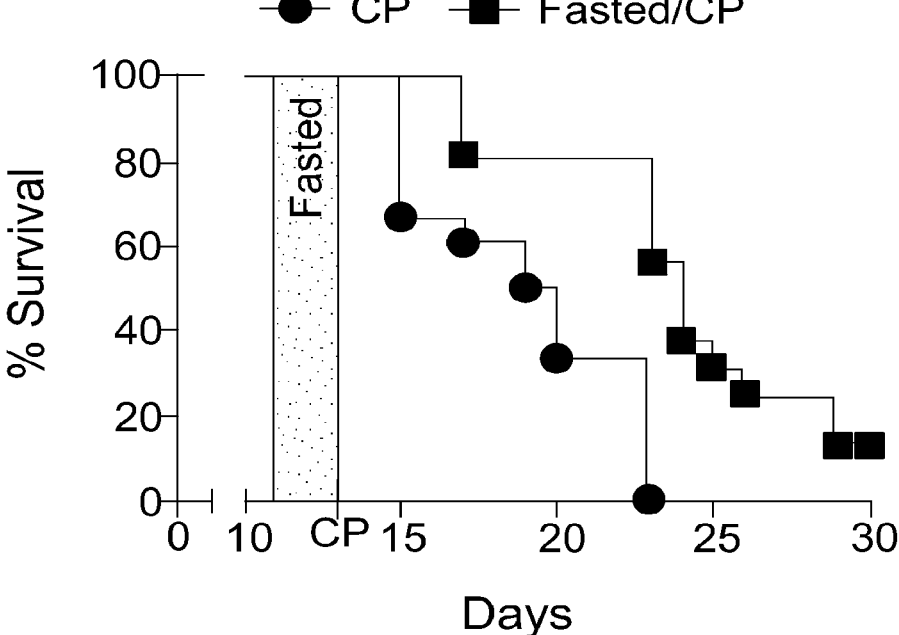
Figure 29:
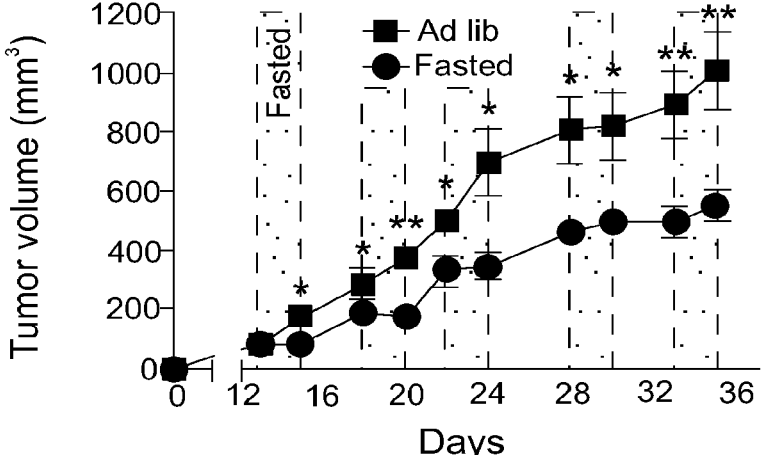
Figure 30:
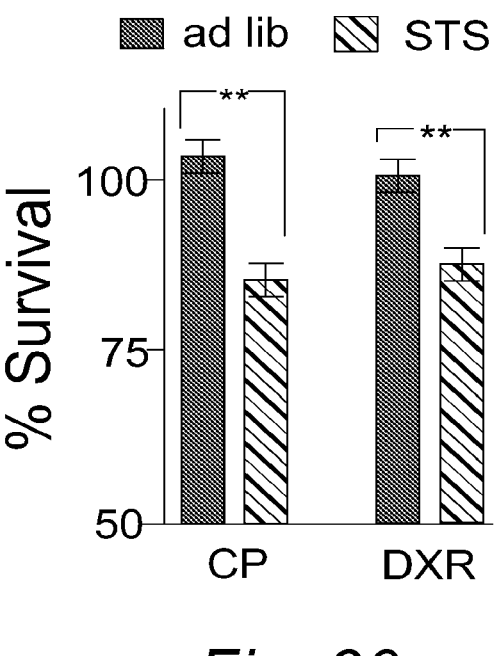
Figure 31:
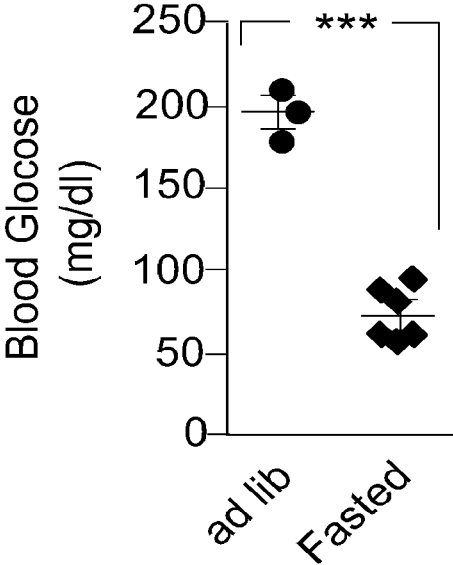
Figure 32:
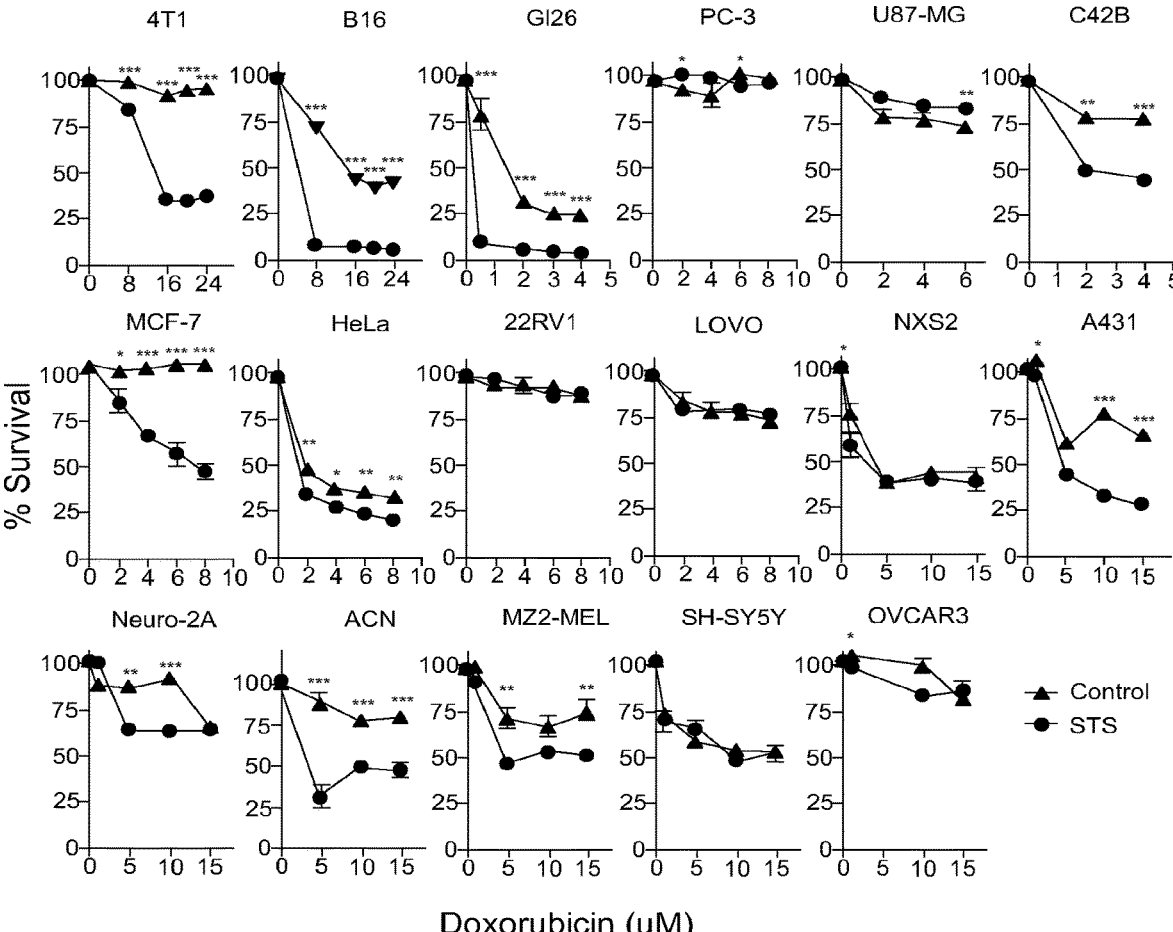
Figure 33:
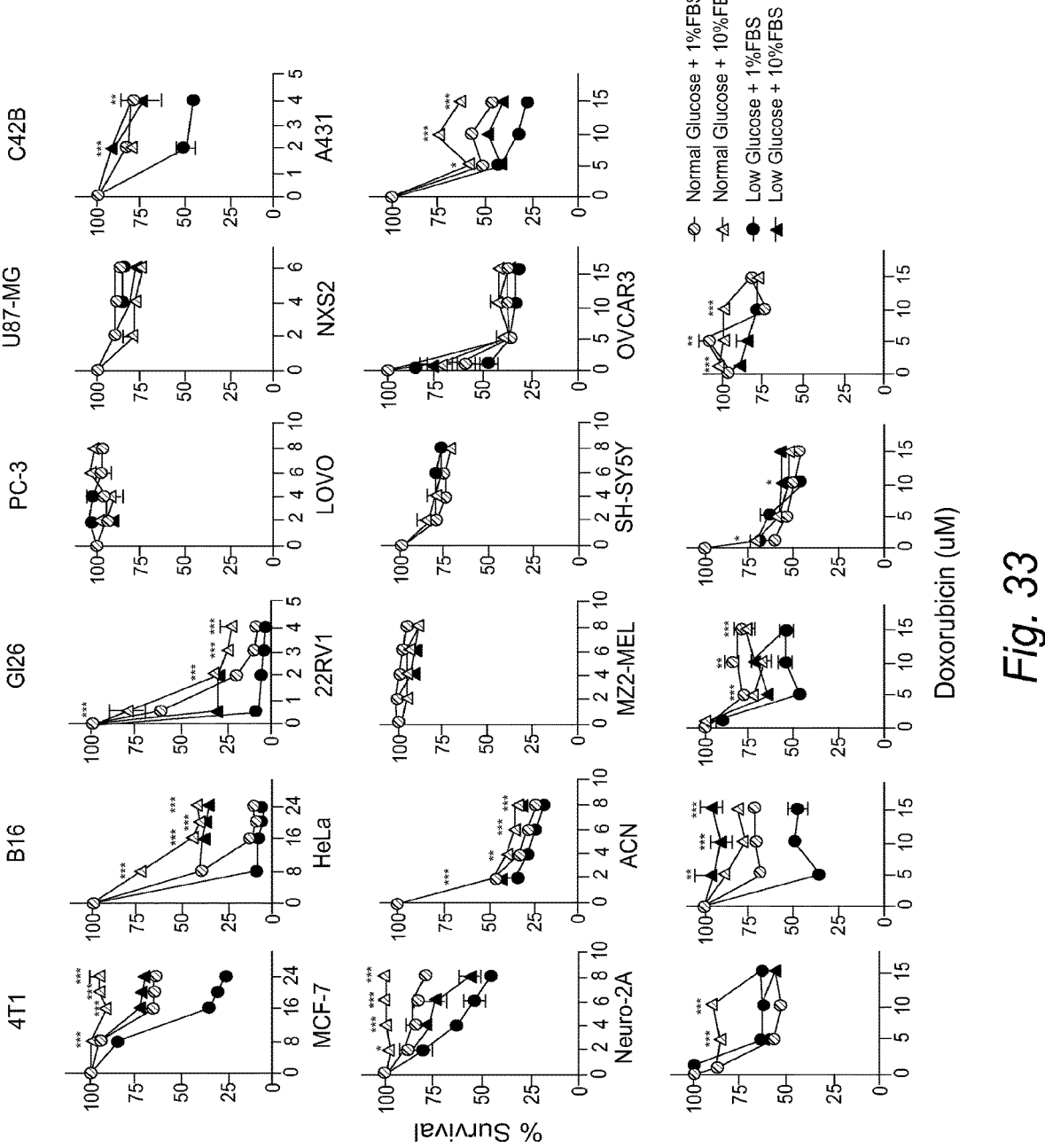
Figure 34:
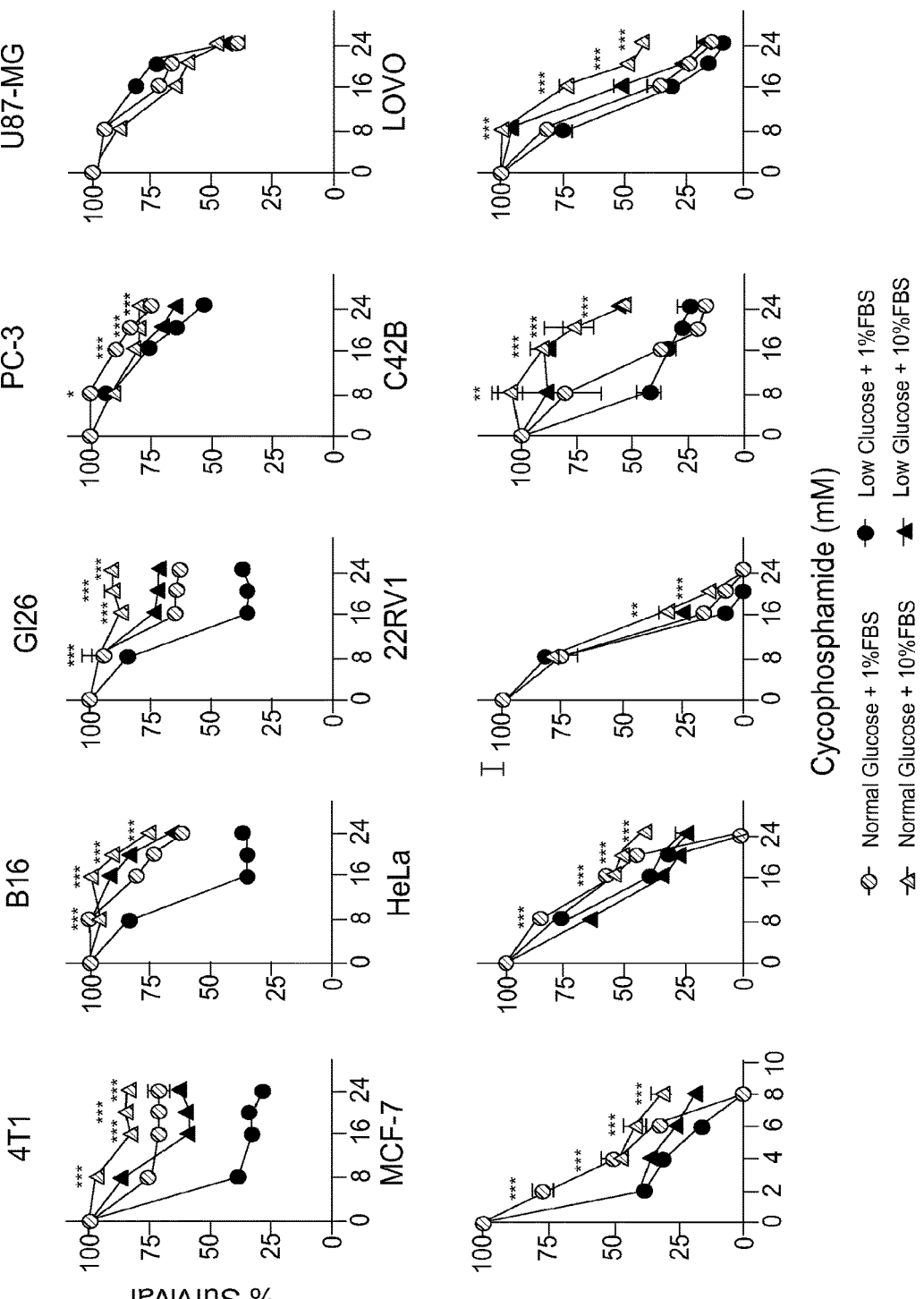
Figure 35:
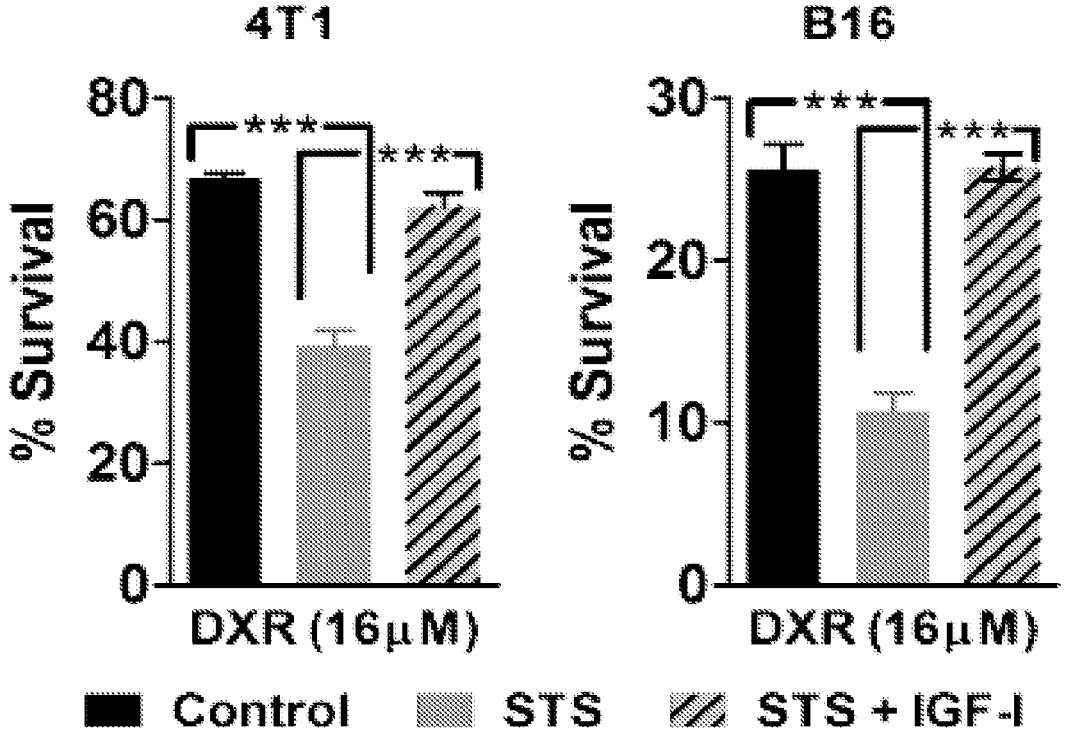
Figures 36A, 36B, 36C:
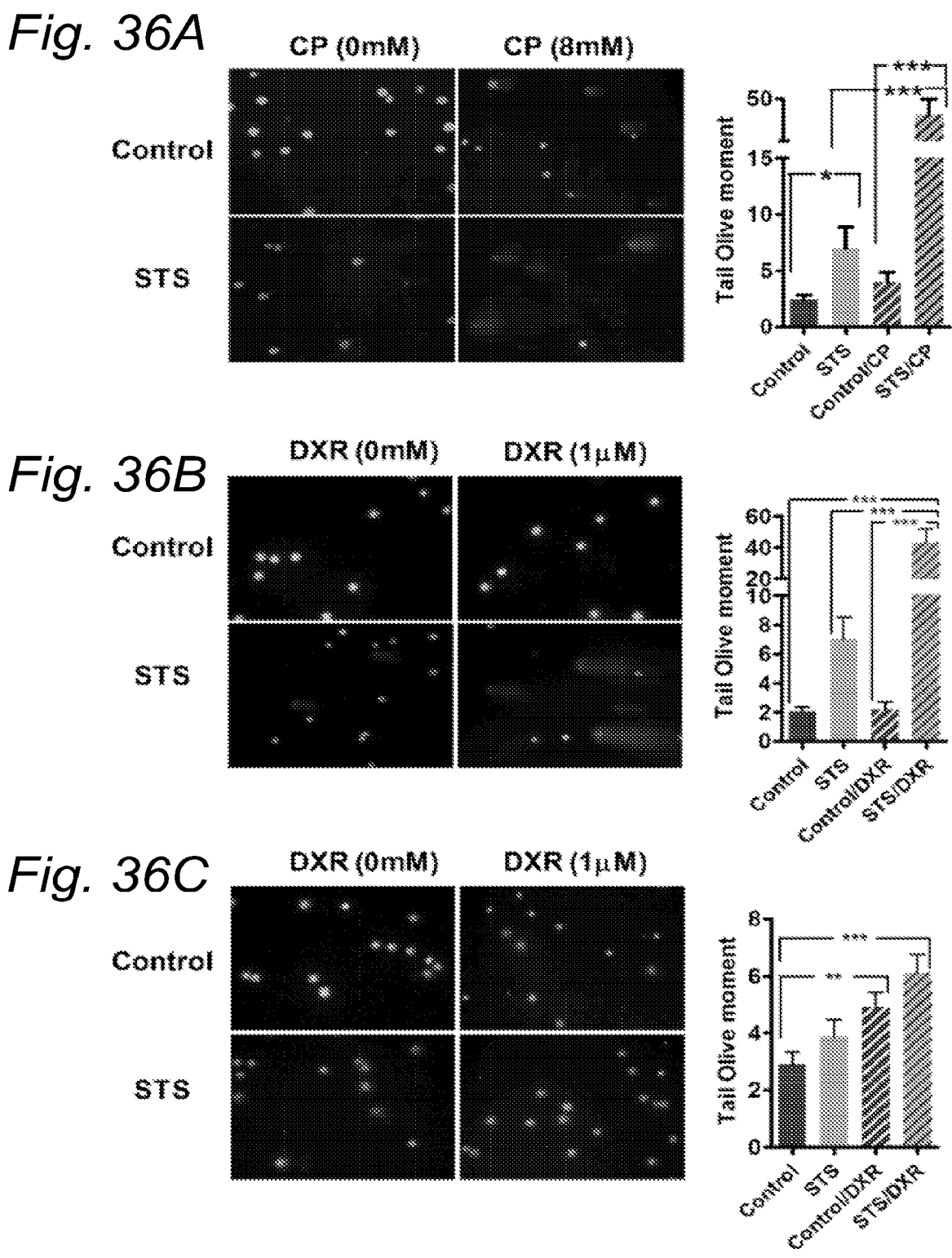
Figure 37:
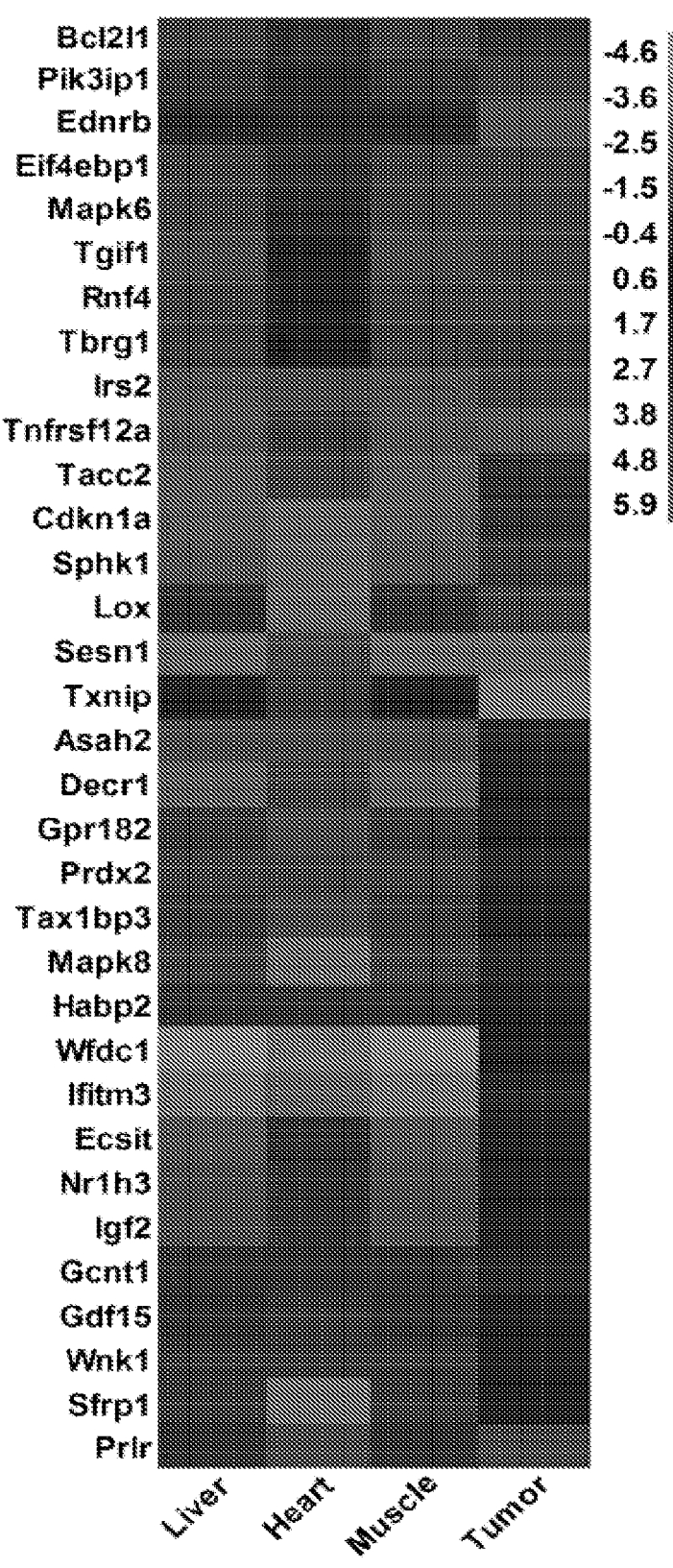
Figure 40:
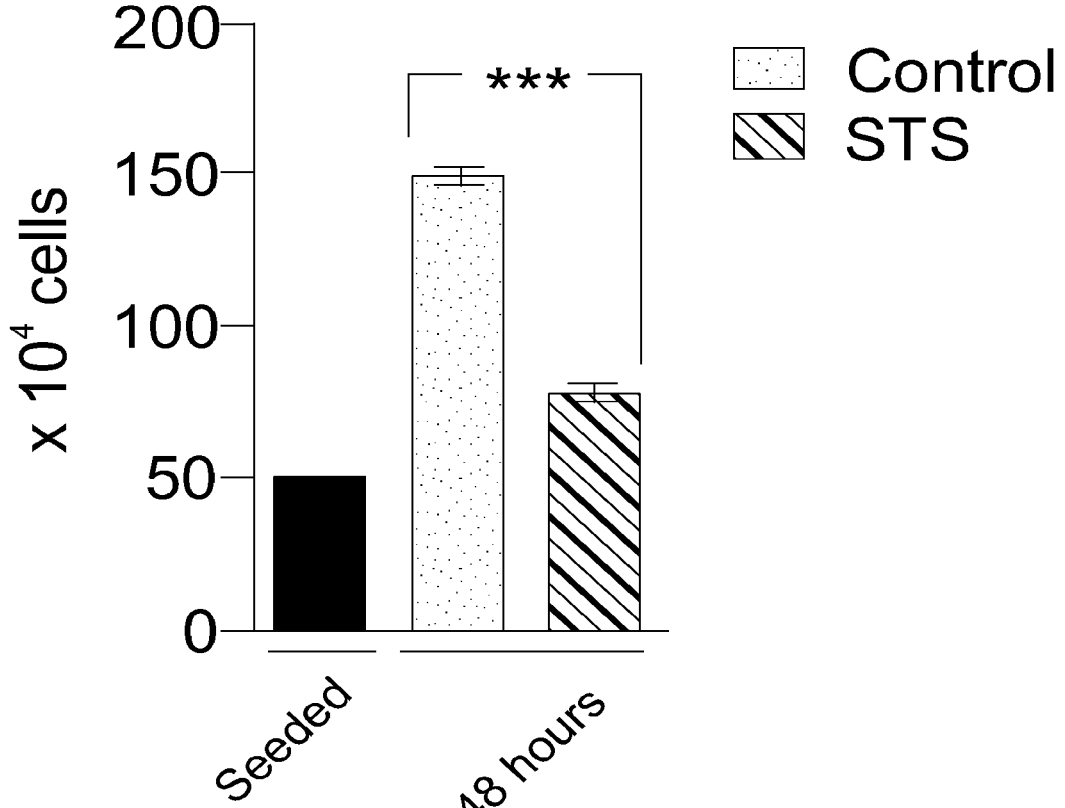
Figure 41:
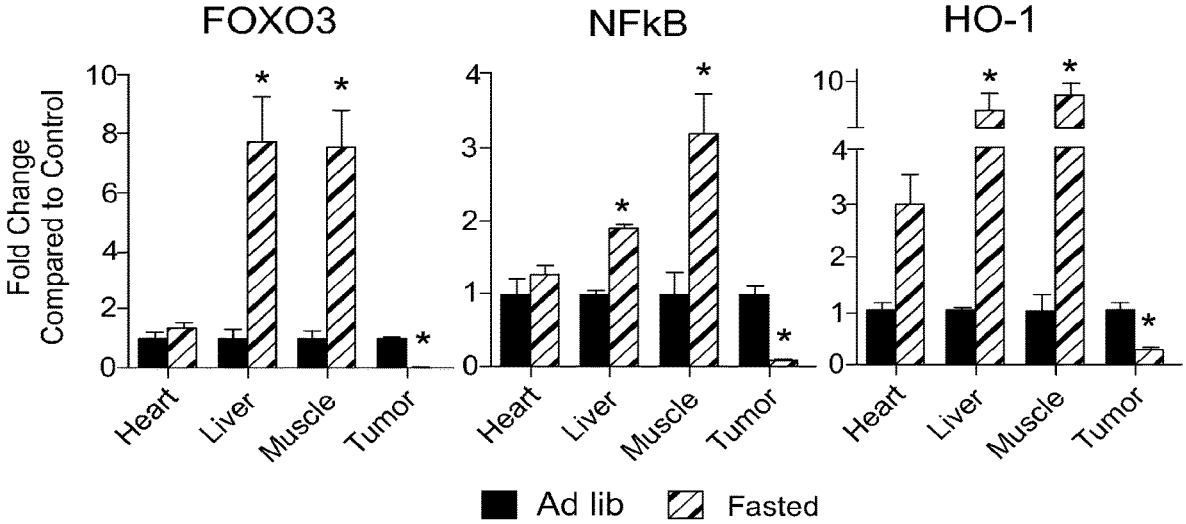
Figure 42:
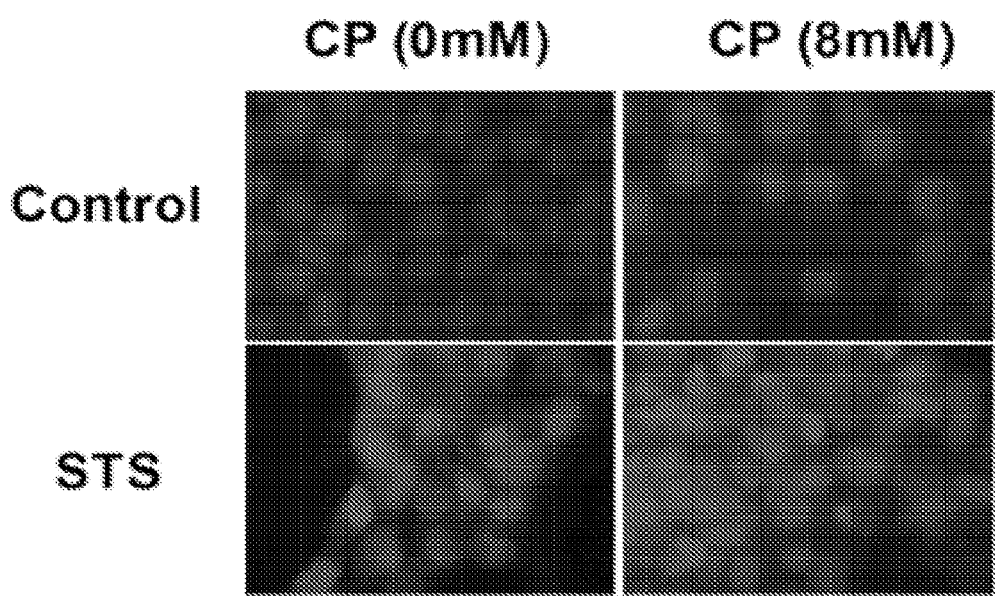
Figure 43:
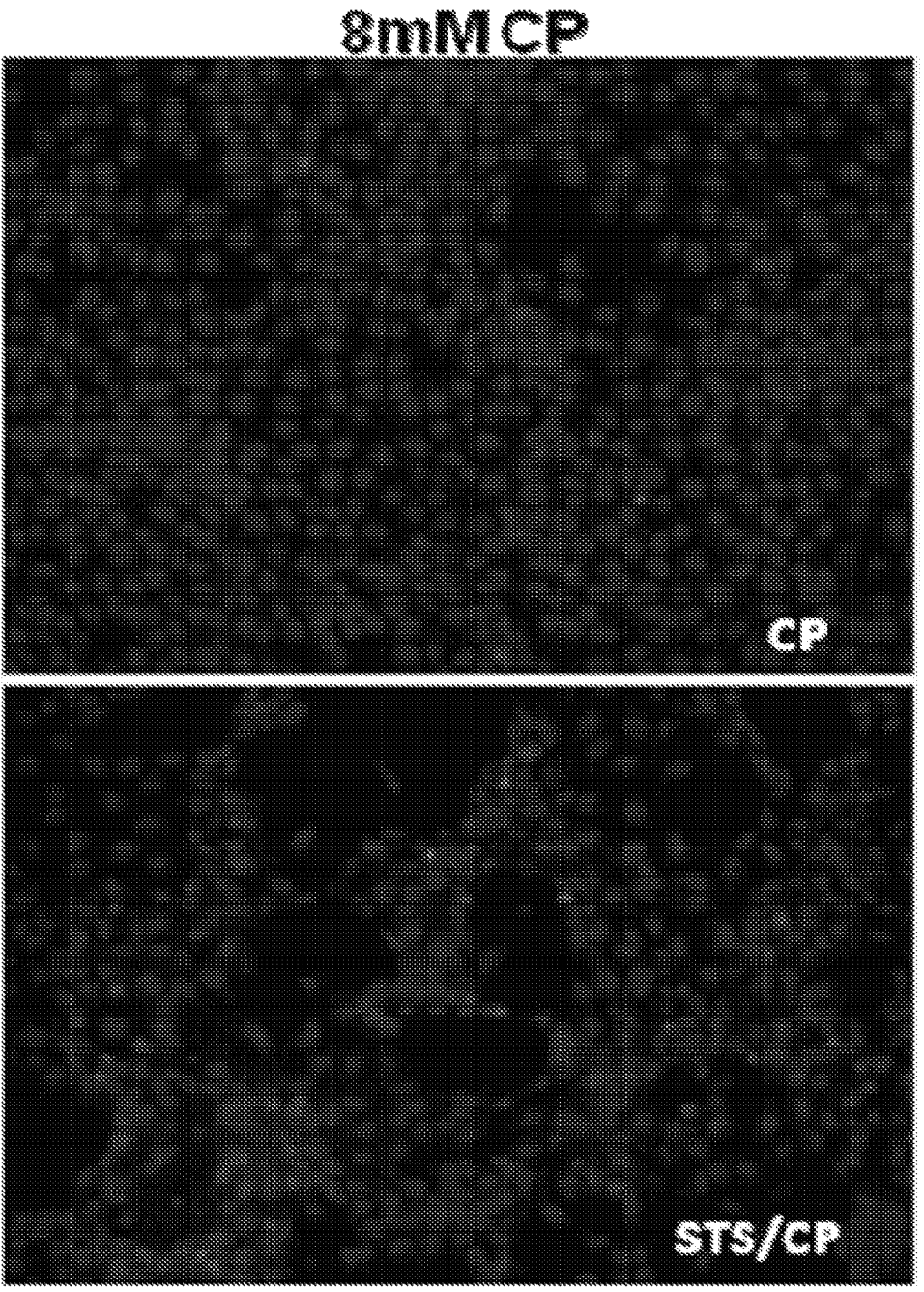
Figure 44A:
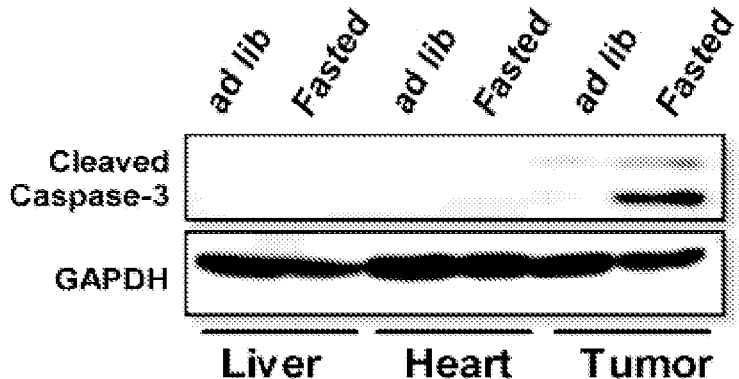
Figure 44B:
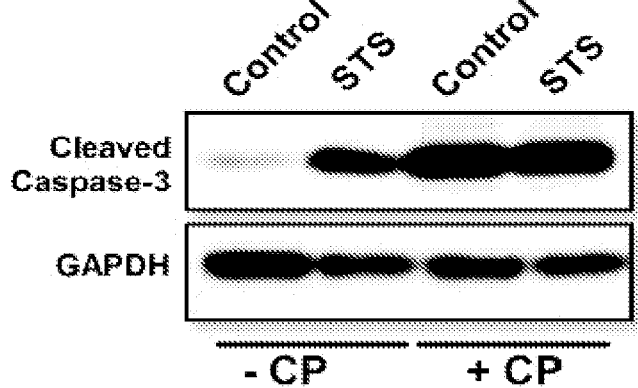
Figure 45:
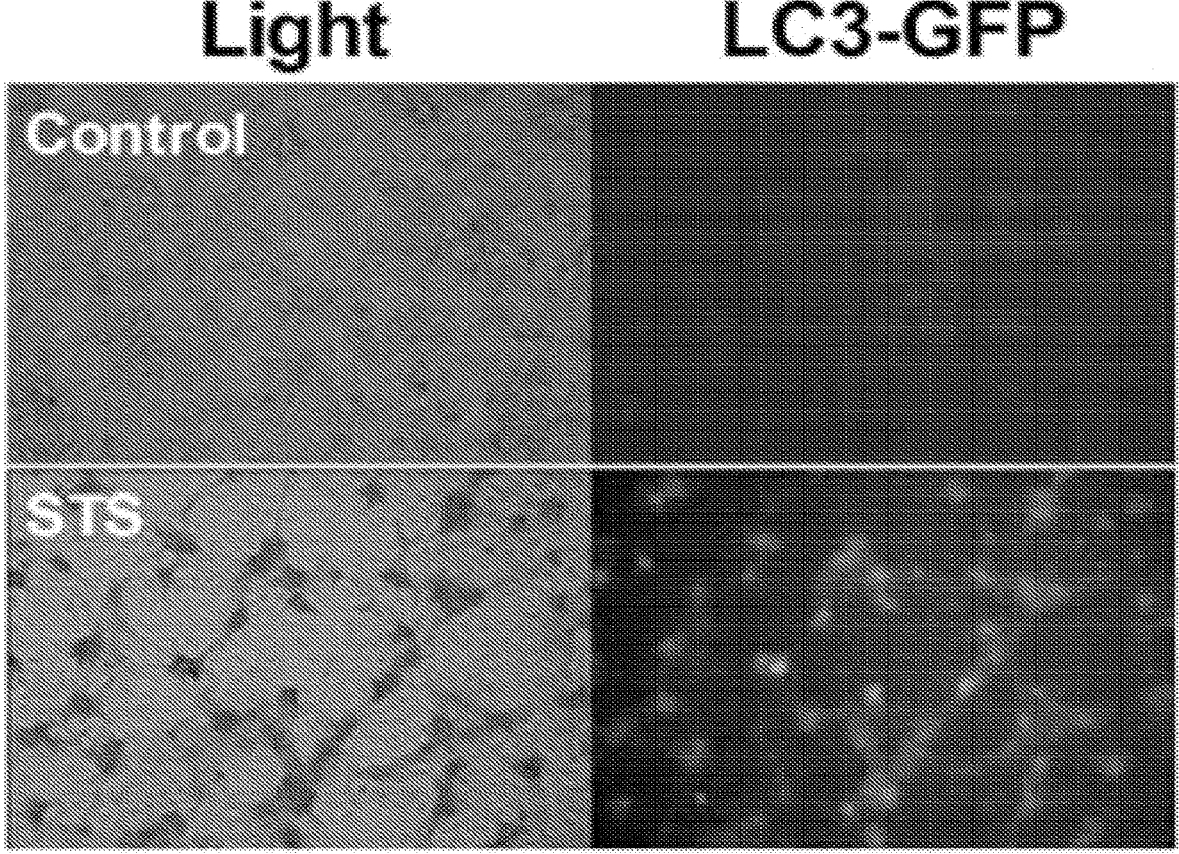
Figure 46:
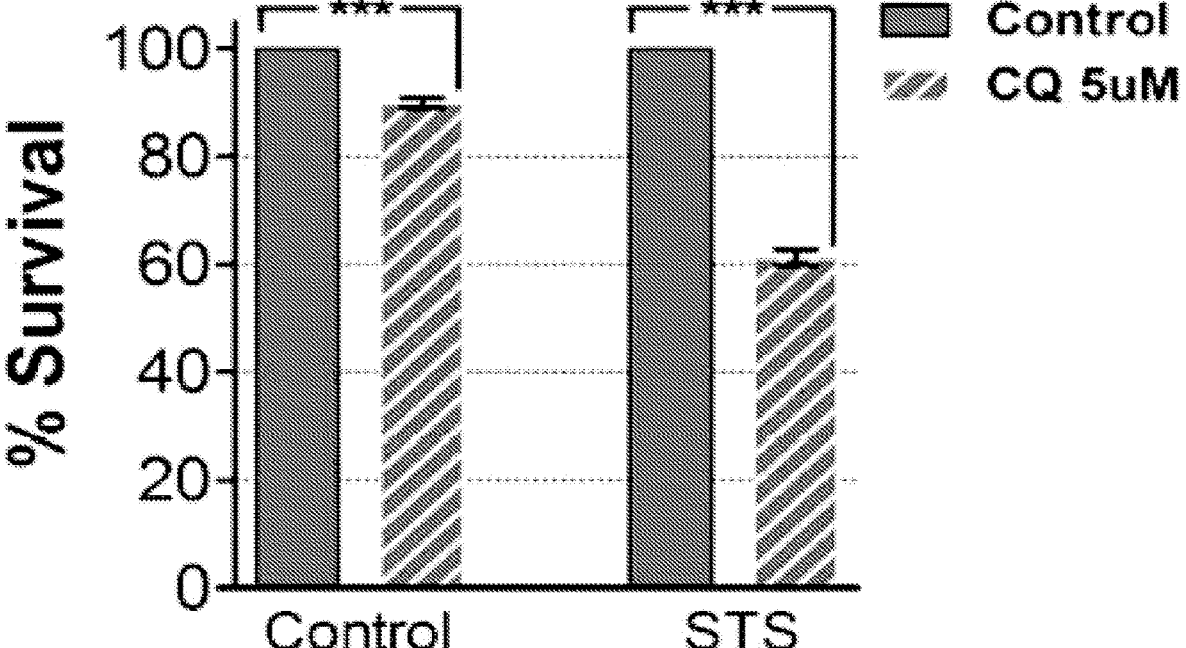
Figure 47:
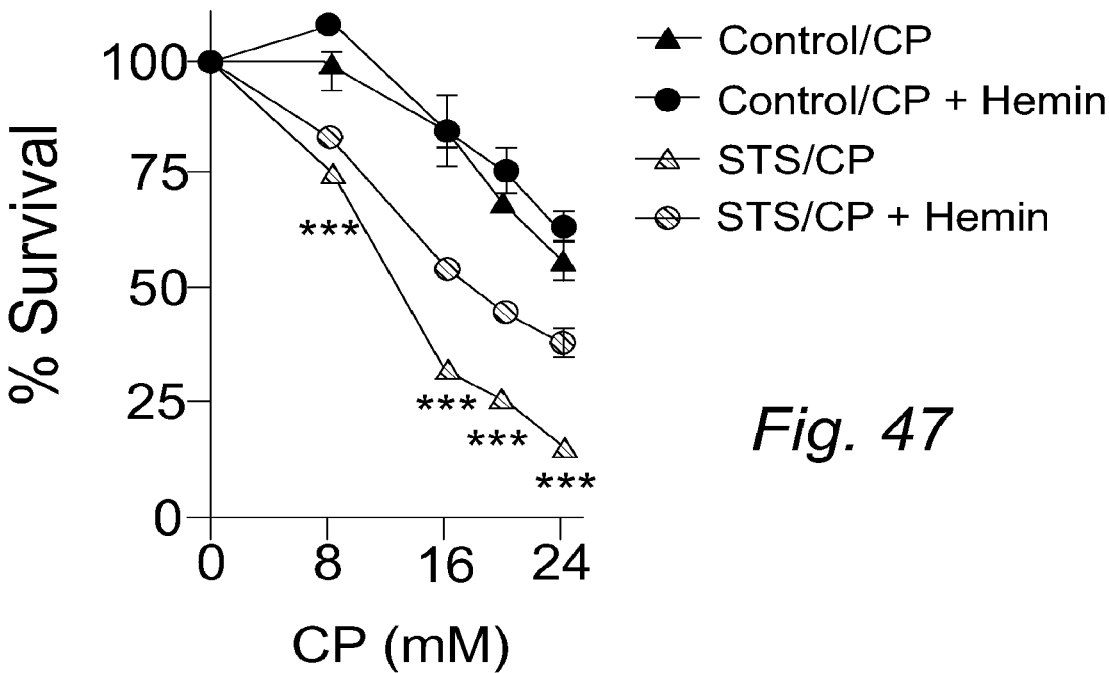
Figure 48:
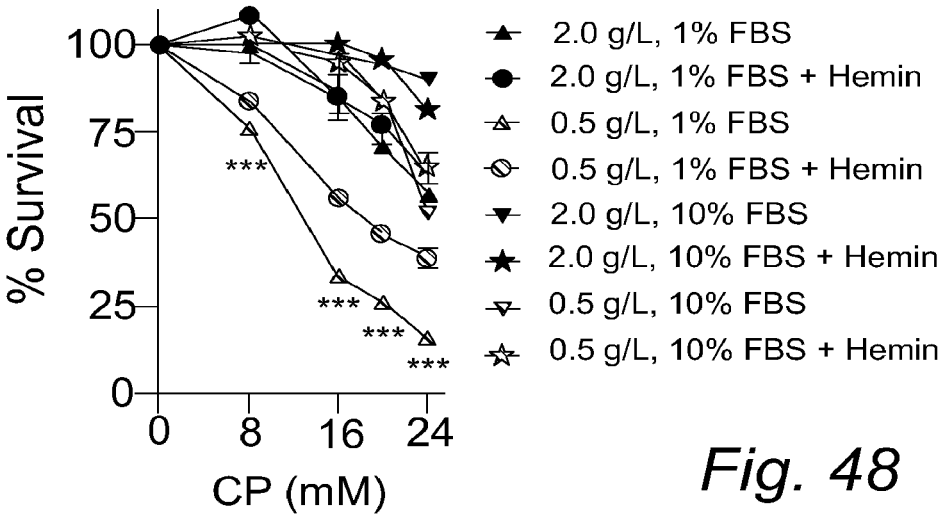
Figure 49:
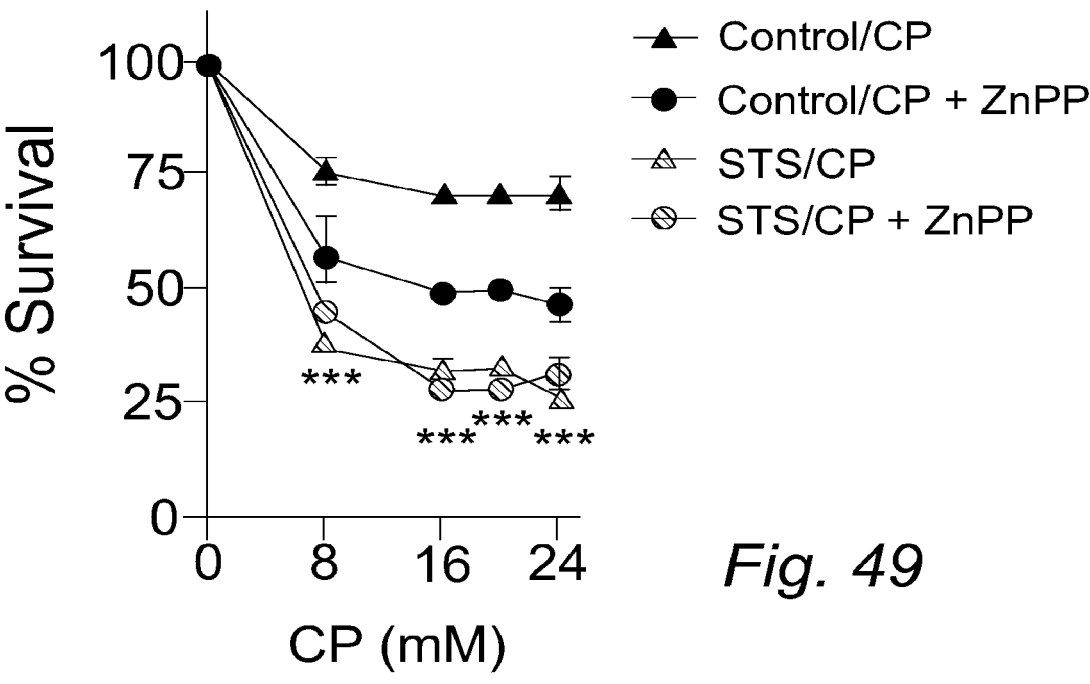
Figure 50:
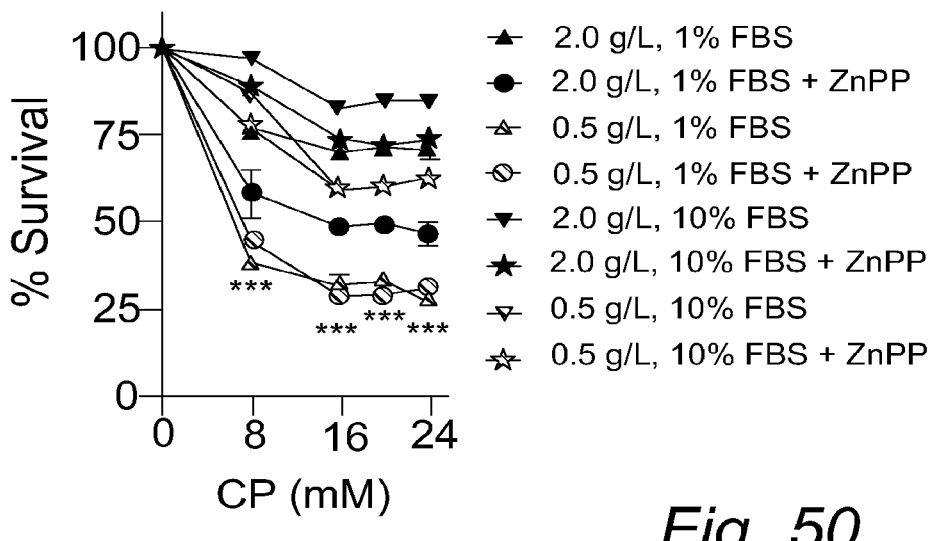
Figure 51:
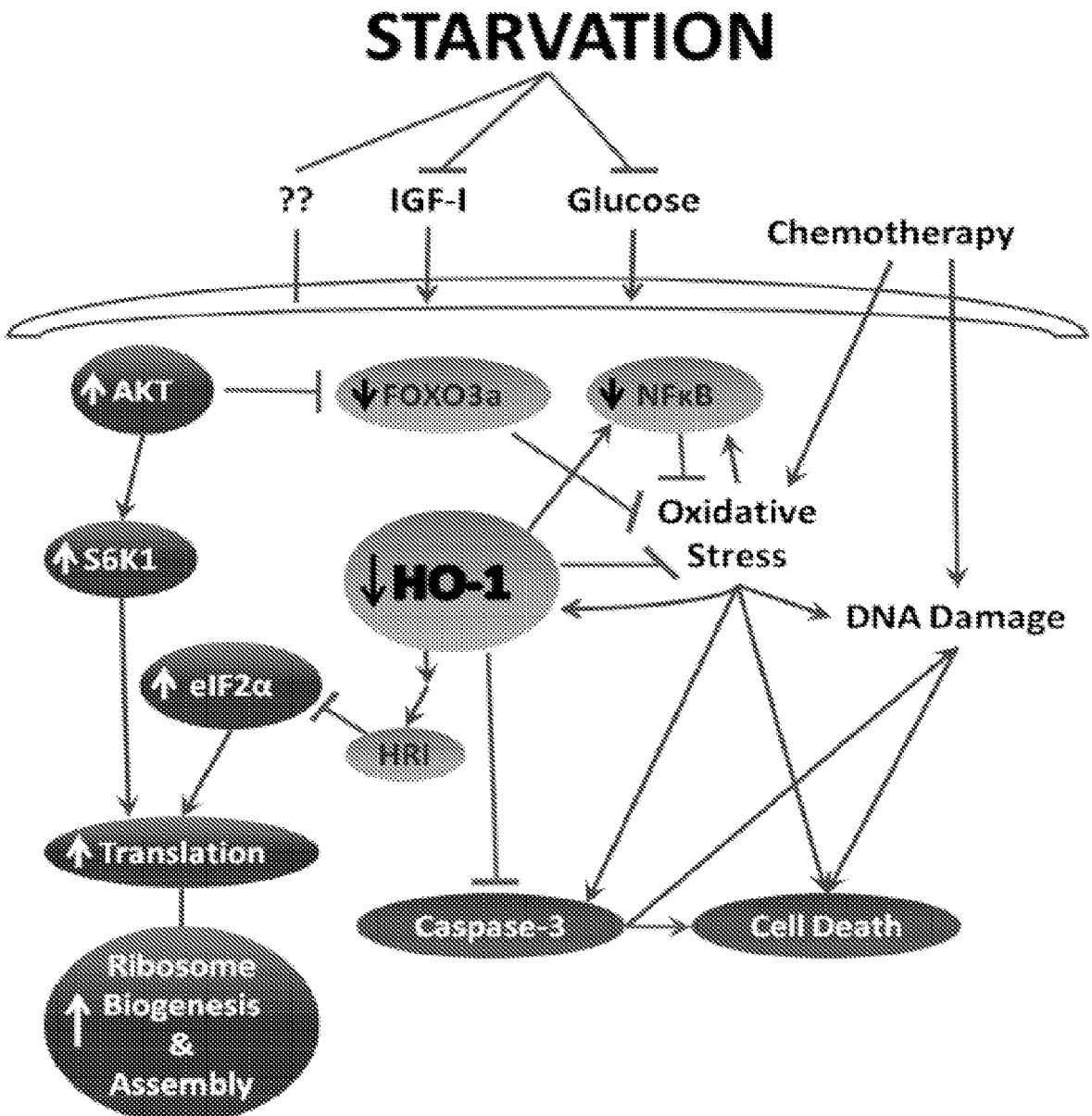
Figure 52:
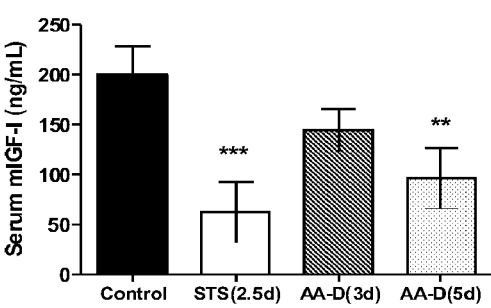
Figure 53:
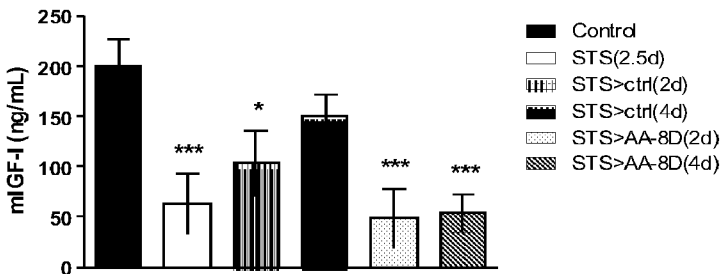
Figure 54A:
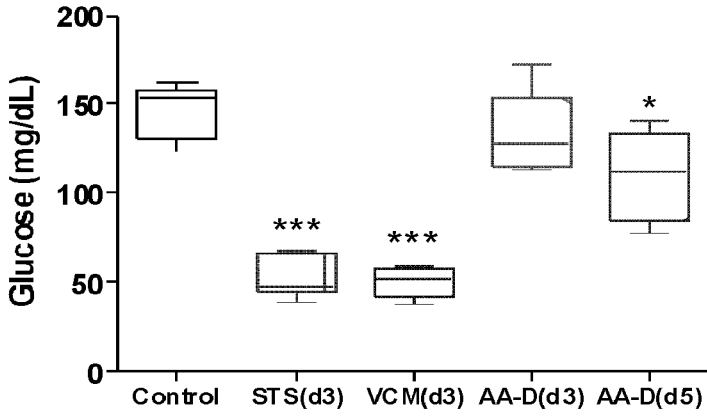
Figure 54B:
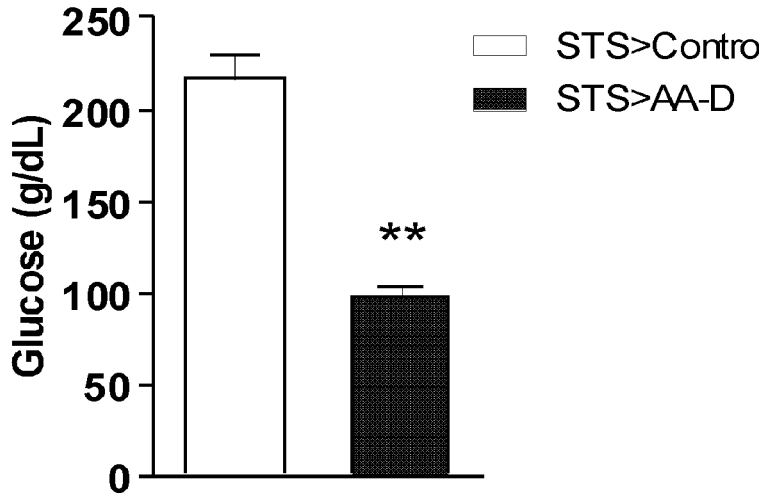
Figure 55A:
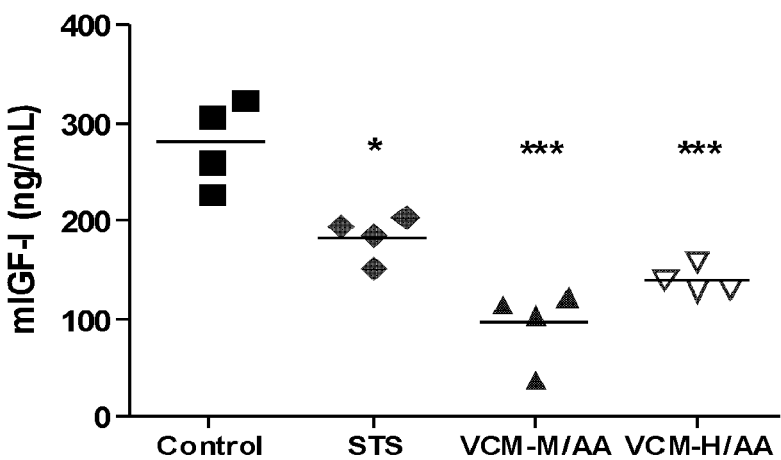
Figure 55B:
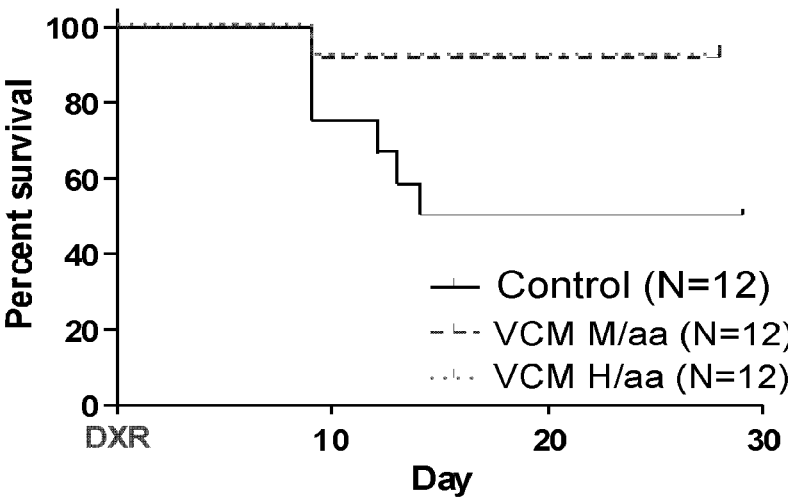
Figure 56A:
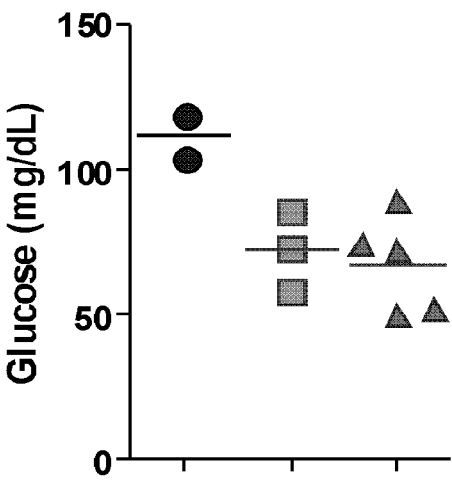
Figure 56B:
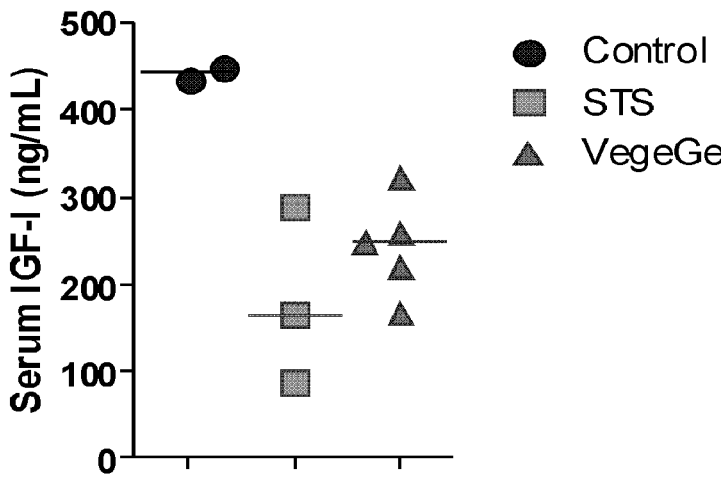
Figure 57A:
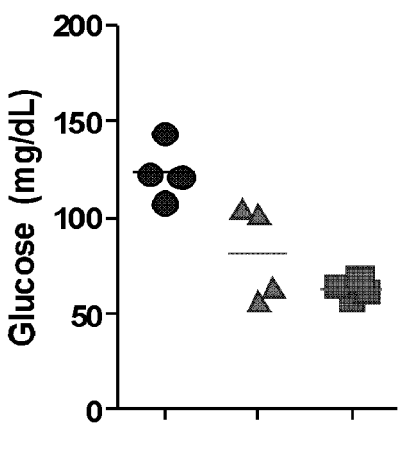
Figure 57B:
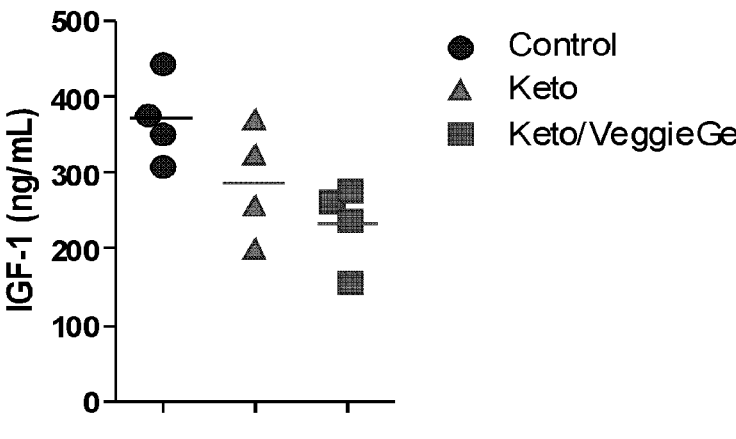

Body weight, filled triangle indicates day of chemotherapy; open square indicates fasting, normal ranges of laboratory values are indicated by dash lines;

FIG. 2 is a bar chart providing self-reported side-effects after chemotherapy for case 1, data represents the average of 2 cycles of chemo-alone Vs the average of 2 cycles of chemo-fasting treatments;

FIG. 3 is a bar chart providing self-reported side-effects after chemotherapy for case 2, data represents the average of 3 cycles of chemo-alone Vs the average of 5 cycles of chemo-fasting treatments;

FIGS. 4A-4H provide plots of laboratory values of blood cell counts for case 3: (A) Neutrophils; (B) Lymphocytes; (C) White blood cells, WBC; (D) Platelets; (E) Red blood cells, RBC (F) Hemoglobin, Hgb; (G) Hematocrit, Hct; (H) Prostate specific antigen (PSA) level, the patient was enrolled in abiraterone acetate (CYP17 inhibitor) trial for 90 days indicated by vertical dash lines, the patient also received G-CSF (Neulasta) on the day of chemotherapy except during the treatment with abiraterone acetate, filled triangle indicates day of chemotherapy; open square indicates fasting, arrow indicates testosterone application (cream 1%), normal ranges of laboratory values are indicated by horizontal dash lines;

FIG. 5 is a bar chart of self-reported side-effects after chemotherapy for case 3, data represent the average of 5 cycles of chemo-alone VS the average of 7 cycles of chemo-fasting treatments;

FIGS. 6A-6G provide plots of laboratory values of blood cell counts for case 4: (A) Neutrophils; (B) Lymphocytes; (C) White blood cells, WBC; (D) Platelets; (E) Red blood cells, RBC (F) Hemoglobin, Hgb; (G) Hematocrit, Het; filled triangle indicates day of chemotherapy; open square indicates fasting, normal ranges of laboratory values are indicated by dash lines;

FIG. 7 is a bar chart of self-reported side-effects after chemotherapy for case 4, data represent the average of 5 cycles of chemo-alone VS 1 cycle of chemo-fasting treatment;

FIG. 8 is a bar chart of self-reported side-effects after chemotherapy for case 5, data represent 1 cycle of chemo-therapy-alone (1$^{st}$ cycle) VS the average of 5 cycles of chemo-fasting treatments;

FIGS. 9A-9G provide plots of laboratory values of blood cell counts for case 6: (A) Neutrophils; (B) Lymphocytes; (C) White blood cells, WBC; (D) Platelets; (E) Red blood cells, RBC (F) Hemoglobin, Hgb; (G) Hematocrit, Hct; filled triangle indicates day of chemotherapy; open square indicates fasting, normal ranges of laboratory values are indicate by dash lines, the patient received red blood cell transfusion (3 units) on day 71 and also received G-CSF (Neulasta) as indicated;

FIG. 10 is a bar chart of self-reported side-effects after chemotherapy for case 6;

FIGS. 11A-11H provide plots of laboratory values of blood cell counts for case 7: (A) Neutrophils; (B) Lymphocytes; (C) White blood cells, WBC; (D) Platelets; (E) Red blood cells, RBC (F) Hemoglobin, Hgb; (G) Hematocrit, Hct; (H) Prostate specific antigen (PSA) level, filled triangle indicates day of chemotherapy; open square indicates fasting, arrow indicates abiraterone administration, normal ranges of laboratory values are indicate by dash lines, the patient also received G-CSF Neulasta) as indicated;

FIG. 12 is a bar chart of self-reported side-effects after chemotherapy for case 7, data represent the average of 8 cycles of chemo-fasting treatments;

FIG. 13 is a bar chart of self-reported side-effects after chemotherapy for case 8, data represent the average of 4 cycles of chemo-fasting treatments;

FIG. 14 is a bar chart of self-reported side-effects after chemotherapy for case 9, data represent the average of 4 cycles of chemo-fasting treatments;

Figures 15A, 15B, 15C, 15D:
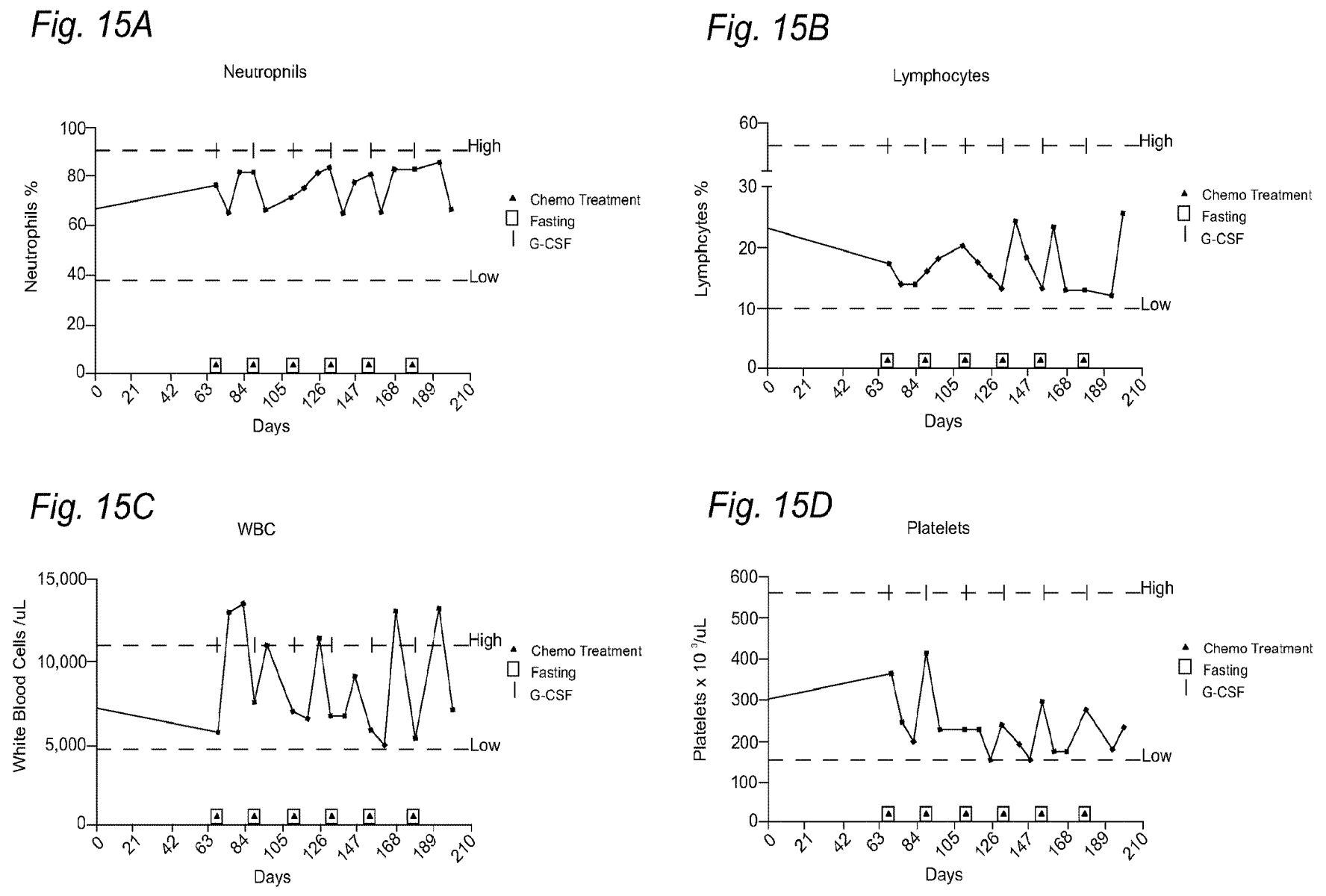

FIGS. 15A-15G provide plots of laboratory values of blood cell counts for case 10: (A) Neutrophils; (B) Lymphocytes; (C) White blood cells, WBC; (D) Platelets; (E) Red blood cells, RBC (F) Hemoglobin, Hgb; (G) Hematocrit, Hct; (G) Hematocrit, Hct, filled triangle indicates day of chemotherapy; open square indicates fasting, normal ranges of laboratory values are indicated by dash lines, the patient also received G-CSF (Neulasta) as indicated;

FIG. 16 is a bar chart of self-reported side-effects after chemotherapy for case 10, data represent the average of 6 cycles of chemo-fasting treatments;

FIGS. 17A-17B are bar charts of self-reported side-effects after chemotherapy with or without fasting. (A) Data represent average of CTC grade reported by all the patients in this study; 18 chemotherapy cycles under ad-lib diet were compared to 46 chemo-fasting cycles; (B) Data represent average of CTC grade from matching fasting and non-fasting cycles; 6 patients received either chemo-alone or chemofasting treatments, self-reported side effects from the closest two cycles were compared one another, statistical analysis was performed only from matching cycles, and data presented as standard error of the mean (SEM), P value was calculated with unpaired, two tail t test (*, P<0.05);

FIGS. 18A-18C are bar charts showing the results of an experiment in which murine breast (4T1-luc) cells were plated in 96-well cell culture plates (20,000/well), and allowed to equilibrate and reach confluency for 48 hours, media was then switched to either low or high glucose media for 48 hours prior to irradiation (5 or 10Gy; FIGS. 18A, 18B), viability was determined by the MTT assay (FIG. 18C), and statistical analysis was done by the Student's t-test (N=60);

FIGS. 19A-19C are bar charts showing the results of an experiment in which murine glioma (GL26) cells were plated in 96-well cell culture plates (20,000/well), and allowed to equilibrate and reach confluency for 48 hours, media was then switched to either low or high glucose media for 48 hours prior to irradiation (5 or 10Gy; FIGS. 19A, 19B), viability was determined by the MTT assay (FIG. 19C), and statistical analysis was done by the Student's t-test (N=60);

FIG. 20 provides plots of an experiment in which female BALB/c mice weighing 20-25 g were subcutaneously injected with syngeneic breast cancer cells (4T1-luc; $2\times10^5$ cells/mouse), on day 13 the tumor progressed significantly to 300-500 mm$^3$, and treatment began by fasting the mice for 48 hours prior to irradiation (1R; 5Gy), the second cycle of STS/IR (3Gy) was done 1 week later, and statistical analysis was done using Student's test for each day, *p<0.05;

FIG. 21 provides plots of an experiment in which female C57BL/6 mice weighing 25-30 g were subcutaneously injected with syngeneic glioma cancer cells (GL26; $3\times10^5$ cells/mouse), on day 27 the tumor progressed significantly to 500-1000 mm$^3$, and treatment began by fasting the mice for 48 hours prior to irradiation (IR; 7.5Gy), the second cycle of STS/IR (3Gy) was done 1 week later, and statistical analysis was done using Student's test for each day, *p<0.05;

FIGS. 22A-22C provide plots showing that fasting sensitizes tumors to chemotherapy; in particular, subcutaneous tumor progression of murine (A) breast cancer (4T1), (B)

melanoma (B16), and (C) glioma (GL26) is shown as percent growth together with the tumor size immediately before and after each 48-hour fasting cycle;

FIGS. 23A-23D provide plots showing that body weight lost during 48-60 hours of fasting was readily recovered after resuming normal feeding in (A-C) subcutaneous and (D) metastatic mouse models of cancer: (A) murine breast (4T1) cancer-bearing BALB/c mice, (B) murine melanoma (B16)- and (C) glioma (GL26)-bearing C57BL mice, and (D) murine neuroblastoma (Neuro-2a)-bearing A/J mice;

FIG. 24 provides plots showing that 24-48 hours of fasting enhanced the survival of metastatic murine melanoma (B16);

FIG. 25 is a bar chart showing metastasis of B16 melanoma cells to different organs compared to mice that received DXR under normal feeding;

FIG. 26 provides plots showing that fasting also sensitized tumors in 2 metastatic models of murine neuroblastoma: NXS2 (P<0.001) resulting in long-term survival;

FIG. 27 provides plots showing that fasting also sensitized tumors in 2 metastatic models of murine neuroblastoma: Neuro-2a (P=0.005)resulting in long-term survival;

FIG. 28 provides plots showing that fasting sensitized cancer cells to chemotherapy in metastatic mourse model of breast cancer (4T1), log-rank test, P<0.0005;

FIG. 29 provides plots showing that fasting retarded tumor progression of xenografted human neuroblastoma (ACN) which was subcutaneously injected into nude mice; once tumors were palpable, fasting was performed for a total of 5 cycles; one-way ANOVA with Tukey's post-test for subcutaneous models (Student's t-test for (B) day 27)), and log-rank test for metastatic models, *P<0.05, P<0.01, *P<0.001;

FIG. 30 provides a bar chart showing that serum from fasted mice sensitized breast cancer cells to doses of DXR and CP that were minimally toxic under serum from mice fed ad lib. Control groups were cultured in 1.0 g/L and 2.0 g/L glucose, for human and murine cells respectively, supplemented with 10% FBS. STS groups were cultured in 0.5 g/L glucose supplemented with 1% FBS. Survival was determined by MTT-reduction. For the effects of all combinations of glucose and serum on DXR and CP, refer to FIGS. 33-34;

FIG. 31 provides a bar chart showing blood glucose levels from fasted mice;

FIG. 32 provides plots showing the results of an experiment that STS sensitized 15 out of 17 different cancer cells to DXRin vitr, STS was applied to 4 murine cancer cells—breast cancer (4T1), melanoma (B16), glioma (GL26), and neuroblastoma (NXS2 and Neuro-2a)—and 13 different human cancer cells—prostate cancer (PC3, 22RV1), breast cancer (MCF-7, C42B), glioblastoma (187-MG), cervical cancer (HeLa), colon cancer (LOVO), neuroblastoma (ACN, SH-SY5Y), epidermoid carcinoma (A431), melanoma (MZ-MEL) and ovarian cancer (OVCAR)—and challenged with DXR;

FIG. 33 provides plots showing the effects of all combinations of glucose and serum on DXR;

FIG. 34 provides plots showing effects of all combinations of glucose and serum on CP;

FIG. 35 provide bar charts showing that IGF-I reverses the STS-dependent sensitization of cancer cells to chemotherapy; murine breast cancer (4T1) and melanoma (1316) cells were treated with rhIGF-I (200 μM) during glucose restriction (0.5 g/L vs 2.0 g/L, under 1% FBS), followed by DXR (16 μM) treatment; Student's t-test; *P<0.05, P<0.01, *P<0.001;

FIGS. 36A-36C provide assay results showing that fasting and regulation of oxidative stress and DNA repair; STS was genotoxic and synergistically increased DNA damage when combined with (A) CP in breast cancer (4T1) and with DXR in (B) melanoma (B16), and (C) glioma (GL26) cells as determined by comet assay. Cells in the control and STS groups were cultured in normal glucose (2.0 g/L) or low glucose (0.5 g/L), respectively, supplemented with 1% FBS. Drugs were selected for consistency with the in vivo studies in FIG. 22 A-C;

FIG. 37 provides results of microarray analysis on subcutaneous breast tumors (4T1) from normally fed or fasted mice show differential regulation of cellular proliferation pathways;

FIG. 38 provides results of microarray analysis on subcutaneous breast tumors (4T1) from normally fed or fasted mice show an increase in translational mechanisms including ribosome assembly/biogenesis;

FIGS. 39A-39B provide assay results showing that fasting increased Akt and S6K and reduced eIF2a phosphorylation, consistent with increased translational components, in murine breast cancer cells (4T1) (A) in vivo and (B) in vitro;

FIG. 40 is a bar chart showing STS hindered cancer cell proliferation in vitro, consistent with the retarded tumor growth in mice;

FIG. 41 is a bar chart showing that fasting differentially regulated the expression of stress-responsive components including forkhead box O3 (FOXO3), nuclear factor kappa B (NFkB), and hemeoxygenase 1 (HO-1) by causing significant repression in the tumors, but considerable induction in the normal organs; Student's t-test; *P<0.05, P<0.01, *P<0.001;

FIG. 42 provides assay results showing that STS increased intracellular oxidative stress estimated by a superoxide marker (DHE);

FIG. 43 provides assay results showing that STS increases CP-induced intracellular superoxide levels; murine breast cancer cells (4T1) were fasted and treated with CPin vitro;

FIGS. 44A-44B provide assay results showing that fasting selectively increased the level of caspase-3 cleavage/activation in the tumors, but not in the normal organs/cells (A) in vivo and (B) in vitro;

FIG. 45 provides assay results showing that STS induced autophagy to sustain cellular energetics;

FIG. 46 is a bar chart showing autophagy-blockade during STS further increases cell death;

FIG. 47 is a plot of the results of an experiment in which murine breast cancer cells (4T1) were treated with hemin, the most common inducer of HO-1 (10 μM), in normal or low glucose under 1% FBS, then challenged with CP;

FIG. 48 is a plot showing that HO-1 is a major mediator of fasting-dependent DSR; murine breast cancer cells were treated with hemin, the most common inducer of HO-1, in normal or low glucose under normal (10%) or low (1%)FBS for 24 hours before and 24 during CP treatment;

FIG. 49 is a plot of the results of an experiment in which murine breast cancer cells (4T1) were treated with ZnPP (20 μM), a commonly used HO-1 inhibitor in normal or low glucose under 1% FBS, then challenged with CP;

FIG. 50 is a plot showing that HO-1 is a major mediator of fasting-dependent DSR; murine breast cancer cells were treated with ZnPP, a commonly used HO-1 inhibitor, in normal or low glucose under normal (10%) or low (1%)FBS for 24 hours before and 24 during CP treatment;

FIG. 51 provides a model for fasting-dependent tumor sensitization to chemotherapy in response to fasting, glucose, IGF-I and other pro-growth molecules/factors are reduced, malignant cells respond to this reduction by activating AKT/S6K and eIF2α and attempting to increase translation but also by reducing the expression of stress resistance proteins FOXO3a, NFkB, and HO-1, these changes lead to the increase in oxidative stress and DNA damage, activation of caspase-3 and cell death;

FIG. 52 is a plot of the results of an experiment in which serum IGF-I levels in female CD1 mice fed with control diet (T.D.7912), fed with amino acid formula (AA-D), or starved for 2.5 days (short-term starvation, STS); modified amino acid diet reduced serum IGF-I by 50% after 5 days' feeding;

FIG. 53 is a plot showing that feeding of modified amino acid diet maintained low serum IGF-1 level after short-term starvation (STS); female CD1 mice were starved for 2.5 days and fed with control diet (T.D.7912) or modified amino acid diet (AA-D, for 2 or 4 days;

FIGS. 54A-54B are plots showing blood glucose levels: (A) female CD1 mice were starved for 3 days or fed with hypocaloric (6% of normal caloric intake) VCM diet (for 3 days) or modified amino acid diet (AA-D, for 3 or 5 days); (B) female CD1 mice were starved for 2.5 days and re-fed with either control of modified amino acid diet for 4 days, glucose was measured after 4-hours of food deprivation;

FIGS. 55A-55B provide bar charts giving results of experiments in which serum IGF-I levels: female CD1 mice were starved for 2.5 days (STS), fed with hypo-caloric VCM-M diet (for 2 days) followed by 1-day of modified amino acid diet (M/AA), fed with hypo-caloric VCM-H diet (for 2 days) followed by 1-day of modified amino acid diet (H/AA), Tukey's test, compared to control; (B) Two-days feeding of hypocaloric VCM diets followed by 1-day of modified amino acid diet enhanced survival of mice treated with Doxorubicin (DXR, 18 mg/kg);

FIGS. 56A-56B are plots of the results of an experiment in which female CD1 mice were fed with control (TD.7912), starved, or fed with VegeGel for 2.5 days: (A) Fasting blood glucose; (B) Serum IGF-I levels; and FIGS. 57A-57B are plots of the results of an experiment in which female CD1 mice were fed with control diet (TD.7912), calorie-restricted ketogenic diet (3 days), or calorie-restricted ketogenic diet (1 days) followed with VegeGel (2 days): (A) Fasting blood glucose; (B) Serum IGF-I levels.

DETAILED DESCRIPTION

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "essential amino acid" refers to amino acids that cannot be synthesized by an organism. In humans, essential amino acids include isoleucine, leucine, lysine, methionine, phenylalanine, threonine, tryptophan, valine. In addition, the following amino acids are also essential in humans under certain conditions—histidine, tyrosine, and selenocysteine.

The terms "kilocalorie" (kcal) and "Calorie" refer to the food calorie. The term "calorie" refers to the so-called small calorie.

The term "patient" refers to a human or animal, including all mammals such as primates (particularly higher primates), sheep, dog, rodents (e.g., mouse or rat), guinea pig, goat, pig, cat, rabbit, and cow.

The term "starving" means subjecting a cell or patient to reduced or no nutrients.

The term "cancer" refers to a disease or disorder characterized by uncontrolled division of cells and the ability of these cells to spread, either by direct growth into adjacent tissue through invasion, or by implantation into distant sites by metastasis. Exemplary cancers include, but are not limited to, primary cancer, metastatic cancer, carcinoma, lymphoma, leukemia, sarcoma, mesothelioma, glioma, germinoma, choriocarcinoma, prostate cancer, lung cancer, breast cancer, colorectal cancer, gastrointestinal cancer, bladder cancer, pancreatic cancer, endometrial cancer, ovarian cancer, melanoma, brain cancer, testicular cancer, kidney cancer, skin cancer, thyroid cancer, head and neck cancer, liver cancer, esophageal cancer, gastric cancer, intestinal cancer, colon cancer, rectal cancer, myeloma, neuroblastoma, pheochromocytoma, and retinoblastoma.

In general, it is found that short-term starvation (STS or fasting) selectively impedes the growth of tumors and protects normal cells from chemotherapy toxicity but sensitizes cancer cells to it. Specific embodiments of methods and compositions that achieve this goal are set forth below. Although the operation of the present invention is not limited to any particular mechanism, the protection observed in various embodiments of the present invention is due in part to modulation of the IGF-I pathway and glucose levels, without interfering with its effect on cancer cells (Differential Stress Resistance, DSR). The foundation for the protective effect of fasting appears to be based on the ability to reallocate energy to protection/maintenance from reproduction/growth when nutrients are scarce or absent. It should be pointed out, long-term dietary restriction causes a much more modest reduction in IGF-I and glucose compared to fasting. Moreover, unlike fasting, long-term dietary restriction is not feasible for the great majority of cancer patients since it causes chronic weight loss and is very difficult to maintain. Instead, an average of about 62 hours of fasting prior to and 24 hours post-chemotherapy was well tolerated by cancer patients receiving a variety of toxic treatments.

It should also be pointed out that oncogenic mutations, which are generally found in pathways associated with cellular growth and stress response, prevent the switch to the high protection mode in malignant cells and continue to promote growth or a growth-associated state even during fasting. Yeast and mammalian studies have suggested that the sensitization of malignant cells to toxins/oxidants may be largely independent of the type of oncogenic mutations owing to the redundancy in the pro-growth pathway in the inhibition of entry into the protected mode, indicating that the great majority of cancer cells and cancer types should not become protected in response to STS or low IGF-I.

In an embodiment of the present invention, a method of alleviating cancer growth or a symptom of cancer is provided. In accordance with the present embodiment, a patient with cancer is identified and then provided with a first diet for a first predetermined period of time. The first diet provides the patient with at most 50% of the patient's normal caloric intake with at least 50% of the kilocalories being derived from fat, preferably monounsaturated fats. The patient's normal caloric intake is the number of kcal that the patient consumes to maintain his/her weight. The patient's normal caloric intake may be estimated by interviewing the patient or by consideration of a patient's weight. As a rough guide, patient's normal caloric intake is on average 2600 kcal/day for men and 1850 kcal/day for women. In a refinement, the first diet provides the patient with from 700 to 1200 kcal/day. In a particularly useful refinement, the first diet provides the male patient of average weight with about 1100 kcal/day and the female patient of average weight with 900 kcal/day. Typically, the first predetermined period of time is from about 1 to 5 days. In a refinement, the first predetermined period of time is 1 day. In order to put the level of fat in the first diet in perspective, the U.S. Food and Drug Administration recommends the following nutritional breakdown for a typical 2000 kilocalorie a day diet: 65 gram fat (about 585 kilocalories), 50 grams protein (about 200 kilocalories), 300 grams total carbohydrates (about 1200 kilocalories). Therefore, in one version of the first diet, a majority of the calories from carbohydrates and proteins are eliminated.

Although the first diet encompasses virtually any source of fat, sources high in unsaturated fat including monounsaturated and polyunsaturated fat sources are particularly useful (e.g., omega-3/6 essential fatty acids). Suitable examples of monounsaturated food sources include, but are not limited to, peanut butter, olives, nuts (e.g., almonds, pecans, pistachios, cashews), avocado, seeds (e.g., sesame), oils (e.g., olive, sesame, peanut, canola), etc. Suitable examples of polyunsaturated food sources include, but are not limited to, walnuts, seeds (e.g., pumpkin, sunflower), flaxseed, fish (e.g., salmon, tuna, mackerel), oils (e.g., safflower, soybean, corn). The first diet also includes a component selected from the group consisting of vegetable extracts, minerals, omega-3/6 essential fatty acids, and combinations thereof. In one refinement, such a vegetable extract provides the equivalent of 5 recommended daily servings of vegetable. Suitable sources for the vegetable extract include, but are not limited to, bokchoy, kale, lettuce, asparagus, carrot, butternut squash, alfalfa, green peas tomato, cabbage cauliflower, beets. Suitable sources for the omega-3/6 essential fatty acids include fish such as salmon, tuna, mackerel, bluefish, swordfish, and the like.

The patient is then provided a second diet for a second predetermined period of time. The second diet provides the patient with at most 500 kcal/day. In a refinement, the second diet provides the patient with at most 200 kcal/day. Typically, the second predetermined period of time is from about 2 to 7 days. In a particularly useful refinement, the second predetermined period of time is 3 days. In still another refinement, the second diet includes a component selected from the group consisting of vegetable extracts, minerals, omega-3/6 essential fatty acids, and combinations thereof. In one refinement, such a vegetable extract provides the equivalent of 5 recommended daily servings of vegetable. Suitable sources for the vegetable extract include, but are not limited to, bokchoy, kale, lettuce, asparagus, carrot, butternut squash, alfalfa, green peas tomato, cabbage cauliflower, beets. Suitable sources for the omega-3/6 essential fatty acids include fish oils from salmon, tuna, mackerel, bluefish, swordfish, and the like.

The effectiveness of the first and second diets is monitored by measurement of a number of patient parameters. For example, it is desirable that the patient's serum concentration of IGF-I be reduced by 25-90% by the end of the second diet period. It is also desirable that the blood glucose concentration in the patient be reduced by 25-75% by the end of the second diet period.

In a variation of the present embodiment, the patient is provided with a third diet for a third predetermined period of time. The third diet is to supplement the normal diet of the patient. Characteristically, the replenishing composition includes essential amino acids, minerals, and essential fats. Advantageously, the third diet will allow the patient to regain the normal weight and maximize strength. Typically, the third predetermined period of time is at least 5 days. The replenishing composition will also optionally include a number of additional components. For example, the replenishing composition may include a vegetable extract. In one refinement, such a vegetable extract provides the equivalent of 5 recommended daily servings of vegetable. Suitable sources for the vegetable extract include, but are not limited to, bokchoy, kale, lettuce, asparagus, carrot, butternut squash, alfalfa, green peas tomato, cabbage cauliflower, beets. The replenishing composition may also include omega-3/6 essential fatty acids, and non-essential amino acids. Examples of suitable non-essential amino acids include, but are not limited to, histidine, serine, taurine, tyrosine, cysteine, glutamine, and combinations thereof. The replenishing composition may also include a multi-mineral tablet containing iron, zinc, copper, magnesium, and calcium and may also contain a vitamin B complex including vitamin B12.

In another embodiment of the present invention, a method of sensitizing cancer to chemotherapy drugs is provided. In accordance with the present method, a patient with cancer is identified and is then provided a first diet for a first predetermined period of time. Examples of cancers that are susceptible to the present method include but are not limited to, skin cancer, colon cancer, breast cancer, esophageal cancer, prostate cancer, lung cancer, uterus cancer, ovary cancer, prostate cancer, glioma, melanoma, neuroblastoma, and pheochromocytoma. The first diet provides the patient with at most 50% of the patient's normal caloric intake with at least 50% of the kilocalories being derived from fat. Typically, the first predetermined period of time is from about 1 to 5 days. In a refinement, the first predetermined period of time is 1 day. As set forth above, the first diet encompasses virtually any source of fat, with sources high in unsaturated fat, particularly monounsaturated fat sources, preferred. Suitable examples of monounsaturated food sources include, but are not limited to, peanut butter, olives, nuts (e.g., almonds, pecans, pistachios, cashews), avocado, seeds (e.g., sesame), oils (e.g., olive, sesame, peanut, canola), etc. Suitable examples of polyunsaturated food sources include, but are not limited to, walnuts, seeds (e.g., pumpkin, sunflower), flaxseed, fish (e.g., salmon, tuna, mackerel), oils (e.g., safflower, soybean, corn). Additional details of the first diet are the same as those set forth above.

A second diet is then provided to the patient for a second predetermined period of time. The second diet provides the patient with at most 500 kcal/day. In a refinement, the second diet provides the patient with at most 200 kcal/day. Typically, the second predetermined period of time is from about 2 to 7 days. In a particularly useful refinement, the second predetermined period of time is 3 days. Additional details of the second diet are the same as those set forth above.

A chemotherapy agent is administered to the patient during or after the patient consumes the second diet. Typically, the chemotherapy agent is administered after 48-72 hours of the second diet. It is readily appreciated that the present method is effective with virtually any chemotherapy agent. Examples of useful chemotherapy agents include, but are not limited to, DNA alkylating agents, oxidants, topoisomerase inhibitors, and combinations thereof. Specific examples of useful chemotherapeutic agents include, but are not limited to, methyl methanesulfonate, cyclophosphamide, etoposide and other topoisomerase inhibitors, doxorubicin, cisplatin, carboplatin and other platinum based drugs, gemcitabine, docetaxel, or 5-FU.

In a variation of the present invention, the patient is subsequently provided with a third diet for a third predetermined period of time. The third diet supplements the patient's normal caloric intake and includes a replenishing composition. Characteristically, the replenishing composition includes essential amino acids. The replenishing composition may also include natural sources of essential fatty acids, vitamins and minerals and a multi-mineral tablet containing iron, zinc, copper, magnesium, and calcium and may also contain a vitamin B complex including vitamin B12.

As set forth above, the third diet together with the patient's normal diet will allow the patient to regain the normal weight and maximize strength. Typically, the third predetermined period of time is at least 5 days and may continue indefinitely. In a refinement, the third predetermined period of time is from about 4 days to about 14 days. A week is estimated to be nearly optimal for this purpose. The replenishing composition will also optionally include a number of additional components. For example, the replenishing composition may include a vegetable extract. In one refinement, such a vegetable extract provides the equivalent of 5 recommended daily servings of vegetable. Suitable sources for the vegetable extract include, but are not limited to, bokchoy, kale, lettuce, asparagus, carrot, butternut squash, alfalfa, green peas tomato, cabbage cauliflower, beets. The replenishing composition may also include omega-3/6 essential fatty acids, and non-essential amino acids. Examples of suitable non-essential amino acids include, but are not limited to, histidine, serine, taurine, tyrosine, cysteine, glutamine, and combinations thereof. Additional details of the third diet are the same as those set forth above.

The method of the present embodiment provides a number of therapeutic advantages. For example, the method allows the chemotherapy agent to be provided to the patient for a longer period of time than is standard practice for the chemotherapy agent when the patient is not provided the first diet and the second diet. This increase in duration is a result of the first and second diets decreasing the toxic effects of the chemotherapy agents and/or rendering cancer cells more susceptible to the chemotherapy agents than normal (i.e., non-cancerous) cells. For many patients, the host protecting first and second diets allow the chemotherapy agent to be administered in a greater amount than in treatment protocols not using the first and second diets. Typically, such agents can be administered in an amount that is at least 10% greater than the amounts normally tolerated by the patient. However, doses of such agents in certain patients can increase from 10% to 40%. In such scenarios, the patient is able to be treated more aggressively. In another refinement, the cancer sensitizing first and second diets allow for a lower amount of chemotherapy agent than the normal amount to be provided to the patient while maintaining a near optimal or enhanced response. In such circumstances, the chemotherapy agents can be administered in an amount that is at least 10% lower than the amounts normally administered. In some patients, doses of such agents may be lowered from 10% to 40% to reduce unwanted toxicity. The present method also allows chemotherapeutic treatment of patients exhibiting unacceptable toxic side-effects to continue. In such situations, patients exhibiting a symptom of chemotherapeutic-related toxicity are identified and then provided the first, second and third diets in the manner and duration set forth above. Advantageously, the present method also allows the continued treatment of patients that have been identified as terminal and who would otherwise discontinue therapy. In still another variation, the first and second diets are administered during the chronic administration of chemotherapeutic agents, for example, 5 day treatment with 5-FU.

In another embodiment of the present invention, a method of sensitizing cancer to radiation therapy is provided. In accordance with the present method, a patient with cancer is identified and is then provided a first diet for a first predetermined period of time. Examples of cancers that are susceptible to the present method include, but are not limited to, skin cancer, colon cancer, breast cancer, esophageal cancer, prostate cancer, lung cancer, uterus cancer, ovary cancer, prostate cancer, glioma, melanoma, neuroblastoma, and pheochromocytoma. The first diet provides the patient with at most 50% of the patient's normal caloric intake with at least 50% of the kilocalories being derived from fat. Typically, the first predetermined period of time is from about 1 to 5 days. In a refinement, the first predetermined period of time is 1 day. As set forth above, the first diet encompasses virtually any source of fat, with sources high in unsaturated fat, particularly monounsaturated fat sources, preferred. Suitable examples of monounsaturated food sources include, but are not limited to, peanut butter, olives, nuts (e.g., almonds, pecans, pistachios, cashews), avocado, seeds (e.g., sesame), oils (e.g., olive, sesame, peanut, canola), etc. Suitable examples of polyunsaturated food sources include, but are not limited to, walnuts, seeds (e.g., pumpkin, sunflower), flaxseed, fish (e.g., salmon, tuna, mackerel), oils (e.g., safflower, soybean, corn). Additional details of the first diet are the same as those set forth above.

A second diet is then provided to the patient for a second predetermined period of time. The second diet provides the patient with at most 500 kcal/day. In a refinement, the second diet provides the patient with at most 200 kcal/day. Typically, the second predetermined period of time is from about 2 to 7 days. In a particularly useful refinement, the second predetermined period of time is 3 days. Additional details of the second diet are the same as those set forth above.

Radiation therapy is administered to the patient during or after the patient consumes the second diet. Typically, the radiation therapy is administered after 48-72 hours of the second diet.

In a variation of the present invention, the patient is subsequently provided with a third diet for a third predetermined period of time. The third diet supplements the patient's normal caloric intake and includes a replenishing composition. Characteristically, the replenishing composition includes essential amino acids. The replenishing composition may also include natural sources of essential fatty acids, vitamins and minerals and a multi-mineral tablet containing iron, zinc, copper, magnesium, and calcium and may also contain a vitamin B complex including vitamin B12.

As set forth above, the third diet, together with the patient normal diet, will allow the patient to regain the normal weight and maximize strength. Typically, the third predetermined period of time is at least 5 days and may continue indefinitely. In a refinement, the third predetermined period of time is from about 4 days to about 14 days. A week is estimated to be nearly optimal for this purpose. The replenishing composition will also optionally include a number of additional components. For example, the replenishing composition may include a vegetable extract. In one refinement, such a vegetable extract provides the equivalent of 5 recommended daily servings of vegetable. Suitable sources for the vegetable extract include, but are not limited to, bokchoy, kale, lettuce, asparagus, carrot, butternut squash, alfalfa, green peas tomato, cabbage cauliflower, beets. The replenishing composition may also include omega-3/6 essential fatty acids, and non-essential amino acids. Examples of suitable non-essential amino acids include, but are not limited to, histidine, serine, taurine, tyrosine, cysteine, glutamine, and combinations thereof. Additional details of the third diet are the same as those set forth above.

In yet another embodiment of the present invention, a therapeutic meal package for providing meals to a cancer patient that retards cancer growth and enhances the efficacy of chemotherapy drugs is provided. The therapeutic meal package is designed to provide the appropriate nutritional and caloric requirements of the methods set forth above. The therapeutic meal package includes a first meal component, a second meal component and a replenishing composition. The first meal component provides the nutritional components of the first diet set forth above. The first meal component is portioned into meals that provide the cancer patient at most 50% of the patient's normal caloric intake with at least 50% of the kilocalories derived from fat. The first meal component is in a sufficient amount to provide meals for a first predetermined period of time. In a refinement, the first meal component also includes extracts equivalent to 5 serving of vegetables as well as omega-3/6 essential fatty acids.

The second meal component provides the nutritional components of the second diet set forth above. The second meal component is portioned into meals that provide the cancer patient at most 500 kcal/day. The second meal component is in a sufficient amount to provide meals for a second predetermined period of time. The second meal component also includes extracts equivalent to 5 serving of vegetables as well as minerals and omega-3/6 essential fatty acids.

The replenishing composition at least partially provides the nutritional components of the third diet set forth above. Typically, the replenishing composition is combined with the patient's normal diet in order to provide the patient with a somewhat normal caloric intake. The replenishing composition includes essential amino acids. The replenishing composition is in a sufficient amount to provide replenishment for a third predetermined period of time.

As set forth above, the first meal component is high in fat. Although the first meal component encompasses virtually any source of fat, sources high in unsaturated fat, particularly monounsaturated fat sources, are preferred to minimize potentially detrimental cardiovascular side effects of fats, particularly in patients who will make frequent use of this diet. Suitable examples of monounsaturated food sources include, but are not limited to, peanut butter, olives, nuts (e.g., almonds, pecans, pistachios, cashews), avocado, seeds (e.g., sesame), oils (e.g., olive, sesame, peanut, canola), etc. Suitable examples of polyunsaturated food sources include, but are not limited to, walnuts, seeds (e.g., pumpkin, sunflower), flaxseed, fish (e.g., salmon, tuna, mackerel), oils (e.g., safflower, soybean, corn). The first meal component also includes a component selected from the group consisting of vegetable extracts, minerals, omega-3/6 essential fatty acids, and combinations thereof. In one refinement, such a vegetable extract provides the equivalent of 5 recommended daily servings of vegetable. Suitable sources for the vegetable extract include, but are not limited to, bokchoy, kale, lettuce, asparagus, carrot, butternut squash, alfalfa, green peas tomato, cabbage cauliflower, beets. Suitable sources for the omega-3/6 essential fatty acids include fish such as salmon, tuna, mackerel, bluefish, swordfish, and the like.

As set forth above, the second food component provides a very low kcal to the patient. In one refinement, the second food component includes a component selected from the group consisting of vegetable extracts, minerals, omega-3/6 essential fatty acids, and combinations thereof. In one refinement, such a vegetable extract provides the equivalent of 5 recommended daily servings of vegetable. Suitable sources for the vegetable extract include, but are not limited to, bokchoy, kale, lettuce, asparagus, carrot, butternut squash, alfalfa, green peas tomato, cabbage cauliflower, beets. Suitable sources for the omega-3/6 essential fatty acids include fish such as salmon, tuna, mackerel, bluefish, swordfish, and the like.

The replenishing composition is designed so that the patient's normal weight and strength are maintained (or re-established if there has been a weight lost). In a refinement, the replenishing composition further includes extracts equivalent to 5 servings of vegetables as well as minerals and omega-3/6 essential fatty acids. It should be appreciated that the replenishing composition is to be taken with a normal diet so that the weight and strength goals are achieved. Typically, the normal diet will provide about the patient's normal caloric intake as set forth above.

In a variation, the therapeutic meal package also includes instructions for administering the first meal component, the second meal component, and the replenishing composition to the cancer patient. The instruction will provide the details set forth above with respect to the methods. In one refinement, the instructions state that the first food component is to be provided to the patient over a first predefined period of time as set forth above. Typically, the first predetermined period of time is from about 1 to 2 days. In a refinement, the first predetermined period of time is 1 day. The instructions also state that the second food component is to be taken over a second predetermined period of time as set forth above. Typically, the second predetermined period of time is from about 2 to 7 days. In a particularly useful refinement, the second predetermined period of time is about 3 days. The instructions also state that the replenishing composition is to be taken with the normal diet, and in particular, a sufficient amount of additional food items that the patient's weight and strength is maintained or regained. Typically, the third predetermined period of time is at least 5 days. In a refinement, the third predetermined period of time is from about 4 days to about 14 days. A week is found to be nearly optimal for this purpose.

In a variation of the present embodiment, the therapeutic food package is packaged in a container (e.g., a box). In a refinement, each of the first meal component and the second meal component are portioned into daily servings with labeling so indicating. In a further refinement, each daily portion is further divided into three meals. Typically, each meal will be a combination of solid food, a shake and a soup (day 1) and only soups and shakes for days 2, 3, and 4 (3 meals/day). Each package will also contain pills with essential fatty acids, minerals and vitamins and/or vegetable extracts. The box will also contain 1 week supply of the replenishment diet which will be in the form of pills. Generally, non-natural sources of any item in all components of the diet are minimized.

The following examples illustrate the various embodiments of the present invention. Those skilled in the art will recognize many variations that are within the spirit of the present invention and scope of the claims.

Experiment 1

Ten cases are described in which patients diagnosed with a variety of malignancies have voluntarily fasted prior to (48-140 hours) and/or following (24-56 hours) chemotherapy. None of these 10 patients, who received an average of 4 cycles of chemotherapy in combination with fasting, reported significant side effects caused by the fasting itself other than hunger. Toxicity was graded based on the Common Toxicity Criteria (CTC) of the National Cancer Institute (NCI) and self-reported side-effects from five patients indicate that fasting may protect against fatigue, weakness, and gastrointestinal side effects. In those patients whose cancer progression could be monitored, fasting did not prevent the chemotherapy-dependent reduction of tumor mass or tumor markers. Although controlled clinical trials are required to determine the role of fasting in the enhancement of clinical outcomes and the patient's quality of life, the 10 cases presented here suggest that fasting in combination with chemotherapy is feasible, safe, and has the potential to augment existing chemotherapy.

Ten cases are reported of patients diagnosed with various types of cancers, who voluntarily fasted prior to and following chemotherapy. The results presented, based on self-assessed health outcomes and blood readouts, suggest that fasting is safe and can reduce multiple side effects caused by chemotherapy without preventing the killing of cancer cells.

Case 1

Figures 1A, 1B, 1C, 1D:
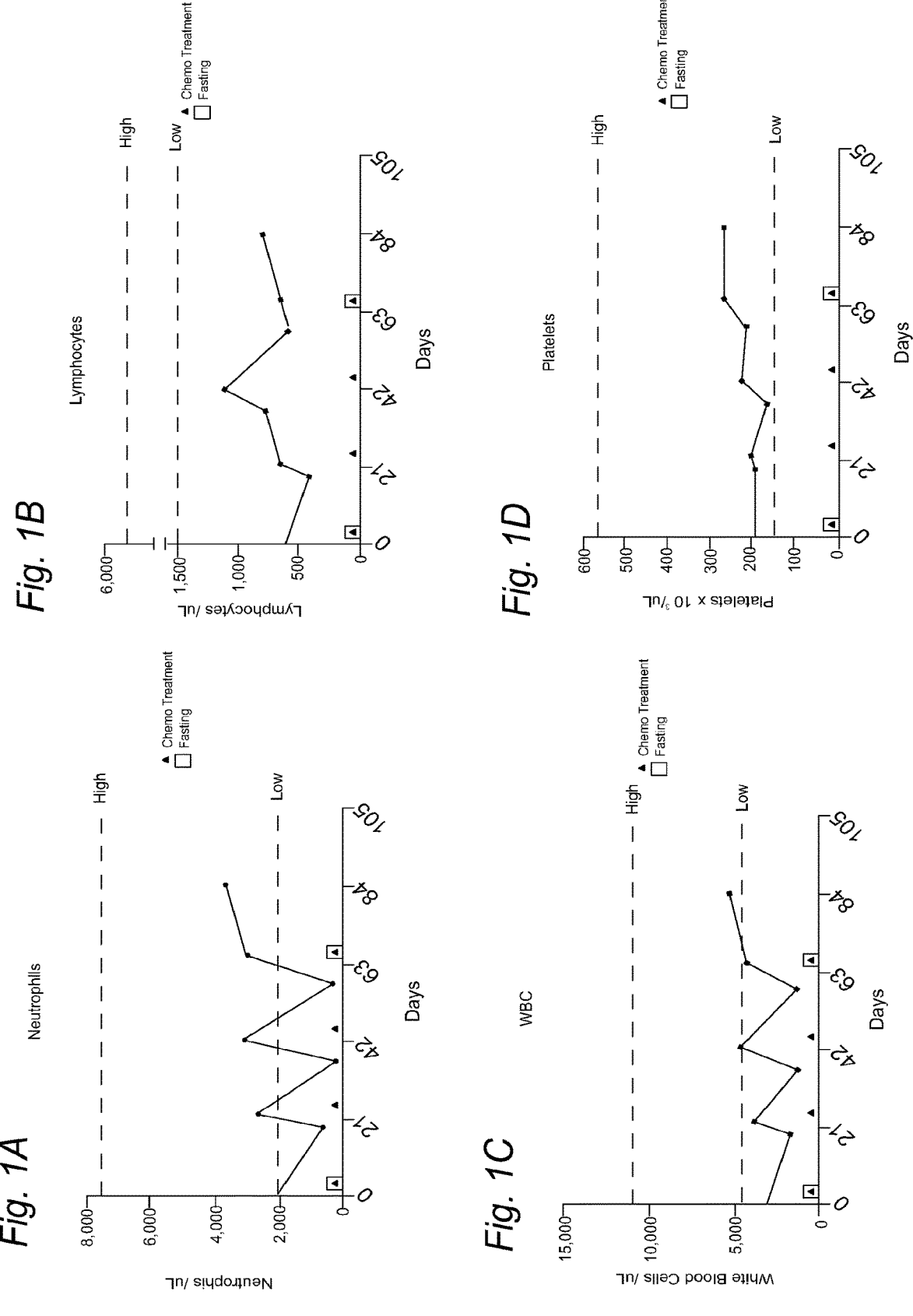
FIGS. 1A-1H provide plots of laboratory values of blood cell counts for case 1: (A) Neutrophils; (B) Lymphocytes; (C) White blood cells, WBC; (D) Platelets; (E) Red blood cells, RBC (F) Hemoglobin, Hgb; (G) Hematocrit, Het; (H)
Figures 1E, 1F, 1G, 1H:
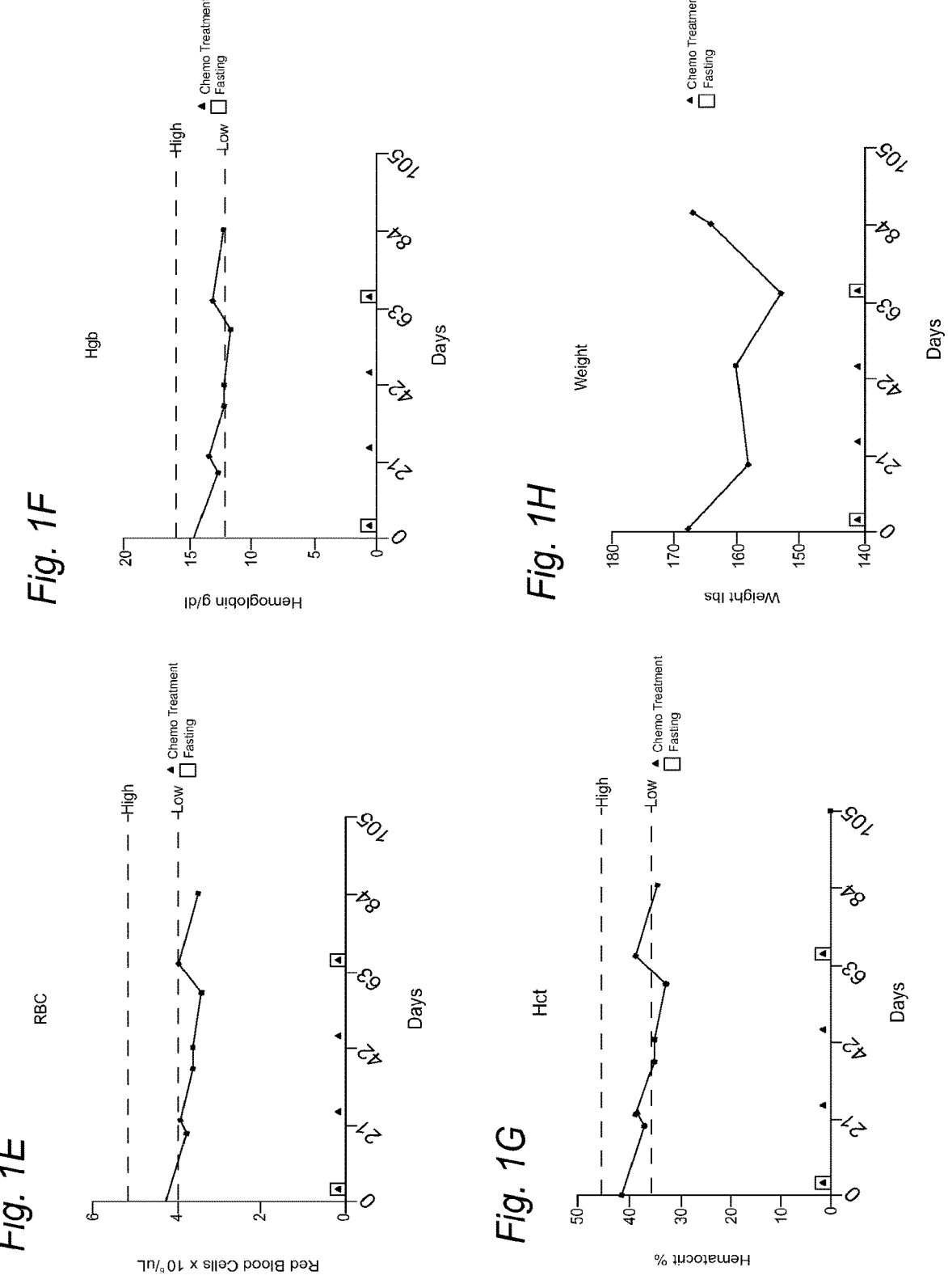

A 51-year-old Caucasian woman diagnosed with stage HA breast cancer to whom adjuvant chemotherapy with docetaxel (DX) and cyclophosphamide (CP) was recommended. She fasted prior to her first chemotherapy administration. The fasting regimen consisted of a complete caloric deprivation for 120 hours prior and 60 hours after chemotherapy (180 hours total), during which she consumed only water and vitamins. The patient completed this prolonged fasting without major inconvenience and lost 7 pounds which were recovered by the end of the treatment (FIG. 1H). After the fasting-chemo cycle, the patient experienced mild fatigue, dry mouth and hiccups (FIG. 2); nevertheless she was able to carry her daily activities (working up to 12 hours a day). By contrast, in the subsequent chemo-treatment cycles (second and third), she received chemotherapy without fasting and complained of moderate to severe fatigue, weakness, nausea, abdominal cramps and diarrhea (FIG. 2). This time the side effects forced her to withdraw from her regular work schedule. For the 4th and last cycle, she opted to fast once again, although with a different regimen which consisted of fasting 120 hours prior to and 24 hours post chemotherapy. Notably, her self-reported side effects were lower despite the expected cumulative damage to tissues from previous cycles. In agreement, blood analysis readouts support that fasting may have a beneficial effect in protecting blood cells. Total white blood cells (WBC) and absolute neutrophils count (ANC) showed a slight but consistent increment at nadir when chemotherapy was preceded by fasting (FIG. 1A, C; Table 1). Furthermore, it was observed that platelets levels did not drop but rather stayed stable or increased during the 1st and 4th cycle, respectively, under fasting-chemo cycles. (FIG. 1D). Interestingly, after the 4th chemotherapy cycle combined with 144-hour fast, ANC, WBC, and platelets counts reached the highest level since the beginning of the chemotherapy 80 days earlier (FIGS. 1A, C and D). Overall, the lab values and the CTC-based surveys suggest that fasting was safe and could conferred protection against the toxic side effects of chemotherapy to this patient.

Case 2

A 68-year-old Caucasian male who was diagnosed in February 2008 with esophageal adenocarcinoma. By the time of diagnosis, metastasis to the left adrenal gland was found on a CT-PET scan, consistent with stage IV disease. The initial treatment was 5-fluorouracil (5-FU) combined with cisplatin (CDDP). Concurrently with this chemotherapy, he also received localized radiation for the first two cycles. Throughout this period the patient experienced multiple side effects including severe weakness, remarkable fatigue, intense vomiting and significant peripheral neuropathy (FIG. 3). Additionally, the patient complained of intense dysphagia secondary to severe mucositis, most likely caused by the radiation treatment. During the third cycle, 5-FU administration had to be withdrawn due to severe nausea and refractory vomiting (FIG. 3). In spite of the aggressive approach with chemotherapy and radiation, his disease progressed. Development of new metastases to the right adrenal gland, lower lobe of the right lung, left sacrum, and coracoid process were shown by a new CT-PET performed in August 2008. These prompted an augmentation of his chemotherapy regimen (4th cycle). Carboplatin (CBDCA) in combination with DTX and 5-Fu (5-FU was administered for 96 hours). The patient incorporated a 72-hour prior and 51-hour post chemotherapy fasting during the 4th cycle. The rationale for the 51 hour post chemotherapy fasting was to protect against the continued administration of 5-FU. The patient lost approximately 7 pounds, 4 of which were regained during the first few days of resuming normal diet (data not shown). Although three chemotherapeutic agents were used in combination during this cycle, self-reported side effects reported were consistently lower than ad lib chemo-cycles (FIG. 3). Prior to his 5th chemo-treatment the patient opted to fast again. Instead of receiving the 5-FU infusion for 96 hours, as he did previously, the same dose of the drug was administered within 48 hours, and the fasting regimen was also modified to 48 hours prior to and 56 hours post drug delivery. Interestingly, there were not only low self-reported side effects, but also an encouraging clinical response documented in a CT-PET scan. Decrease in the standard uptake value (SUV) of the main esophageal mass, the adrenal glands metastases, and the nodule in the right lower lobe of the lung were shown in the scans. For the 6th, 7th, 8th cycle, the patient fasted prior to and following chemotherapy treatments (Table 3). Despite the expected cumulative toxicity most of the side effects were reduced by fasting except for mild diarrhea and abdominal cramps developed during the 7th chemo-cycle. It was very aggressive cancer and despite of the well tolerated chemotherapy the patient's disease progressed and the patient deceased in February 2009.

Case 3

A 74-year-old Caucasian man who was diagnosed in July of 2000 with bilateral prostate adenocarcinoma, Gleason score 7 and PSA level of 5.8 ng/ml. A prostatectomy performed in September of 2000 led to undetectable levels of PSA until January 2003 when it rose to 1.4 ng/ml. Leuprolide acetate together with bicalutamide and finasteride were prescribed. However, administration of these drugs had to be suspended in April 2004 due to severe side effects related to testosterone deprivation. Different drugs including triptorelinpamoate, nilutamide, thalidomide, CP and ketoconazole were utilized to control the disease. In 2007 the patient's PSA level reached 9 ng/ml and new metastases were observed during a bone scan. DTX at 25 mg/m2 on weekly basis was administered, but the PSA levels continue to increase reaching 40.6 ng/ml (data not shown). Bevacizumab was added into the treatment and only then the PSA dropped significantly (data not shown). Consistently a new bone scan showed an overall improvement. Throughout the cycles with chemotherapy the patient experienced significant side effects including fatigue, weakness, metallic taste, dizziness, forgetfulness, short-term memory impairment and peripheral neuropathy (FIG. 5). After stopping the chemotherapy treatments, his PSA rose rapidly. DTX at 75 mg/m2 in a 3-weekly cycle was the regimen elected and once again the patient suffered significant side effects (FIG. 5). In June 2008, Chemotherapy stopped. The patient was enrolled in a phase III clinical trial with abiraterone acetate, a drug that can selectively block CYP17, a microsomal enzyme that catalyzes a series of reactions critical to nongonadal androgen biosynthesis (Derek Raghavan and Eric A. Klein J.C.O 2008). During the trial, the patient's PSA levels increased up to 20.9ng/dl (FIG. 4H), prompting to resume the chemo-treatment. This time the patient opted to fast prior to chemotherapy. His fasting schedules were mostly 60 hours prior to and 24 post drug administration (Table 3).PSA level dropped immediately upon restarting chemo-fasting treatments (DTX 75 mg/m2), and notably, the patient reported considerably lower side effects than in previous ad-lib chemo cycles (FIG. 5). In agreement to the patient's experience, blood readouts were consistently stable and remained within normal range throughout the treatments (FIGS. 4A-G). During the last three cycles, besides fasting the patient applied testosterone (cream 1%) for five days prior to chemotherapy.

As a consequence the PSA level along with testosterone level increased dramatically. Nonetheless, 3 cycles of combined chemotherapy with fasting reduced PSA from 34.2 to 6.43 ng/ml (FIG. 4H). These results do not support the possibility that fasting may confer partial protection to cancer cells.

Case 4

A 61-year-old Caucasian female who was diagnosed in June 2008 with poorly differentiated non-small cell lung carcinoma (NSCLC). The mass, originally seen on a CT scan, proved to be hypermetabolic on a PET study (June 2008) correlating with the biopsy results. In the same PET-scan widespread metastatic disease was shown in multiple mediastinal and left perihilar lymph nodes. Metastases to the bones, liver, spleen, and pancreas were also observed. The initial treatment commenced with the administration of DTX 75 mg/m2 and CBDCA 540 mg/m2 every 21 days. Although she was on a regular diet, during the first 5 cycles she lost an average of 4 pounds after each chemo-treatment; most likely due to chemotherapy toxicity. The patient reported that it took her approximately three weeks to get back to her original weight. Among the side effects experienced, she complained of severe muscle spasms, lower limb neuropathy, significant fatigue, mouth and tongue sores, easy bruising and bowel discomfort (FIG. 7). During the 6th cycle which consisted of the same drugs and dosages, the patient fasted for 48-hours-prior and 24-hours-post chemotherapy. During this period she lost approximately 6 pounds, which were recovered within 10 days (data not shown). Besides mild fatigue and weakness the patient did not complain of any other side effect that she experienced during the five previous cycles (FIG. 7). Note, that cumulative side effects such as peripheral neuropathy, hair loss or short memory impairment may not be reversed by fasting once they developed. By contrast acute toxic side effects were successfully avoided when chemotherapy was administered under fasting conditions (FIG. 7). After the 6th and last cycle, the patient reported that her energy recovered quickly to walk 3 miles only three days after the drug administration. No significant differences were observed in the patient's blood work (FIG. 6A-G). The last radiologic study (PET) performed on February 2009 showed stable disease in the main mass (lower lobe of the left lung), and decreased uptake of the tracer in the spleen and liver when compared to its baseline study.

Case 5

A 74-year-old female patient diagnosed in 2008 with stage IV uterine papillary serous carcinoma. Surgery (TAH-BSO) followed by adjuvant chemotherapy were recommended. Additionally, pelvic, periaortic and precavallymp nodes were removed. Lastly due to a significant enlargement of the right ureter a right nephrectomy was also performed. Six cycles of CBDCA (480 mg) and paclitaxel (280 mg) were administered every 21-days. During the first treatment the patient had a regular diet and experienced fatigue, weakness, hair loss, headaches and complained of gastrointestinal discomfort (FIG. 8). By contrast, during cycle 2-6, the patient fasted prior to and followed the drug administration and reported a reduction on the side effects developed after chemotherapy (Table 3; FIG. 8). In agreement with other reports, fasting did not interfere with the chemo-therapy-dependent killing of cancer cells documented by the reduction in 87% of the tumor marker CA-125 after the 4th cycle (data not shown).

Case 6

A 44-year-old white female patient diagnosed with a right ovarian mass (10×12 cm.) in July 2007. Surgery (TAH-BSO) was carried out. The tumor showed no invasion of the ovarian capsule and the 30+ lymph nodes removed were all negative. Her disease was graded as Stage IA carcinosar-coma of the ovary. The initial treatment deployed was a six-cycle course of ifosfamide and CDDP, which the patient received from July to November of 2007. Her first CT scan, performed in January of 2008, didn't show extra ovaric disease. Seven months later, an MRI revealed multiple new pulmonary nodules. This finding was confirmed by a CT scan where more than 20 new nodules were visualized within the lungs along with some abnormalities (hypodense images=MTS?) in the splenic region and degenerative changes in the spine. Based on these results, a new regimen of drugs including Taxol, carboplatin and avastin was elected. Infusions started in August 2008 and were per-formed in a 3-weekly schedule. Concurrently, the patient was supplemented with high dose vitamin C (50 mg/day). In September 2008, a reassessment with a CT scan showed a noticeable decrease in size and number of multiple scattered bilateral pulmonary nodules. By November, however, a CT scan showed that one of the main nodules increased from 0.5 to 0.8 cm, indicating the progression of the disease. A new treatment consisting of gemcitabine on day one followed by gemcitabine and docetaxel on day eight was prescribed. However, after the first administration of gemcitabine at full dose (900 mg/m2), the patient experienced prolonged neu-tropenia (FIG. 9A) and thrombocytopenia (FIG. 9D) which forced the suspension of the follow up treatment. During the second cycle the patient received a reduced dose of gemcit-abine (720 mg/m2), but again developed prolonged neutro-penia and thrombocytopenia, making it difficult to complete the original schedule. Prior to the third cycle the patient fasted for 62 hours prior and 24 hours post chemotherapy. The patient reported no side effects, regardless whether she had fasted or not, but interestingly the blood work showed remarkable improvement during the fasting-chemo treat-ments (FIG. 10). A trend was noticed in which nadirs were slightly less pronounced and the zeniths were considerably higher in ANC, lymphocyte and WBC counts (FIG. 9A, B, C, respectively; Table 2). Additionally, gemcitabine alone, during the 1st and 2nd chemo-cycle, led to a rapid and steep decrease in platelet counts, which took 11 and 12 days to recover, respectively. (Table 2). However, the platelet counts did not drop, but rather increased, following the first com-bined fasting-gemcitabine treatment (3rd cycle) (FIG. 9D). Platelet nadir did reach a lower level compared to previous chemo-alone treatments, which could be explained by the additive effect of three chemotherapeutic agents (FIG. 9D; Table 2). Nonetheless the zenith in platelet numbers and the time to recover to normal level were much pronounced and shortened, respectively, during the fasting-chemo treatments compared with chemo-alone (FIG. 9D; Table 2). This sig-nificant improvement and faster recovery of platelets after multiple fasting/chemotherapy not only allowed the patient to complete her chemo-treatment, but also suggests that this strategy may have protective effects on blood cells precur-sors, allowing a quicker repopulation of thrombocytes and granulocytes.

Case 7

A 66-year-old Caucasian male who was diagnosed in July 1998 with prostate adenocarcinoma, Gleason score 8. A ProstaScint study performed in the same year displayed positive uptake of the radiotracer in the right iliac nodes, consistent with stage Dl disease. In 1998, the patient received leuprolide acetate and bicalutamide for the first time. In September 1999, those drugs wore off and he was put on finasteride. In December 2000, a CT scan insinuated a local progression of the disease. He started the second cycle with leuprolide acetate and also received High Dose Rate (HDR) brachytherapy and external beam radiation with Intensity Modulated Radiation Therapy (IMRT). Comple-mentary treatment with multiple drugs such as bicalutamide, triptorelinpamoate and nandrolone was applied in order to control the disease. However, his PSA level increased quickly each time the treatment was halted. In April-2008, a Combidex scan revealed a 3×5 cm pelvic mass and left hydronephrosis; In June of the same year, a new PSA relapse along with a new CT scan which further confirmed the mass on the left iliac area prompted the treatments with DTX. The patient decided to fast 60-66 hours prior to and 8-24 hours followed chemotherapy (Table 3). While fasting, the patient experienced lightheadedness and a significant drop in blood pressure, but the self-reported side effects after chemo-therapy were almost non-existent except for mild vibratory sensation in his feet developed after seven consecutive cycles DTX (FIG. 12). Upon analysis the patient's readouts it was found that ANC, WBC, platelets and lymphocytes levels were maintained in the normal range whereas red blood cells and its associated parameters (hematocrit and hemoglobin) did not (FIGS. 11A-G). This suggests that some blood cells may benefit from fasting-dependent pro-tection whereas others don't. Lastly, PSA levels throughout the cycles displayed a consistent decreasing trend supporting that fasting did not interfered the killing of prostate cancer cells (FIG. 11H).

Case 8

A 53-year-old Caucasian female patient who was diag-nosed with stage IIA breast cancer (HER2+). After a Lumpectomy performed in 2008 the patient underwent 4 cycles of chemotherapy scheduled every 21 days. The regimen included DXT (75 mg/m2) and CP (600 mg/m2). Throughout 4 cycles the patient fasted 64 hours prior to and 24 hours post the chemotherapy administration. Side effects reported included mild weakness and mild short-term memory impairment (FIG. 13).

Case 9

A 48 year-old Caucasian female patient diagnosed with breast cancer to whom adjuvant chemotherapy was recom-mended. Her chemotherapy regimen consisted in 4 cycles of doxorubicine (DXR) (110 mg) combined with CP (1100 mg) in 21-day schedule followed by paclitaxel and trastuzumab on weekly basis for 12 weeks. Prior to her first chemo-therapy treatment the patient fasted for 48 hour and referred no adverse effects. During the second cycle the patient incorporated 60 hour of fasting prior to the chemotherapy followed by 5 hour post drug administration. Interestingly, she expressed no hardship in following the fasting. Although she experienced hair loss and mild weakness, the patient did not suffer other commonly reported side effects from chemotherapy (FIG. 14).

Case 10

A 78 year-old Caucasian female diagnosed with RER2 positive breast cancer. Upon diagnosis and after a complicated lumpectomy the patient underwent total mastectomy. Six cycles of adjuvant chemotherapy with CBDCA 400 mg (AUC=6), DTX (75 mg/m2) complemented with G-CSF (Neulasta) and followed by 6 month with trastuzumab were prescribed by the oncologists (Table 3). Throughout the chemotherapy treatments the patient fasted prior and after the drug administration. Although the patient adopted variance of fasting regimen no severe side effects were experienced (FIG. 16; Table 3). Furthermore blood readouts for WBC, ANC, platelets and lymphocytes levels were within normal levels (FIG. 15A-D) throughout the treatment.

Self-reported assessments of all 10 patients were obtained to evaluate the severity of the side effects experienced. Since many of the chemo toxic side effects are cumulative, survey data was compared, including all the combined fasting- and non-fasting associated chemotherapy side effects (FIG. 17A). Toxicity was graded based on the Common Toxicity Criteria of National Cancer Institute. Encouragingly, better self-reported health outcomes were addressed by all the patients even though chemo-fasting cycles were mostly carried out in the later portion of the therapy. Nausea, vomiting, diarrhea, abdominal cramps, and mouth sores were virtually absent from the reports of all 10 patients whenever chemo-fasting cycles were administered, whereas at least one of these symptoms was reported by 5 out of the 6 ad lib fed patients (FIG. 17A). The four patients that always fasted in combination with all the chemo-treatments reported low severity for the majority of the side effects (FIGS. 12, 13, 14, 16). Only mild weakness and hair loss were reported by multiple patients. For the 6 patients that received chemotherapy in association with both, fasting or ad lib diet, the severity of the self-reported side effects was determined by considering only the two closest cycle of chemotherapy in which the patient had fasted or not. There was a general and major reduction in the severity of many of the self-reported side effects in combination with fasting (FIG. 17B). Whereas symptoms such as fatigue and weakness were significantly reduced ($p<0.001$ and $p<0.00193$, respectively), vomiting and diarrhea were never experienced in combination with fasting even though these cycles were consistently carried out at last (FIG. 17B). Notably, there was no side effect, included in the CTC-based survey, whose average severity was increased by fasting (FIG. 17A, 17B).

The survey results, from a small and heterogeneous group of patients, suggest that fasting is safe and well-tolerated in cancer patients and could ameliorate multiple chemotherapy-dependent side-effects. Although, bias could affect the estimation of the side effects by the patient, the trend of improvements in the post-chemotherapy blood readouts support that fasting could in fact protect against different chemotherapy drugs. Notably, fasting is known to protect yeast and mice against a variety of toxins and stresses (Rafaghello, LPNAS 2008; Matsson, M. Annual Rev.

Nutr2005) and therefore a protective effect against multiple chemotherapy drugs in humans would not be surprising.

Results

Ten cancer patients, 7 females and 3 males of a median age of 61 years (range 44-78) receiving chemotherapy, are presented in this study. Four suffered from breast cancer, two from prostate cancer, and four from ovarian, uterine, non small cell carcinoma of the lung, or esophageal adenocarcinoma. All patients had voluntarily fasted for a total of 48 to 140 hours prior to and/or 24 to 56 hours following chemotherapy under the supervision of their treating oncologists. Fasting was well-tolerated in all cases. Hunger, and decrease in blood pressure were common symptoms cited by the patients after the prolonged fasting periods.

Discussion

General dietary recommendations during cancer treatment are based on overall goals to prevent or reverse nutrient deficiencies, to preserve lean body mass, and to minimize nutrition related side effects (such as decreased appetite, nausea, taste changes, or bowel changes) (Doyle, Nutrition and Physical Activity During and After Cancer Treatment, 2006). Contrary to standard post-chemotherapy diets, most patients in this series reported fasting to be feasible and beneficial by reducing side-effects such as fatigue, weakness, nausea, vomiting and abdominal cramps. Minor complaints arose during fasting including dizziness, hunger, or headaches, at a level which did not interfere with normal activities, including work.

Weight loss is a major concern in cancer patients. This can be due to cancer itself, reduced appetite following chemotherapy, or gastrointestinal damage. Notably, in this case report, weight loss during fasting was rapidly recovered in most of the patients. For the patients who received chemotherapy both with and without fasting, chemotoxic side effects appeared to be attenuated during fasting-chemo cycles. Symptoms which appeared to be ameliorated by this intervention were primarily gastrointestinal and constitutional.

In non-malignant cells, challenging conditions such as fasting/glucose starvation stimulates the organism to suppress growth/reproduction and divert its energy towards maintenance/repair, and maximize its chance of survival (Longo. Nature. 2005). Therefore, growth factors such as IGF-I decrease (Thiessen, J.P. Endocrine Rev 1994; Stephen R. Spindler Annual review of nutrition 2007) and stress resistance mechanisms such as the unfolded protein response (UPR) including heat shock proteins (HSP 70) and glucose response proteins (GRP 78) increase (Mote, P. L. Mechanism Age Dev 1998; Lee, A. S Trends in biochemical science 2001; Ramachandra K. Reddy J. of Biological. Chemistry 2003). Normal cells would respond to these changes, whereas malignant cells would be unresponsive due to self-sufficiency in growth signals, (Hanahan. Hallmarks of cancer. 2000). Thus, fasting would selectively protect normal cells against chemotherapy toxicity without compromising drug activity on cancer cells.

Although the results are yet preliminary with only 10 patients, they are nonetheless encouraging since most of the side effects presented here have a cumulative pattern and the chemo-fasting cycle were carried out mostly In the later portion of the treatments.

TABLE 1

| | Cycle # | Fast (hours) | Chemotherapy | Tumor Response |
|---|---|---|---|---|
| Case 1 | 1 | 140 pre 40 post | Docetaxel 75 mg/m$^2$ + Cyclophosphamide 600 mg/m$^2$ | n/a |
| | 4 | 120 pre 24 post | Docetaxel 75 mg/m$^2$+ Cyclophosphamide 600 mg/m$^2$ | n/a |
| Case 2 | 4 | 72 pre 51 post | Docetaxel 64.6 mg/m$^2$ + carboplatin 485 mg. | — |
| | 5 | 48 pre 56 post | Docetaxel 79 mg/m$^2$ + carboplatin 470 mg + 5FU 2415.7 mg/m$^2$ | Stable disease on CT/PET |
| | 6 | 48 pre 56 post | Docetaxel 79 mg/m$^2$ + carboplatin 470 mg + 5FU 2415.7 mg/m$^2$ | Improvement on CT/PET Refer to text |
| | 7 | 48 pre 56 post | Docetaxel 79 mg/m$^2$ + carboplatin 470 mg + 5FU 2415.7 mg/m$^2$ | — |
| | 8 | 48 pre 56 post | Docetaxel 79 mg/m$^2$ + carboplatin 470 mg + 5FU 2415.7 mg/m$^2$ | Progression of Disease on CT/PET |
| Case 3 | 5-12 | 60-66 pre 24 post | Docetaxel 75 mg/m$^2$ | See PSA Graph |
| Case 4 | 6 | 48 pre 24 post | Docetaxel 75 mg/m$^2$ + carboplatin 540 mg | Stable disease CT/PET refer to text |
| Case 5 | 2 | 36 pre | Carboplatin 480 mg + Paclitaxel 280 mg | — |
| | 3-4 | 60 pre | Carboplatin 480 mg + Paclitaxel 280 mg | 87% decline in CA 125, Reduction in lymph nodes on CT |
| | 5-6 | 60 pre 24 post | Carboplatin 480 mg + Paclitaxel 280 mg | |
| Case 6 | 3 | 62 pre 24 post | Gemcitabine 720 mg/m$^2$ (day 1) + GMZ 720 mg/m$^2$ (Day 8) | — |
| | 4 | 62 pre 24 post | Gemcitabine 720 mg/m$^2$ (day 1) + GMZ 720 mg/m$^2$ (Day 8) | — |
| | 5-6 | 602 pre 24 post | Gemcitabine 900 mg/m$^2$ (day 1) + GMZ 900 mg/m$^2$Docetaxel 100 mg/m$^2$ (Day 8) | Stable disease on PET scan, no new MTS |
| Case 7 | 1 | 65 pre 8 post | Docetaxel 60 mg/m$^2$ | See PSA Graph |
| | 2-8 | 65 pre st post* | Docetaxel 75 mg/m$^2$ | See PSA Graph |
| Case 8 | 1-4 | 64 pre 24 post** | Docetaxel 75 mg/m$^2$ | See PSA Graph |
| Case 9 | 1 | 48 pre | Doxorubicin 110 mg + Cyclophosphamide 1100 mg | n/a |
| | 2-4 | 61 pre 4 post | Doxorubicin 110 mg + Cyclophosphamide 1100 mg | n/a |
| Case 10 | 1 | 60 pre | Docetaxel 75 mg/m$^2$ + Carboplatin 400 mg | n/a |
| | 2 | 48 pre | Docetaxel 75 mg/m$^2$ + Carboplatin 400 mg | n/a |
| | 3 | 40 pre 24 post | Docetaxel 75 mg/m$^2$ + Carboplatin 400 mg | n/a |
| | 4 | 48 pre 24 post | Docetaxel 75 mg/m$^2$ + Carboplatin 400 mg | n/a |
| | 5 | 36 pre 24 post | Docetaxel 75 mg/m$^2$ + Carboplatin 400 mg | n/a |
| | | 20 pre 20 post | Docetaxel 75 mg/m$^2$ + Carboplatin 400 mg | n/a |

*also utilized low glycemic diet for 24 hours prior to fast.
**also utilized liquid diet for 24 hours after fast.
n/a = not applicable, due to chemotherapy being administered in the adjuvant setting.

TABLE 2

| | | Fasting (hr) | | | WBC | | | | ANC | | | | PLT | | | |
|---|---|---|---|---|---|---|---|---|---|---|---|---|---|---|---|---|
| Days | Treatment | pre | post | G-CSF | Nadir* (Days) | cell/ uL | Recov- ery** (Days) | Zenith Cell/uL | Nadir* (Days) | cell/ uL | Recov- ery** (Days) | Zenith cell/uL | Nadir* (Days) | cell/ uL | Recov- ery** (Days) | Zenith cell/uL |
| 4 | Gemcitabine (900 mg/m$^2$) | ad Lib | — | — | 7 | 900 | 16 | 9000 | 7 | 400 | 16 | 7500 | 10 | 63 | 11 | 203 |
| 25 | | | | G-CSF | | | | | | | | | | | | |

TABLE 2-continued

| | | Fasting (hr) | | | WBC | | | | ANC | | | | PLT | | | |
|---|---|---|---|---|---|---|---|---|---|---|---|---|---|---|---|---|
| | | | | | Nadir* | cell/ | Recov-ery** | Zenith | Nadir* | cell/ | Recov-ery** | Zenith | Nadir* | cell/ | Recov-ery** | Zenith |
| Days | Treatment | pre | post | G-CSF | (Days) | uL | (Days) | Cell/uL | (Days) | uL | (Days) | cell/uL | (Days) | uL | (Days) | cell/uL |
| 27 | Gemcitabine (720 mg/m²) | ad Lib | — | — | 5 | 700 | 2 | 9200 | 5 | 700 | 2 | 8100 | 9 | 59 | 12 | 177 |
| 32 | | | | G-CSF | | | | | | | | | | | | |
| 33 | | | | G-CSF | | | | | | | | | | | | |
| 34 | | | | G-CSF | | | | | | | | | | | | |
| 36 | | | | G-CSF | | | | | | | | | | | | |
| 39 | | | | G-CSF | | | | | | | | | | | | |
| 41 | | | | G-CSF | | | | | | | | | | | | |
| 42 | | | | G-CSF | | | | | | | | | | | | |
| 43 | Gemcitabine (720 mg/m²) | 62 | 24 | — | 5 | 700 | 5 | 7800 | 5 | 700 | 5 | 6400 | — | | | — |
| 48 | | | | G-CSF | | | | | | | | | | | | |
| 49 | | | | G-CSF | | | | | | | | | | | | |
| 51 | | | | G-CSF | | | | | | | | | | | | |
| 53 | Gemcitabine (720 mg/m²) Docetaxel (80 mg/m²) | 62 | 24 | — | 4 | 1800 | 3 | 11800 | 4 | 1300 | 3 | 10700 | 8 | 27 | 10 | 280 |
| 54 | | | | G-CSF | | | | | | | | | | | | |
| 67 | Gemcitabine (720 mg/m²) | 62 | 24 | — | 9 | 2700 | 5 | 21400 | 9 | 1600 | 2 | 18600 | — | | | — |
| 76 | Gemcitabine (720 mg/m²) Docetaxel (80 mg/m²) | 62 | 24 | — | — | | — | | — | | — | | 8 | 38 | 6 | 286 |
| 78 | | | | G-CSF | | | | | | | | | | | | |
| 91 | Gemcitabine (720 mg/m²) | 62 | 24 | — | | | | | | | | | | | | |
| 96 | | | | — | 6 | 2300 | 1 | 16500 | 6 | 1500 | 1 | 15300 | — | — | — | — |
| 97 | | | | G-CSF | | | | | | | | | | | | |
| 98 | Gemcitabine (900 mg/m²) Docetaxel (100 mg/m²) | 62 | 24 | — | — | 2300 | 1 | 14600 | 6 | 1700 | 1 | 12800 | 7 | 16 | 7 | 250 |
| 99 | | | | G-CSF | | | | | | | | | | | | |
| 112 | Gemcitabine (900 mg/m²) | | | — | | | | | | | | | | | | | hours prior to irradiation (5 or 10Gy; FIGS. 18A, 18B).

TABLE 3

| | | Fasting (hr) | | WBC | | | | ANC | | | |
|---|---|---|---|---|---|---|---|---|---|---|---|
| | | Pre | Post | Nadir* (Days) | cell/uL | Recovery** (Days) | Zenith cell/uL | Nadir* (Days) | cell/uL | Recovery** (Days) | Zenith cell/uL |
| Days | Treatment | | | | | | | | | | |
| 3 | Docetaxel 75 mg/m² + Cyclophosphamide 600 mg/m² | 140 | 40 | 15 | 1700 | 4 | 3900 | 15 | 561 | 4 | 2601 |
| 24 | Docetaxel 75 mg/m² + Cyclophosphamide 600 mg/m² | ad lib | — | 12 | 1200 | 6 | 4600 | 12 | 120 | 6 | 3036 |
| 45 | Docetaxel 75 mg/m² + Cyclophosphamide 600 mg/m² | ad lib | — | 12 | 1500 | 8 | 4100 | 12 | 216 | 8 | 2932 |
| 66 | Docetaxel 75 mg/m² + Cyclophosphamide 600 mg/m² | 20 | 24 | — | — | — | 5200 | — | — | — | 3567 |

Experiment 2

With reference to FIG. 18, fasting sensitizes malignant cells to irradiation. Murine breast (4T1-luc) cells were plated in 96-well cell culture plates (20,000/well), and allowed to equilibrate and reach confluency for 48 hours. Media was then switched to either low or high glucose media for 48

Viability was determined by the MIT assay (FIG. 18C). Statistical analysis was done by the Student's t-test (N=60).

With reference to FIG. 19, fasting sensitizes malignant cells to irradiation. Murine glioma (GL26) cells were plated in 96-well cell culture plates (20,000/well), and allowed to equilibrate and reach confluency for 48 hours. Media was then switched to either low or high glucose media for 48 hours prior to irradiation (5 or 10Gy; FIGS. 19A, 19B). Viability was determined by the MIT assay (FIG. 19C). Statistical analysis was done by the Student's t-test (N=60).

With Reference to FIG. 20, STS (fasting) sensitizes murine breast cancer cells to irradiation and enhances tumor control in mice. Female BALB/c mice weighing 20-25 g were subcutaneously injected with syngeneic breast cancer cells (4T1-luc; 2×10^5 cells/mouse). On day 13 the tumor progressed significantly to 300-500 mm³, and treatment began by fasting the mice for 48 hours prior to irradiation (IR; 5Gy). The second cycle of STS/IR (3Gy) was done 1 week later. Statistical analysis was done using Student's test for each day. *p<0.05.

With Reference to FIG. 21, STS (fasting) sensitizes murine glioma cancer cells to irradiation and enhances tumor control in mice. Female C57BL/6 mice weighing 25-30 g were subcutaneously injected with syngeneic glioma cancer cells (GL26; 3×10^5 cells/mouse). On day 27 the tumor progressed significantly to 500-1000 mm³, and treatment began by fasting the mice for 48 hours prior to irradiation (IR; 7.5Gy). The second cycle of STS/IR (3Gy) was done 1 week later. Statistical analysis was done using Student's test for each day. *p<0.05.

Experiment 3

A hypothesis was tested that the many changes in energy sources, growth and other extracellular factors caused by fasting not only prevent protection but also promote sensitization of a wide variety of cancer cells to chemotherapy drugs.

To explore whether fasting can synergistically enhance chemotherapy toxicity, various mouse cancer models were studied using murine breast cancer (4T1), melanoma (B16), glioma (GL26), and murine neuroblastoma (NXS2, Neuro-2-a), as well as human neuroblastoma (ACN) cells. Short-term starvation (STS), or fasting, was achieved by complete food withdrawal for 48-60 hours with continued access to water. As expected, chemotherapy given under an ad lib diet retarded the growth of subcutaneous tumors (FIG. 22 A-C). Remarkably, two cycles of fasting alone (48 hours each) were as effective as two cycles of chemotherapy treatment. Similar effects were observed in mice bearing subcutaneous melanoma masses (B16 cells), although the effect of fasting alone was not maintained after the second cycle (FIG. 22B), and also in mice bearing subcutaneous glioma masses (GL26 cells) (FIG. 22C). Fasting in the glioma model was applied only once due to the unusually rapid tumor growth in the control (ad lib, no chemotherapy) group. The greatest therapeutic index was observed when fasting was combined with either of the commonly used chemotherapy drugs, doxorubicin (DXR) or cyclophosphamide (CP) (FIG. 22 A-C). For 4T1 breast cancer, two fasting cycles resulted in a tumor size of less than half of that in the CP treatment alone group, even 20 days after the last treatment (FIG. 22A). Similar, effects were observed in subcutaneous glioma and melanoma models (FIG. 22 B-C). Notably, body weight lost during fasting was typically recovered within 3 days of refeeding even after chemotherapy treatment (FIG. 23 A-D), confirming that fasting does not exacerbate the effects of tumors and chemotherapy on weight loss in mice, consistent with the observations in the preliminary study of fasting and chemotherapy in patients.

The effect of fasting on chemotherapy was studied in metastatic models generated by intravenous injections of murine breast cancer cells (4T1), melanoma cells (B16), and 2 neuroblastoma cell lines (NXS2 and Neuro-2a) in immunocompetent mice. Fasting potentiated chemotherapy and extended the survival of all mice models of metastatic cancer (FIGS. 24-28). In the metastatic model of melanoma, mice were sacrificed early to determine the effect of STS on metastases. Interestingly, STS combined with DXR caused a reduction in metastasis of B16 melanoma cells to different organs compared to mice that received DXR under normal feeding (FIG. 25). For instance, lung metastases were found in 100% vs65% of mice that received DXR under normal feeding and fasting, respectively. In addition, unlike normally fed mice, metastases were not detected in the liver or spleen of fasted mice (FIG. 25).

To test the effect of multiple cycles of fasting and chemotherapy on an aggressive metastatic cancer, the survival of 2 metastatic mouse models of neuroblastoma was monitored. Long-term survival (over 180 days) was achieved in 42% of murine neuroblastoma (NXS2) bearing mice, which underwent 2 cycles of fasting with high dose DXR (16 mg/Kg) treatment (FIG. 26), compared to the 100% mortality in the ad lib group. To model advanced metastatic cancer, murine neuroblastoma cells (Neuro-2a) were intravenously injected into mice and the tumor was allowed to spread for 9 days before initiating chemotherapy. To test the effect of STS in combination with standard therapy in a metastatic model of neuroblastoma, fasting was combined with a cocktail of high-dose chemotherapy, based on that widely used to treat this children's malignancy (10 mg/Kg DXR+8 mg/Kg Cisplatin, CDDP). Remarkably, whereas all mice treated with the chemotherapy cocktail combined with an ad lib diet died by day 75, 25% of mice that were fasted in combination with the chemotherapy cocktail achieved long-term survival (over 300 days) (FIG. 27). To test whether many cycles of fasting (STS) can be effective in delaying neuroblastoma progression in the absence of chemotherapy, but also to test its effect on a human tumor model, 5 cycles of fasting were performed in immunocompromisednude mice subcutaneously injected with human ACNneuroblastoma cells (FIG. 29). After 36 days, 5 cycles of fasting were able to limit tumor size to half of that reached in normally fed mice (FIG. 29).

To model fasting in vitro, cancer cells were incubated in media containing serum collected from mice either fed ad lib or fasted for 48 hours. In agreement with results in mice, breast cancer cells (4T1) cultured in medium supplemented with serum from fasted mice were sensitized to both DXR and CP compared to the effect of incubation in serum from mice fed ad lib (FIG. 30). Because pronounced glucose and growth factor reduction (e.g., the 75% reduction in the growth factor IGF-I) are two key extracellular responses to fasting, cells were incubated in different glucose and serum concentrations based on blood glucose measurements from normally fed and fasted mice (FIG. 31), i.e., incubation in low glucose (0.5 g/L) with low serum (1% FBS), or normal glucose (1.0 and 2.0 g/L for human and murine cell lines respectively) with normal serum (10% FBS) for 24 hours before and also during drug treatment (FIG. 32). In agreement with the in vivo studies, glucose and serum restriction sensitized 15 out of 17 different cancer cells lines, including the murine melanoma (B16), glioma (GL26), and breast cancer (4T1) cells to DXR and/or CP (FIGS. 32-34). Furthermore, the reduction of either glucose or serum alone also enhanced DXR and/or CP toxicity to cancer cells, but was not as effective as the combination of both (FIGS. 33, 34). Of the many growth factors involved in fasting-dependent DSR, it was previously reported that reduced IGF-I is a key change, and that IGF-I infusion can reverse the protection of mice to chemotherapy. Here it is shown that IGF-I treatment of 4T1 and B16 cells also reverses the sensitization of cancer cells to DXR caused by glucose restriction, suggesting that STS sensitizes cancer cells, in part, by reducing IGF-I (FIG. 35).

To determine the mechanisms responsible for this STS-dependent sensitization, the effect of low glucose on DNA single and double strand breaks in cancer cells exposed to chemotherapy by the comet assay was studied. Glucose, which is the main energy source for metazoans, is particularly important to malignant cells, a phenomenon known as the Warburg effect, and elevated blood glucose promotes increased cancer growth. The reduction of glucose from the ad lib (2.0 g/L) to that reached after fasting (0.5 g/L) in combination with low serum condition (1% FBS), to also mimic the fasting-dependent reduction in blood growth factors and proteins, increased DNA damage more than chemotherapy alone, and the combination of 0.5 g/L glucose and chemotherapy promoted a remarkable 20-fold increase in DNA damage in both 4T1 breast cancer cells (FIG. 36A) and B16 melanoma cells (FIG. 36B). The effect of reduced glucose was instead additive with that of doxorubicin in the treatment of GL26 glioma cells (FIG. 36C).

To obtain an unbiased view of the gene expression changes occurring in cancer cells in response to fasting, genome-wide microarray analyses were performed on the heart, muscle, liver and subcutaneous 4T1 breast cancer tumor mass from mice that were either fasted for 48 hours or fed an ad lib diet. The microarray analysis clearly indicates that fasting differentially regulates genes involved in cellular proliferation (FIG. 37). Further, it was found that the expression of translation and ribosome biogenesis/assembly genes significantly increased in the autografted breast cancer (4T1), whereas in normal tissues they were either repressed or minimally affected (FIG. 38). In agreement with this increase in translational components, Akt and S6K phosphorylation was elevated and eIF2α phosphorylation was reduced in pre-starved cancer cells in autografted tumors (FIG. 39A), and also in vitro, particularly in combination with CP treatment (FIG. 39B). However, despite this starvation-dependent activation of translation mechanisms, cancer cell doubling was greatly reduced in vitro (FIG. 40), consistent with the retardation of tumor progression by fasting in vivo (FIGS. 36, 37). Translation is closely coupled with cell cycle progression and cell growth, and is a costly process that can consume 50-75% of the cellular energy in rapidly dividing cells. It is possible that the 4T1 tumor attempts to compensate for the lack of nutrients required for growth by increasing translation and as a result consume even more energy leading to cell death.

Because the stress resistance transcription factor FOXO3a is known to be inactivated by AKT, the effect of fasting on its expression was tested in 4T1 masses and normal tissue. It was found that FOXO3a was differentially regulated in response to fasting. Its expression was significantly repressed in the tumors, but induced in normal organs. (FIG. 41). It was also determined that the effect of fasting on another major stress response transcription factor, nuclear factor kappa B (NFkB), in the autografted breast tumor (4T1). RT-PCR showed differential expression of NFkB by fasting: its expression was largely repressed in the tumors, but highly induced in the normal organs (FIG. 41). Among the protective genes whose expression is induced by NFkB, heme oxygenase-1 (HO-1) is an evolutionarily conserved enzyme that is highly inducible in response to various stimuli including UVA and oxidative stress. It was found that fasting also repressed HO-1 expression in the tumors, but caused a major increase in tis expression in normal organs, consistent with those of FOXO3a and NFkB (FIG. 41). Student's t-test; *P<0.05, P<0.01, *P<0.001.

Because both FOXO3a and NFkB reduce oxidative stress via HO-1 and/or MnSOD, the level of reactive oxygen species (ROS) was measured using dihydroethidium (DHE) oxidation in 4T1 cells as a way to estimate superoxide levels under standard and STS conditions after treatment with CP (FIGS. 42, 43). Higher levels of DHE oxidation were detected in cancer cells following fasting/chemotherapy, suggesting increased oxidative stress and possibly superoxide levels. Moreover, it was found that caspase-3 levels were increased only in the allografted tumors following STS, but not in the normal organs in vivo (FIG. 44A) and also in vitro (FIG. 44B), in agreement with the effect of oxidants in promoting apoptosis and with the role of HO-1 in inhibiting caspase-3 activity. Apoptosis induced by glucose restriction in cancer cells has been suggested to also be promoted by autophagy. Glucose restriction in low serum incubation increased autophagy in 4T1 cells (FIG. 45) but the inhibition of autophagy by chloroquine further increased cell death indicating that low glucose does not promote cell death by an autophagy-dependent cell death (FIG. 46).

To confirm the role of HO-1 in fasting-dependent sensitization to chemotherapy, HO-1 expression was induced during fasting using hemin and found that the sensitization could be partially reversed (FIGS. 47, 48). Conversely, the HO-1 inhibitor zinc protoporphyrin (ZnPP) sensitized cancer cells to chemotherapy (FIGS. 49, 50). Together, these studies indicate that reduced HO-1 expression is part of the mechanism responsible for the fasting-dependent sensitization of 4T1 breast cancer cells.

In summary, it was shown that the major decreases in glucose, IGF-I, and possibly many other changes known to occur in response to starvation/fasting in cell culture and mice result in growth retardation and a major increase in cell death in a wide range of tumor cells (FIG. 51), particularly in combination with chemotherapy. These results suggest that multiple fasting cycles have the potential to provide both patient protection and cancer sensitization effects in cancer therapy.

Methods

Cell Culture

4T1-luc murine breast cancer cells were purchased from Siblech (Brookfield, CT). B16-fluc murine melanoma cells were provided by Noah Craft (UCLA). GL26 murine glioma, U87-MG human glioblastoma cells were provided by Thomas Chen (USC). PC3 and 22RV1 human prostate cancer cells were provided by Pinchas Cohen (UCLA). MCF-7 and C42B human breast cancer cells and HeLa human cervical cancer cells were provided by Amy Lee (USC). LOVO human colon cancer cells were provided by Darryl Shibata (USC). NXS2 and Neuro-2a murine neuroblastoma, human ACN and SH-SY5Y neuroblastoma, OVCAR human ovarian carcinoma, MZ-MEL human melanoma, A431 epidermoid carcinoma cells were routinely cultured in the Laboratory of Oncology of Gaslini Institute. 4T1 cells were stably transfected with LC3-GFP, which was a kind gift from Jae Jung at USC, for autophagy studies. All cells were routinely maintained in DMEM 10% FBS at 37° C., 5% CO2. To inhibit autophagy cells were treated with 5 μM chloroquine (CQ) for 48 hours during in vitro STS. To modulate HO-1 activity, 4T1 cells were treated with 10 μM hemin (Sigma) or 20 μM zinc protoporphyrin (ZnPP; Sigma) for 24 hours prior to and 24 hours during chemotherapy treatment.

Chemotherapy

Doxorubicin (DXR; Bedford Laboratories, USA) and cyclophosphamide (CP; Baxter, USA) were used in vitro and in vivo.

In vitro chemotherapy was performed by treating cells in medium containing chemotherapy for 24 hours. Optimum drug doses were determined for each individual cell line. For in vivo studies, DXR was injected intravenously via lateral tail veins, and CP was injected intraperitoneally.

Mouse Models of Cancer

All animal experiments were performed according to procedures approved by University of Southern California's Institutional Animal Care and Use Committee, and the licensing and ethical committee of the National cancer Research Institute, Genoa, Italy, and by the Italian Ministry of Health. To establish a subcutaneous cancer mouse model, 12 week-old female BALB/c, 12-week-old female and male C57BL/6 mice, and 7-week-old Nude mice were injected with 4T1 breast cancer cells, B16 melanoma and GL26 glioma cells, and ACN human neuroblastoma cells, respectively. For metastatic mouse models of cancer, 12-week-old female BALB/c, 12-week-old female and male C57BL/6 mice were injected intravenously via lateral tail veins with 2×105 4T1, B16, GL26 cells, respectively, and 6-week-old female A/J mice were injected via lateral tail veins with 2×105 NXS2, and 1×106 Neuro-2a cells. Prior to injection, cells in log phase of growth were harvested and suspended in PBS at 2×106 cells/ml, and 100 uL (2×105 cells/mouse) were injected subcutaneously in the lower back region or intravenously via the lateral tail veins. ACN and Neuro-2a cells were suspended in PBS at a density of 5×107 and 1×107 cells/ml, and 100 uL (5×106 ACN cells/mouse and 1×106 Neuro-2a cells/mouse) were injected subcutaneously in the lower back region or intravenously via the lateral tail veins, respectively. All mice were shaved prior to subcutaneous tumor injection, and were gently warmed prior to intravenous injections to dilate the veins. Body weights were determined periodically and tumor size was measured using a digital vernier caliper. Tumor volume was calculated using the following equation: tumor volume (mm3)=(length× width×height)×π/6, where the length, width and height are in mm.

In Vitro Fasting

Cellular fasting was done by glucose and/or serum restriction which was based on blood glucose measurements in fasted and normally fed mice; the lower level approximated to 0.5 g/L. and the upper level to 2.0 g/L. For human cell lines, normal glucose was considered as 1.0 g/L. Cells were washed twice with PBS before changing to fasting medium.

In Vivo Fasting

Animals were fasted for a total of 48-60 hours by complete deprivation of food but with free access to water. Mice were individually housed in a clean new cage to reduce cannibalism, coprophagy, and residual chow. Body weight was measured immediately before and after fasting.

In Vitro Assays

Cytotoxicity was measured by the ability to reduce methylthiazolyldiphenyl-tetrazolium bromide (MTT). Briefly, MTT was prepared at 5 mg/ml in PBS, diluted to a final concentration of 0.5 mg/ml for assays, and incubated for 3-4 hours at 37° C. Formazan crystals were dissolved overnight (16 hours) at 37° C. with 100 µl lysis buffer ((w/v) 15% SDS, (v/v) 50% dimethylformamide, pH 4.7). Survival was presented as percentage of MTT reduction level of treated cells to control cells. Absorbance was read at 570 nm using a microplate reader SpectraMax 250 (Molecular Devices) and SoftMax Pro 3.0 software (Molecular Devices).

Superoxide levels were estimated using oxidation of the fluorescent dye, DHE (dihydroethidine; Invitrogen, USA). Cells were cultured on slides, treated, and washed twice with PBS prior to incubation with DHE (10 µM; in 0.1% DMSO) for 30 minutes.

Immunoblotting Assay

Cells were rinsed once in ice-cold PBS and harvested in RIPAlysis buffer containing protease inhibitors (Roche) and a cocktail of phosphatase inhibitors (Sigma). Tumour tissues were homogenized in RIPAlysis buffer supplemented with the same protease and phosphatase inhibitors. Proteins from total lysates were resolved by 8-12% SDS-PAGE, and analyzed by immunoblotting using antibodies for GAPDH, Akt and phospho-Ser473 Akt, p70 S6 kinase and phospho-Thr389 p70 S6 kinase, eIF2α and phospho-Ser51 eIF2a, (1:1000-2000, Cell Signaling Technology).

Comet Assay Protocol

Cells were diluted to $10^5$/ml in culture medium (DMEM/F12 with 10% FBS), and treated with 50 µM DXR for 1 hour at 37° C. Cells were then washed once with ice cold PBS and subject to CometAssay (Trevigen, Inc, Gaithersburg, MD) according to the manufacturer's recommended procedure. Comet images were acquired with a Nikon Eclipse TE300 fluorescent microscope and analyzed with the Comet Score software (TriTek Corp., ver1.5). 100-300 cells were scored for each genotype/treatment group.

Blood Collection and Glucose Measurements

Mice were anesthetized with 2% inhalant isoflurane and blood was collected by left ventricular cardiac puncture. Blood was collected in tubes coated with K2-EDTA to process serum (BD, USA). Blood glucose was measured using the Precision Xtra blood glucose monitoring system (Abbott Laboratories, USA).

Microarray Analysis

RNA from tissues was isolated according the procedures described by the manufacturer using the RNeasy kit from Qiagen (cat #74106). Then, RNA was hybridized to BD-202-0202 chips from IlluminaBeadchips (San Diego, CA). Raw data were subjected to Z normalization as described previously. Parameterized significant analysis is finished according to the SAM protocol with ANOVA filtering (ANOVA p<0.05). Significant genes are selected for each pairwise comparison. Gene set enrichment was tested using the PAGE method as previously described. Figures were selected based on the names and descriptions provided by Gene Ontology Database and Pathway Data Set. Further gene regularly relation and canonic pathway analysis is done by the Ingenuity Pathway Analysis System (ingenuity Systems; Redwood City, CA).

Real Time PCR

RNA from tissues was isolated according the procedures described by the manufacturer using the RNeasy kit from Qiagen (cat #74106). cDNA was synthesized using the High Capacity cDNA Reverse Transcription Kit (AB Applied Biosystems cat #4368814) and RT-PCR was performed using the SYBR Green PCR master mix (AB Applied Biosystems cat #4309159). GAPDH gene was used as calibrator gene. Each treatment analyzed was performed with three biological replicates and at least three reactions were used to calculate the expression. The expression ratio was calculated according to the $2^{-\Delta\Delta CP}$ method.

Experiment 4

A variety of dietary formulations were tested in mouse models to validate a dietary regime for cancer patients undergoing chemotherapy. The target endpoint is a 20-75% reduction in serum glucose and/or IGF-1, which has been shown to be effective in the protection of the host and sensitization of a wide variety of cancer cells. The formulations are selected to provide a level of nutrients sufficient to maintain the normal body weight. Daily food intake, body weight along with general health (behavior and physical appearance) is monitored. At the end of each feeding schedule, blood is collected for glucose and IGF-1 determination. It has been found that a diet deficient in specific amino acids (AA-D) but with normal total calorie significantly reduces serum IGF-1 (FIG. 52) and glucose (FIG. 54A) if fed for 5 days (FIG. 52). This beneficial effect is increased if used in a re-feeding paradigm (FIGS. 53 and 54B) where short-term starvation is followed by the AA-D formulation.

A diet regime consisting of 2-days on a very-low caloric diet (VCM, 6% of normal caloric intake) followed by 1-day on an amino acid deficient formulation (AA) reduced serum IGF-1 levels significantly more than short-term starvation (STS) (FIG. 55A). Furthermore, this diet regime protected mice from the chemotherapy drug, doxorubicin (DXR) (FIG. 55B). Here, DXR is injected after 2-days of VCM upon initiation of re-feeding with the amino acid deficient formulation (AA).

It was determined that a low-calorie VegeGel formulation (equivalent to recommended 5 servings of vegetables) reduces serum glucose and IGF-1 similarly to short-term starvation (STS) (FIG. 56 A&B). Furthermore, it was demonstrated that a caloric-restricted ketogenic diet (90% of calories fat derived) for 3 days reduces serum IGF-1 and glucose (FIG. 6A&B, green triangles). Importantly, 1 day of this ketogenic diet followed by 2 days on theVegeGel formulation shows a beneficial effect in reducing glucose and IGF-I over the ketogenic diet alone (FIG. 57 A&B, red squares).

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of sensitizing cancer to chemotherapy drugs, the method comprising:

a) identifying a patient with cancer; and b) providing the patient with a first diet for a first predetermined period of time, the first diet providing the patient with at most 50% of the patient's normal caloric intake wherein at least 50% of the kilocalories are derived from fat;

c) providing the patient with a second diet for a second predetermined period of time, the second diet providing the patient with at most 500 kcal/day;

d) administering to the patient a chemotherapy agent during or after the patient consumes the second diet for at least 48 hours; and e) administering a replenishing composition to the patient for at least 5 days, the replenishing composition including essential amino acids, omega-3/6 essential fatty acids, minerals, and vegetable extracts, the vegetable extracts providing an equivalent of about five day servings of vegetable, where sources for the vegetable extract are selected from the group consisting of bok choy, kale, lettuce, asparagus, carrot, butternut squash, alfalfa, green peas, tomato, cabbage, cauliflower, and beets.

2. The method of claim 1, wherein the chemotherapy agent is a DNA alkylating agent, oxidant, or topoisomerase inhibitor.

3. The method of claim 1, wherein the chemotherapy agent is methyl methanesulfonate, cyclophosphamide, etoposide, doxorubicin, or menadionecisplatin, carboplatin and other platinum based drugs, gemcitabine, docetaxel, 5-FU, or topoisomerase inhibitors.

4. The method of claim 1, wherein the cancer is skin, colon, breast, esophageal, prostate, lung, uterus, ovary, and prostate cancer or glioma, melanoma, neuroblastoma, pheochromocytoma.

5. The method of claim 1 wherein the chemotherapy agent is provided for a longer period of time than is standard practice for the chemotherapy agent when the patient is not provided the first diet and the second diet.

6. The method of claim 1 wherein the first and second diet are administered during the chronic administration of the chemotherapy agent.

7. The method of claim 1 wherein the chemotherapy agent is provided for a shorter period of time than is standard practice for the chemotherapy agent when the patient is not provided the first diet and the second diet.

8. The method of claim 1 wherein the chemotherapy agent is administered in an amount that is at least 10% greater than the amount normally provided.

9. The method of claim 1 wherein the chemotherapy agent is administered in an amount that is at least 10% lower than the amount normally provided.

10. The method of claim 1 wherein the patient has exhibited a symptom of chemotherapeutic-related toxicity prior to step b).

11. The method of claim 1 wherein the patient has been diagnosed as terminal prior to step b).

12. The method of claim 1 wherein the first predetermined period of time is about a day and the second predetermined period of time is about 3 days.

13. The method of claim 1 wherein the second diet is at most 200 kcal/day.

* * * * *